US012503502B2

(12) United States Patent
Bae et al.

(10) Patent No.: US 12,503,502 B2
(45) Date of Patent: Dec. 23, 2025

(54) SH3YL1 ANTIBODIES, COMPOSITIONS COMPRISING THE SAME, AND VECTORS AND USES THEREOF

(71) Applicant: Celros Biotech, Seoul (KR)

(72) Inventors: Yun Soo Bae, Goyang-si (KR); Eunjung An, Siheung-si (KR); Jung-Yeon Yoo, Seoul (KR); Hyunbo Shim, Seoul (KR); Hye Eun Lee, Seoul (KR)

(73) Assignee: Celros Biotech, Seoul (KR)

( * ) Notice: Subject to any disclaimer, the term of this patent is extended or adjusted under 35 U.S.C. 154(b) by 69 days.

(21) Appl. No.: 18/515,723

(22) Filed: Nov. 21, 2023

(65) Prior Publication Data

US 2024/0158485 A1 May 16, 2024

Related U.S. Application Data

(62) Division of application No. 17/474,359, filed on Sep. 14, 2021, now Pat. No. 11,845,790.

(60) Provisional application No. 63/078,274, filed on Sep. 14, 2020.

(51) Int. Cl.

| | |
|---|---|
| ***A61K 39/00*** | (2006.01) |
| ***A61K 39/395*** | (2006.01) |
| ***A61P 1/16*** | (2006.01) |
| ***A61P 13/12*** | (2006.01) |
| ***C07K 16/18*** | (2006.01) |
| ***G01N 33/68*** | (2006.01) |

(52) U.S. Cl.

CPC ................ *C07K 16/18* (2013.01); *A61P 1/16* (2018.01); *A61P 13/12* (2018.01); *G01N 33/6854* (2013.01); *A61K 2039/505* (2013.01); *C07K 2317/52* (2013.01); *C07K 2317/55* (2013.01); *C07K 2317/565* (2013.01); *C07K 2317/622* (2013.01); *C07K 2317/624* (2013.01)

(58) Field of Classification Search

None

See application file for complete search history.

(56) References Cited

U.S. PATENT DOCUMENTS

| | | | |
|---|---|---|---|
| 9,896,730 | B2 | 2/2018 | Kan et al. |
| 2010/0111849 | A1 | 5/2010 | Boyden et al. |
| 2012/0004119 | A1 | 1/2012 | Lenburg et al. |

FOREIGN PATENT DOCUMENTS

| | | | |
|---|---|---|---|
| EP | 3305914 | A1 | 4/2018 |
| KR | 101240208 | B1 | 3/2013 |
| KR | 1020160143244 | A | 12/2016 |
| WO | 2013143026 | A1 | 10/2013 |

OTHER PUBLICATIONS

Choi et al. SH3YL1 protein as a novel biomarker for diabetic nephropathy in type 2 diabetes mellitus. Nutrition, Metabolism & Cardiovascular Diseases (2021) 31, 498e505. (Year: 2021).*

Gomaa et al. Assessment of SH3YL1 protein as a marker for diabetic nephropathy in type 2 diabetes mellitus. Egyptian Journal of Medical Research (EJMR), 3(3):222-237, 2022 (Year: 2022).*

Al-Jaghbeer, M., et al., Clinical Decision Support for In-Hospital Aki. J Am Soc Nephrol, 2018. 29(2):654-660.

Alobaidi et al.,; "Sepsis-Associated Acute Kidney Injury"; Semin Nephrol. January; (1): 2-11. doi:10.1016/j.semnephrol.2015.01.002; pp. 1-19.

Aoki, et al., A Novel Mouse Gene, Sh3yl1, is Expressed in the Anagen Hair Follicle, Journal of Investigative Dermatology, vol. 114, Issue 5, May 2000, pp. 1050-1056.

Bellomo, R., et al., Acute kidney injury in sepsis. Intensive Care Med, 2017. 43(6):816-828.

Bellomo, R., J.A. Kellum, and C. Ronco, Acute kidney injury. Lancet, 2012. 380 (9843):756-66.

Charlton, J.R., D. Portilla, and M.D. Okusa, A basic science view of acute kidney injury biomarkers. Nephrol Dial Transplant, 2014. 29(7):1301-11.

Faubel, S., et al., Cisplatin-induced acute renal failure is associated with an increase in the cytokines interleukin (IL)-1beta, IL-18, IL-6, and neutrophil infiltration in the kidney. J Pharmacol Exp Ther, 2007. 322(1):8-15.

Gluba et al., The role of Toll-like receptors in renal diseases. Nat Rev Nephrol. Apr. 2010;6(4):224-35, doi: 10.1038/nrneph.2010.16. Epub Feb. 23, 2010. PMID: 20177402.

Gowda, S., et al., Markers of renal function tests. N Am J Med Sci, 2010. 2(4):170-3.

Graham DB and Xavier RJ. Pathway paradigms revealed from the genetics of inflammatory bowel disease. Nature. 2020 578(7796):527-539.

(Continued)

*Primary Examiner* — Maher M Haddad

(74) *Attorney, Agent, or Firm* — Potomac Law Group, PLLC; Judith U. Kim

(57) ABSTRACT

The present disclosure relates to SH3YL1 monoclonal antibodies and compositions comprising the SH3YL1 monoclonal antibodies. The disclosure also relates to isolated nucleic acid molecules encoding the SH3YL1 antibodies, vectors comprising the nucleic acid molecules, and host cells comprising the vectors. Also disclosed are methods of modulating an immune response, methods of treating diabetic nephropathy, and methods of treating non-alcoholic steatosis hepatitis comprising administering the SH3YL1 antibodies. Also disclosed are methods of treating acute kidney injury and methods of treating inflammatory bowel disease comprising administering the SH3YL1 antibodies.

20 Claims, 36 Drawing Sheets

Specification includes a Sequence Listing.

(56) References Cited

OTHER PUBLICATIONS

Haase, M., et al., Accuracy of neutrophil gelatinase-associated lipocalin (NGAL) in diagnosis and prognosis in acute kidney injury: a systematic review and meta-analysis. Am J Kidney Dis, 2009. 54(6):1012-24.
Hasegawa, et al., SHSYL1 regulates dorsal ruffle formation by a novel phosphoinositide-binding domain, The Journal of Cell Biology, Nov. 5, 2011, vol. 193, pp. 901-916.
Hoste, E.A., et al., Epidemiology of acute kidney injury in critically ill patients: the multinational AKI-EPI study. Intensive Care Med, 2015. 41(8):1411-23.
International Search Report and Written Opinion dated Dec. 17, 2021, issued in International Application No. PCT/IB2021/058373.
Ismaili, N., M. Amzerin, and A. Flechon, Chemotherapy in advanced bladder cancer: current status and future. J Hematol Oncol, 2011. 4:35.
Kanwar, Y.S., et al., Diabetic nephropathy: mechanisms of renal disease progression. Exp Biol Med (Maywood), 2008. 233(1):4-11.
Kawai et al., "Toll-like Receptors and Their Crosstalk with Other Innate Receptors in Infection and Immunity", Immunity Review, Immunity 34, May 27, 2011, Elsevier Inc., pp. 637-650.
Khwaja, A., Kdigo clinical practice guidelines for acute kidney injury. Nephron Clin Pract, 2012. 120(4):c179-84.
Kim, D.G. et al., An Isoform of the Oncogenic Splice Variant AIMP2-DX2 Detected by a Novel Monoclonal Antibody, Biomolecules 10: 820 (2020).
Kobayashi et al., Dock4 forms a complex with SH3YL1 and regulates cancer cell migration, Cell Signal, May 2014;26 (5), pp. 1082-1088.
Liu, P., et al., Inhibition of CXCL1-CXCR2 axis ameliorates cisplatin-induced acute kidney injury by mediating inflammatory response. Biomed Pharmacother, 2020. 122:109693.
Miller, R.P., et al., Mechanisms of Cisplatin nephrotoxicity. Toxins (Basel), 2010. 2(11):2490-518.
Mishra, J., et al., Neutrophil gelatinase-associated lipocalin (NGAL) as a biomarker for acute renal injury after cardiac surgery. Lancet, 2005. 365(9466):1231-8.
Oh, S.W., The Cause and Treatment of Acute Kidney Injury. Korean J Med, 2019. 94(4):315-321.
Ozkok, A. and C.L. Edelstein, Pathophysiology of cisplatin-induced acute kidney injury. Biomed Res Int, 2014. 2014:967826.
Paul, "Fundamental Immunology, 3rd Edition," 229-295(1993), Raven Press.
Plichta DR, Graham DB, Subramanian S, and Xavier RJ, Therapeutic Opportunities in Inflammatory Bowel Disease: Mechanistic Dissection of Host-Microbiome Relationships. Cell 2019 178(5):1041-1056.
Ronco, C., R. Bellomo, and J.A. Kellum, Acute kidney injury. Lancet, 2019. 394(10212):1949-1964.
Rudikoff, S., et al., "Single amino acid substitution altering antigen-binding specificity," Proc. Natl. Acad. Sci. USA, 79(6):1979-83(1982).
Sabbisetti, V.S., et al., Blood kidney injury molecule-1 is a biomarker of acute and chronic kidney injury and predicts progression to ESRD in type I diabetes. J Am Soc Nephrol, 2014. 25(10):2177-86.
Schirmer M, Garner A, Vlamakis H, and Xavier RJ. Microbial genes and pathways in inflammatory bowel disease. Nat Rev Microbiol. 2019 17(8):497-511.
Shimomura et al., "Gene expression of Sh3d19, a novel adaptor protein with five Scrhomology 3 domains, in anagen mouse hair follicles," Journal of Dermatological Science, 2003, vol. 31, pp. 43-45, Elsevier, Amsterdam, Netherlands.
Takeuchi et al., "Pattern Recognition Receptors and Inflammation", Leading Edge Review, Cell 140, pp. 805-820, Mar. 19, 2010, Elsevier Inc.
Tanase, D.M., et al., The Predictive Role of the Biomarker Kidney Molecule-1 (KIM-1) in Acute Kidney Injury (AKI) Cisplatin-Induced Nephrotoxicity. Int J Mol Sci, 2019. 20(20).
Tugay, S., et al., Acute effects of gentamicin on glomerular and tubular functions in preterm neonates. Pediatr Nephrol, 2006. 21(10):1389-92.
Urbanek, et al. Function and interactions of the Ysc84/SH3yl1 family of actin- and lipid-binding proteins, Biochemical Society Transactions, 2015, vol. 43, pp. 111-116.
Vaidya, V.S., et al., Kidney injury molecule-1 outperforms traditional biomarkers of kidney injury in preclinical biomarker qualification studies. Nat Biotechnol, 2010. 28(5):478-85.
Yoo et al., "LPS-Induced Acute Kidney Injury Is Mediated by Nox4-SH3YL1", Cell Reports 33, 108245, Oct. 20, 2020, The Authors.https://doi.org/10.1016/j.celrep.2020.108245.
Zarogoulidis, K., et al., Treatment of non-small cell lung cancer (NSCLC). J Thorac Dis, 2013. 5 Suppl 4:S389-96.
The foreign patent and non-patent literature documents listed in this Form PTO/SB08 were cited by or submitted to the U.S. Patent and Trademark Office in parent U.S. Appl. No. 17/474,359, filed Sep. 14, 2021, which is relied upon for an earlier filing date under 35 U.S.C. § 120. In accordance with 37 C.F.R. § 1.98(d), these documents are not attached.
Gershoni, J.M. et al., "Epitope mapping—The first step in developing epitope-based vaccines," Biodrugs 21: 145-156 (2007).
Winkler et al., "Changing the antigen binding specificity by single point mutations of an anti-p24 (HIV-1) antibody," J. Immunol. 165:4505-4514 (2000).
Wuttke et al., "A catalog of genetic loci associated with kidney function from analyses of a million individuals," Nature Genetics 51: 957-972 (2019).

* cited by examiner

FIG. 15

SEQ ID NO:1 Amino Acid Sequence of VH of A3 Antibody

EVQLLESGGGLVQPGGSLRLSCAASGFTFSNYAMSWVRQAPGKGLEWVSVISSDNSSTYYADSVKGRYTISR
DNSKNTLYLQMNSLRAEDTAVYYCARVWRHFDYWGQGTLVTVSS

FIG. 16

SEQ ID NO:2 Nucleotide Sequence of VH of A3 Antibody

GAGGTGCAGCTGTTGGAGTCTGGGGGAGGCTTGGTACAGCCTGGGGGGTCCCTGAGACTCTCCTGTGC
AGCCTCTGGATTCACCTTTAGCAATTATGCTATGAGCTGGGTCCGCCAGGCTCCAGGGAAGGGGCTGGA
GTGGGTCTCAGTGATCTCTTCTGATAATAGTAGTACATATTACGCTGATTCTGTAAAAGGTCGGTACACC
ATCTCCAGAGACAATTCCAAGAACACGCTGTATCTGCAAATGAACAGCCTGAGAGCCGAGGACACGGCC
GTGTATTACTGTGCGAGAGTTTGGCGGCATTTCGACTACTGGGGCCAGGGTACACTGGTCACCGTGAGC
TCAG

FIG. 17

SEQ ID NO:3 Amino Acid Sequence of VL of A3 Antibody

QSVLTQPPSASGTPGQRVTISCSGSSSNIGSNNVNWYQQLPGTAPKLLIYADSHRPSGVPDRFSGSKSGTSAS
LAISGLRSEDEADYYCASWDSSLSGYVFGGGTKLTVL

FIG. 18

SEQ ID NO:4 Nucleotide Sequence of VL of A3 Antibody

CAGTCTGTGCTGACTCAGCCACCCTCAGCGTCTGGGACCCCCGGGCAGAGGGTCACCATCTCTTGTAGT
GGCTCTTCATCTAATATTGGCAGTAATAATGTCAACTGGTACCAGCAGCTCCCAGGAACGGCTCCCAAAC
TCCTCATCTATGCTGATAGTCATCGGCCAAGCGGGGTCCCTGACCGATTCTCTGGCTCCAAGTCTGGCAC
CTCAGCCTCCCTGGCCATCAGTGGGCTCCGGTCCGAGGATGAGGCTGATTATTACTGTGCTTCTTGGGAT
TCTAGCCTGAGTGGTTATGTCTTCGGCGGAGGCACCAAGCTGACGGTCCTA

FIG. 19

SEQ ID NO:5 Amino Acid Sequence of VH of A4 Antibody

EVQLLESGGGLVQPGGSLRLSCAASGFTFSNYYMSWVRQAPGKGLEWVSAISHNNSNTYYADSVKGRFTISR
DNSKNTLYLQMNSLRAEDTAVYYCARKFSFFDYWGQGTLVTVSS

FIG. 20

SEQ ID NO:6 Nucleotide Sequence of VH of A4 Antibody

GAGGTGCAGCTGTTGGAGTCCGGGGGAGGCTTGGTACAGCCTGGGGGGTCCCTGAGACTCTCCTGTGC
AGCCTCTGGATTCACCTTTAGCAATTATTATATGAGCTGGGTCCGCCAGGCTCCAGGGAAGGGGCTGGA
GTGGGTCTCAGCGATCTCTCATAATAATAGTAATACATATTACGCTGATTCTGTAAAAGGTCGGTTCACC
ATCTCCAGAGACAATTCCAAGAACACGCTGTATCTGCAAATGAACAGCCTGAGAGCCGAGGACACGGCC
GTGTATTACTGTGCGAGAAAGTTTTCTTTTTTCGACTACTGGGGCCAGGGTACACTGGTCACCGTGAGCT
CA

FIG. 21

SEQ ID NO:7 Amino Acid Sequence of VL of A4 Antibody

QSVLTQPPSASGTPGQRVTISCSGSSSNIGSNYVSWYQQLPGTAPKLLIYANSHRPSGVPDRFSGSKSGTSASL
AISGLRSEDEADYYCGAWDSSLNGYVFGGGTKLTVL

FIG. 22

SEQ ID NO:8 Nucleotide Sequence of VL of A4 Antibody

CAGTCTGTGCTGACTCAGCCACCCTCAGCGTCTGGGACCCCCGGGCAGAGGGTCACCATCTCTTGTAGT
GGCTCTTCATCTAATATTGGCAGTAATTATGTCTCCTGGTACCAGCAGCTCCCAGGAACGGCCCCCAAAC
TCCTCATCTATGCTAATAGTCATCGGCCAAGCGGGGTCCCTGACCGATTCTCTGGCTCCAAGTCTGGCAC
CTCAGCCTCCCTGGCCATCAGTGGGCTCCGGTCCGAGGATGAGGCTGATTATTACTGTGGTGCTTGGGA
TTCTAGCCTGAATGGTTATGTCTTCGGCGGAGGCACCAAGCTGACGGTCCTA

FIG. 23

SEQ ID NO:9 Amino Acid Sequence of CH of A3, A4, and S4A Antibodies

ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK

FIG. 24

SEQ ID NO:10 Amino Acid Sequence of CL of A3, A4, and S4A Antibodies

GQPKAAPSVTLFPPSSEELQANKATLVCLISDFYPGAVTVAWKADSSPVKAGVETTTPSKQSNNKYAASSYLS
LTPEQWKSHKSYSCQVTHEGSTVEKTVAPAECS

FIG. 25

SEQ ID NO:11 Amino Acid Sequence of SH3YL1

MNNPIPSNLKSEAKKAAKILREFTEITSRNGPDKIIPAHVIAKAKGLAILSVIKAGFLVTARGGSGIVVARLPDGK
WSAPSAIGIAGLGGGFEIGIEVSDLVIILNYDRAVEAFAKGGNLTLGGNLTVAVGPLGRNLEGNVALRSSAAVF
TYCKSRGLFAGVSLEGSCLIERKETNRKFYCQDIRAYDILFGDTPRPAQAEDLYEILDSFTEKYENEGQRINARK
AAREQRKSSAKELPPKPLSRPQQSSAPVQLNSGSQSNRNEYKLYPGLSSYHERVGNLNQPIEVTALYSFEGQQ
PGDLNFQAGDRITVISKTDSHFDWWEGKLRGQTGIFPANYVTMN

FIG. 26

SEQ ID NO:12 Nucleotide Sequence of SH3YL1

ATGAATAACCCTATACCTTCCAATTTGAAATCAGAAGCAAAAAAGGCTGCCAAAATATTAAGAGAATTCA
CAGAAATAACTTCCAGAAATGGACCTGATAAGATCATTCCTGCTCACGTAATTGCGAAGGCTAAAGGCC
TTGCAATTCTGTCTGTGATCAAAGCCGGGTTCCTGGTGACTGCCAGAGGAGGCAGCGGGATTGTAGTGG
CGCGCCTTCCAGATGGAAAATGGTCTGCACCCTCAGCCATTGGGATAGCTGGCCTTGGTGGAGGATTTG
AAATAGGAATTGAGGTATCAGACTTGGTGATAATTCTGAATTATGACCGTGCTGTAGAAGCTTTTGCAA
AAGGCGGAAATCTGACCCTCGGAGGGAACTTGACTGTGGCGGTTGGGCCCTTGGGAAGGAACTTGGAA
GGAAACGTGGCCCTGAGAAGCTCCGCTGCCGTCTTCACGTACTGCAAGTCAAGGGGACTCTTTGCAGGC
GTGTCTTTAGAAGGGAGCTGTTTGATTGAAAGGAAAGAAACTAATAGAAAATTTTATTGTCAAGATATC
CGAGCTTATGACATTTTATTTGGAGATACACCGCGGCCTGCTCAAGCCGAAGATCTTTATGAAATTCTTG
ATTCCTTTACTGAAAAGTATGAAAATGAAGGACAACGAATCAATGCAAGAAAAGCAGCAAGGGAGCAG
AGGAAGTCTTCTGCTAAAGAATTACCTCCAAAGCCATTGTCAAGACCACAGCAGTCATCTGCACCAGTCC
AGCTGAACTCTGGCTCTCAAAGTAACAGAAATGAATATAAGCTCTATCCTGGACTTTCCAGCTATCATGA
GAGAGTTGGCAATTTGAATCAACCCATAGAAGTGACAGCGCTGTATTCATTTGAAGGACAGCAGCCTGG
GGATTTGAATTTTCAAGCTGGAGACAGAATCACAGTTATATCAAAAACAGATTCACATTTTGATTGGTGG
GAAGGAAAACTTCGAGGTCAAACTGGCATTTTTCCAGCCAACTACGTAACCATGAATTAA

FIG. 27

SEQ ID NO:31 Amino Acid Sequence of VH of S4A Antibody

EVQLLESGGGLVQPGGSLRLSCAASGFTFSSYSMNWVRQAPGKGLEWVSWISPNSGSTDYAQKFQGRFTIS
RDNSKNTLYLQMNSLRAEDTAVYYCARTPPGTPFDYWGQGTLVTVSS

FIG. 28

SEQ ID NO:32 Nucleotide Sequence of VH of S4A Antibody

GAAGTGCAGCTGCTGGAAAGTGGAGGTGGACTGGTGCAGCCTGGCGGCAGCCTGCGCCTGAGCTGTG
CCGCCAGCGGATTCACCTTCAGCAGCTATAGCATGAACTGGGTTCGCCAAGCACCTGGCAAAGGCCTGG
AATGGGTGAGCTGGATCAGCCCTAACAGCGGCAGCACCGATTATGCCCAGAAATTTCAGGGCCGCTTTA
CCATCAGCCGCGATAACAGCAAAAACACCCTGTATCTGCAGATGAACAGCCTGCGCGCCGAGGACACCG
CAGTCTACTACTGTGCCCGCACCCCTCCTGGCACCCCTTTTGATTATTGGGGACAAGGTACTCTGGTGAC
CGTGAGCAGT

FIG. 29

SEQ ID NO:33 Amino Acid Sequence of VL of S4A Antibody

QSVLTQPPSASGTPGQRVTISCSGNNIGSKSVHWYQQLPGTAPRLLIYSTSNKHSGVPDRFSGSKSGTSASLAI
SGLHSEDEADYYCSSYTSSGTRVFGGGTKLTVL

FIG. 30

SEQ ID NO:34 Nucleotide Sequence of VL of S4A Antibody

CAGAGCGTGCTGACCCAGCCTCCTAGCGCCTCCGGTACACCAGGACAGCGCGTGACTATTAGCTGTAGC
GGCAACAACATCGGCAGCAAAAGCGTGCATTGGTACCAGCAACTGCCTGGAACTGCACCTAGGCTGCT
GATCTATAGCACCAGCAACAAACATAGCGGCGTTCCTGATCGCTTTAGCGGTAGCAAATCAGGCACCAG
CGCCAGCCTGGCCATCAGCGGCCTTCACTCCGAAGATGAAGCCGATTATTATTGTAGCAGCTATACCAGC
AGCGGCACCCGCGTGTTTGGTGGCGGTACCAAGCTGACCGTCCTA

FIG. 31

SEQ ID NO:35 Amino Acid Sequence of VH of 4F9 Antibody

EVQLVESGGGLVQPGGSLRLSCAASGFTFSDYAMSWVRQAPGKGLEWVSAIKSSGSSTYYADSVKGRFTISR
DNSKNTLYLQMNSLRAEDTAVYYCAKAEYEYLAFDIWGQGTLVTVSS

FIG. 32

SEQ ID NO:36 Nucleotide Sequence of VH of 4F9 Antibody

GAAGTACAGTTGGTCGAAAGTGGCGGTGGCCTCGTGCAACCGGGTGGTTCACTGCGTCTGAGCTGCGC
CGCCTCGGGTTTTACTTTCTCTGATTATGCAATGTCTTGGGTTCGTCAGGCGCCGGGCAAGGGTCTCGAA
TGGGTTTCAGCAATCAAATCTTCTGGTTCTTCTACTTACTATGCCGATTCAGTGAAGGGTCGCTTTACCAT
TTCCCGTGACAACTCTAAGAATACTCTGTATCTGCAGATGAACTCGCTGCGTGCCGAAGACACGGCCGTC
TATTATTGCGCCAAAGCAGAATACGAATACCTGGCATTCGATATCTGGGGTCAGGGCACTTTAGTGACC
GTCTCATCG

FIG. 33

SEQ ID NO:37 Amino Acid Sequence of VL of 4F9 Antibody

DIQMTQSPSSLSASVGDRVTITCRASQDISSWLNWYQQKPGKAPKLLIYATSTLQSGVPSRFSGSGSGTDFTL
TISSLQPEDFATYYCQQSYSSPWTFGQGTKVEIK

FIG. 34

SEQ ID NO:38 Nucleotide Sequence of VL of 4F9 Antibody

GACATTCAAATGACGCAGAGTCCCTCCTCACTGAGTGCTAGCGTGGGCGATCGTGTGACAATTACTTGTC
GCGCTAGCCAGGATATCTCTTCTTGGCTGAACTGGTATCAGCAGAAACCGGGCAAGGCGCCAAAATTGC
TGATTTACGCAACTTCCACTCTGCAGTCTGGTGTACCGTCCCGTTTCTCTGGCAGCGGTTCTGGTACGGA
TTTTACCCTGACCATCTCAAGCCTCCAGCCTGAAGATTTTGCCACCTATTATTGTCAGCAATCTTACTCTTC
TCCGTGGACGTTCGGGCAGGGAACTAAAGTGGAAATTAAA

FIG. 35

SEQ ID NO:39 Amino Acid Sequence of VH of 4F10 Antibody

EVQLVESGGGLVQPGGSLRLSCAASGFTFSDYAMSWVRQAPGKGLEWVSAIYSTGSSTYYADSVKGRFTISR
DNSKNTLYLQMNSLRAEDTAVYYCAKVGWYLFDYWGQGTLVTVSS

FIG. 36

SEQ ID NO:40 Nucleotide Sequence of VH of 4F10 Antibody

GAAGTACAGTTGGTCGAAAGTGGCGGTGGCCTCGTGCAACCGGGTGGTTCACTGCGTCTGAGCTGCGC
CGCCTCGGGTTTTACTTTCTCTGATTATGCAATGTCTTGGGTTCGTCAGGCGCCGGGCAAGGGTCTCGAA
TGGGTTTCAGCAATCTACTCTACTGGTTCTTCTACTTACTATGCCGATTCAGTGAAGGGTCGCTTTACCAT
TTCCCGTGACAACTCTAAGAATACTCTGTATCTGCAGATGAACTCGCTGCGTGCCGAAGACACGGCCGTC
TATTATTGCGCCAAAGTTGGTTGGTACCTGTTTGATTACTGGGGTCAGGGTACTCTGGTGACCGTCTCAT
CG

FIG. 37

SEQ ID NO:41 Amino Acid Sequence of VL of 4F10 Antibody

DIQMTQSPSSLSASVGDRVTITCRASQDISSWLNWYQQKPGKAPKLLIYATSTLQSGVPSRFSGSGSGTDFTL
TISSLQPEDFATYYCQQSYSSPWTFGQGTKVEIK

FIG. 38

SEQ ID NO:42 Nucleotide Sequence of VL of 4F10 Antibody

GACATTCAAATGACGCAGAGTCCCTCCTCACTGAGTGCTAGCGTGGGCGATCGTGTGACAATTACTTGTC
GCGCTAGCCAGGATATCTCTTCTTGGCTGAACTGGTATCAGCAGAAACCGGGCAAGGCGCCAAAATTGC
TGATTTACGCAACTTCCACTCTGCAGTCTGGTGTACCGTCCCGTTTCTCTGGCAGCGGTTCTGGTACGGA
TTTTACCCTGACCATCTCAAGCCTCCAGCCTGAAGATTTTGCCACCTATTATTGTCAGCAATCTTACTCTTC
TCCGTGGACGTTCGGGCAGGGAACTAAAGTGGAAATTAAA

FIG. 39

SEQ ID NO:43 Amino Acid Sequence of VH of 5D5 Antibody

EVQLVESGGGLVQPGGSLRLSCAASGFTFSDYAMSWVRQAPGKGLEWVSSISSTGSTTYYADSVKGRFTISR
DNSKNTLYLQMNSLRAEDTAVYYCAKVLYEYLYFDYWGQGTLVTVSS

FIG. 40

SEQ ID NO:44 Nucleotide Sequence of VH of 5D5 Antibody

GAAGTACAGTTGGTCGAAAGTGGCGGTGGCCTCGTGCAACCGGGTGGTTCACTGCGTCTGAGCTGCGC
CGCCTCGGGTTTTACTTTCTCTGATTATGCAATGTCTTGGGTTCGTCAGGCGCCGGGCAAGGGTCTCGAA
TGGGTTTCATCTATCTCTTCTACTGGTTCTACTACTTACTATGCCGATTCAGTGAAGGGTCGCTTTACCATT
TCCCGTGACAACTCTAAGAATACTCTGTATCTGCAGATGAACTCGCTGCGTGCCGAAGACACGGCCGTCT
ATTATTGCGCCAAAGTTCTGTACGAATACCTGTACTTCGATTACTGGGGTCAGGGCACTTTAGTGACCGT
CTCATCG

FIG. 41

SEQ ID NO:45 Amino Acid Sequence of VL of 5D5 Antibody

DIQMTQSPSSLSASVGDRVTITCRASQDIRNWLNWYQQKPGKAPKLLIYAASSLQSGVPSRFSGSGSGTDFTL
TISSLQPEDFATYYCQQSYSSPWTFGQGTKVEIK

FIG. 42

SEQ ID NO:46 Nucleotide Sequence of VL of 5D5 Antibody

GACATTCAAATGACGCAGAGTCCCTCCTCACTGAGTGCTAGCGTGGGCGATCGTGTGACAATTACTTGTC
GCGCTAGCCAGGATATCCGTAATTGGCTGAACTGGTATCAGCAGAAACCGGGCAAGGCGCCAAAATTG
CTGATTTACGCAGCATCCTCTCTGCAGTCTGGTGTACCGTCCCGTTTCTCTGGCAGCGGTTCTGGTACGG
ATTTTACCCTGACCATCTCAAGCCTCCAGCCTGAAGATTTTGCCACCTATTATTGTCAGCAATCTTACTCTT
CTCCGTGGACGTTCGGGCAGGGAACTAAAGTGGAAATTAAA

FIG. 43

SEQ ID NO:47 Amino Acid Sequence of VH of 4G4 Antibody

EVQLVESGGGLVQPGGSLRLSCAASGFTFSNYAMSWVRQAPGKGLEWVSAISGSGSSTYYADSVKGRFTISR
DNSKNTLYLQMNSLRAEDTAVYYCAKAEYSYLYFDIWGQGTLVTVSS

FIG. 44

SEQ ID NO:48 Nucleotide Sequence of VH of 4G4 Antibody

GAAGTACAGTTGGTCGAAAGTGGCGGTGGCCTCGTGCAACCGGGTGGTTCACTGCGTCTGAGCTGCGC
CGCCTCGGGTTTTACTTTCTCTAATTATGCAATGTCTTGGGTTCGTCAGGCGCCGGGCAAGGGTCTCGAA
TGGGTTTCAGCAATCTCTGGTTCTGGTTCTTCTACTTACTATGCCGATTCAGTGAAGGGTCGCTTTACCAT
TTCCCGTGACAACTCTAAGAATACTCTGTATCTGCAGATGAACTCGCTGCGTGCCGAAGACACGGCCGTC
TATTATTGCGCCAAAGCAGAATACTCTTACCTGTACTTCGATATCTGGGGTCAGGGCACTTTAGTGACCG
TCTCATCG

FIG. 45

SEQ ID NO:49 Amino Acid Sequence of VL of 4G4 Antibody

DIQMTQSPSSLSASVGDRVTITCRASQSISNWLNWYQQKPGKAPKLLIYAASRLQSGVPSRFSGSGSGTDFTL
TISSLQPEDFATYYCQQSYSSPWTFGQGTKVEIK

FIG. 46

SEQ ID NO:50 Nucleotide Sequence of VL of 4G4 Antibody

GACATTCAAATGACGCAGAGTCCCTCCTCACTGAGTGCTAGCGTGGGCGATCGTGTGACAATTACTTGTC
GCGCTAGCCAGTCTATCTCTAATTGGCTGAACTGGTATCAGCAGAAACCGGGCAAGGCGCCAAAATTGC
TGATTTACGCAGCATCCCGTCTGCAGTCTGGTGTACCGTCCCGTTTCTCTGGCAGCGGTTCTGGTACGGA
TTTTACCCTGACCATCTCAAGCCTCCAGCCTGAAGATTTTGCCACCTATTATTGTCAGCAATCTTACTCTTC
TCCGTGGACGTTCGGGCAGGGAACTAAAGTGGAAATTAAA

FIG. 47

SEQ ID NO:51 Amino Acid Sequence of VH of 3E11 Antibody

EVQLVESGGGLVQPGGSLRLSCAASGFTFSNYAMSWVRQAPGKGLEWVSAISGSGSSTYYADSVKGRFTISR
DNSKNTLYLQMNSLRAEDTAVYYCAKAEYSYLYFDIWGQGTLVTVSS

FIG. 48

SEQ ID NO:52 Nucleotide Sequence of VH of 3E11 Antibody

GAAGTACAGTTGGTCGAAAGTGGCGGTGGCCTCGTGCAACCGGGTGGTTCACTGCGTCTGAGCTGCGC
CGCCTCGGGTTTTACTTTCTCTAATTATGCAATGTCTTGGGTTCGTCAGGCGCCGGGCAAGGGTCTCGAA
TGGGTTTCAGCAATCTCTGGTTCTGGTTCTTCTACTTACTATGCCGATTCAGTGAAGGGTCGCTTTACCAT
TTCCCGTGACAACTCTAAGAATACTCTGTATCTGCAGATGAACTCGCTGCGTGCCGAAGACACGGCCGTC
TATTATTGCGCCAAAGCAGAATACTCTTACCTGTACTTCGATATCTGGGGTCAGGGCACTTTAGTGACCG
TCTCATCG

FIG. 49

SEQ ID NO:53 Amino Acid Sequence of VL of 3E11 Antibody

DIQMTQSPSSLSASVGDRVTITCRASQDIANYLNWYQQKPGKAPKLLIYATSTLQSGVPSRFSGSGSGTDFTL
TISSLQPEDFATYYCQQSYSSPWTFGQGTKVEIK

FIG. 50

SEQ ID NO:54 Nucleotide Sequence of VL of 3E11 Antibody

GACATTCAAATGACGCAGAGTCCCTCCTCACTGAGTGCTAGCGTGGGCGATCGTGTGACAATTACTTGTC
GCGCTAGCCAGGATATCGCAAATTACCTGAACTGGTATCAGCAGAAACCGGGCAAGGCGCCAAAATTG
CTGATTTACGCAACTTCCACTCTGCAGTCTGGTGTACCGTCCCGTTTCTCTGGCAGCGGTTCTGGTACGG
ATTTTACCCTGACCATCTCAAGCCTCCAGCCTGAAGATTTTGCCACCTATTATTGTCAGCAATCTTACTCTT
CTCCGTGGACGTTCGGGCAGGGAACTAAAGTGGAAATTAAA

FIG. 51

SEQ ID NO:55 Amino Acid Sequence of VH of 4H7 Antibody

EVQLVESGGGLVQPGGSLRLSCAASGFTFSTYGMSWVRQAPGKGLEWVSAISSSGGSIYYADSVKGRFTISR
DNSKNTLYLQMNSLRAEDTAVYYCAKVSYPGLAFDIWGQGTLVTVSS

FIG. 52

SEQ ID NO:56 Nucleotide Sequence of VH of 4H7 Antibody

GAAGTACAGTTGGTCGAAAGTGGCGGTGGCCTCGTGCAACCGGGTGGTTCACTGCGTCTGAGCTGCGC
CGCCTCGGGTTTTACTTTCTCTACTTATGGTATGTCTTGGGTTCGTCAGGCGCCGGGCAAGGGTCTCGAA
TGGGTTTCAGCAATCTCTTCTTCTGGTGGTTCTATCTACTATGCCGATTCAGTGAAGGGTCGCTTTACCAT
TTCCCGTGACAACTCTAAGAATACTCTGTATCTGCAGATGAACTCGCTGCGTGCCGAAGACACGGCCGTC
TATTATTGCGCCAAAGTTTCTTACCCGGGTCTGGCATTCGATATCTGGGGTCAGGGCACTTTAGTGACCG
TCTCATCG

FIG. 53

SEQ ID NO:57 Amino Acid Sequence of VL of 4H7 Antibody

DIQMTQSPSSLSASVGDRVTITCRASQTISNYLNWYQQKPGKAPKLLIYATSSLQSGVPSRFSGSGSGTDFTLT
ISSLQPEDFATYYCQQSYSSPWTFGQGTKVEIK

FIG. 54

SEQ ID NO:58 Nucleotide Sequence of VL of 4H7 Antibody

GACATTCAAATGACGCAGAGTCCCTCCTCACTGAGTGCTAGCGTGGGCGATCGTGTGACAATTACTTGTC
GCGCTAGCCAGACTATCTCTAATTACCTGAACTGGTATCAGCAGAAACCGGGCAAGGCGCCAAAATTGC
TGATTTACGCAACTTCCTCTCTGCAGTCTGGTGTACCGTCCCGTTTCTCTGGCAGCGGTTCTGGTACGGAT
TTTACCCTGACCATCTCAAGCCTCCAGCCTGAAGATTTTGCCACCTATTATTGTCAGCAATCTTACTCTTCT
CCGTGGACGTTCGGGCAGGGAACTAAAGTGGAAATTAAA

UC : ulcerative colitis
CD : Crohn's disease

FIG. 65

| | 5D5 | 3E11 | 4F10 |
|---|---|---|---|
| Kd (M) | $5.49 \times 10^{-9}$ | $3.56 \times 10^{-9}$ | $4.04 \times 10^{-10}$ |

| | 4G4 | 4F9 | 4H7 |
|---|---|---|---|
| Kd (M) | $2.96 \times 10^{-9}$ | $3.63 \times 10^{-9}$ | $3.43 \times 10^{-9}$ |

| | S4A |
|---|---|
| Kd (M) | $2.06 \times 10^{-9}$ |

FIG. 66

SEQ ID NO:59 Amino Acid Sequence of Human TLR5 Extracellular Domain (Amino Acids 21-639 of hTLR5-FC)

IPSCSFDGRIAFYRFCNLTQVPQVLNTTERLLLSFNYIRTVTASSFPFLEQLQLLELGSQYTPLTIDKEAFRNLPNL
RILDLGSSKIYFLHPDAFQGLFHLFELRLYFCGLSDAVLKDGYFRNLKALTRLDLSKNQIRSLYLHPSFGKLNSLKS
IDFSSNQIFLVCEHELEPLQGKTLSFFSLAANSLYSRVSVDWGKCMNPFRNMVLEILDVSGNGWTVDITGNFS
NAISKSQAFSLILAHHIMGAGFGFHNIKDPDQNTFAGLARSSVRHLDLSHGFVFSLNSRVFETLKDLKVLNLAY
NKINKIADEAFYGLDNLQVLNLSYNLLGELYSSNFYGLPKVAYIDLQKNHIAIIQDQTFKFLEKLQTLDLRDNALT
TIHFIPSIPDIFLSGNKLVTLPKINLTANLIHLSENRLENLDILYFLLRVPHLQILILNQNRFSSCSGDQTPSENPSLE
QLFLGENMLQLAWETELCWDVFEGLSHLQVLYLNHNYLNSLPPGVFSHLTALRGLSLNSNRLTVLSHNDLPA
NLEILDISRNQLLAPNPDVFVSLSVLDITHNKFICECELSTFINWLNHTNVTIAGPPADIYCVYPDSFSGVSLFSLS
TEGCDEEEVLKSLK

SH3YL1 ANTIBODIES, COMPOSITIONS COMPRISING THE SAME, AND VECTORS AND USES THEREOF

CROSS-REFERENCE TO RELATED APPLICATIONS

This application is a divisional of U.S. application Ser. No. 17/474,359, filed Sep. 14, 2021, which claims the benefit of the filing date of U.S. Appl. No. 63/078,274 filed Sep. 14, 2020, the disclosure of which is incorporated herein by reference in its entirety.

REFERENCE TO SEQUENCE LISTING SUBMITTED ELECTRONICALLY

This application contains a Sequence Listing, which has been electronically submitted in XML format via Patent Center, and is hereby incorporated by reference in its entirety. Said XML copy, created on Feb. 2, 2024, is named 2713-000111502 SEQL.xml and is 136,850 bytes in size.

FIELD OF THE INVENTION

The present disclosure relates to SH3YL1 monoclonal antibodies and compositions comprising the SH3YL1 monoclonal antibodies. The disclosure also relates to isolated nucleic acid molecules encoding the SH3YL1 antibodies, vectors comprising the nucleic acid molecules, and host cells comprising the vectors. Also disclosed are methods of modulating an immune response, methods of treating diabetic nephropathy, and methods of treating non-alcoholic steatohepatitis comprising administering the SH3YL1 antibodies. Also disclosed are methods of treating acute kidney injury and methods of treating inflammatory bowel disease comprising administering the SH3YL1 antibodies.

BACKGROUND

SH3YL1 was first identified from skin keratinocytes and regulates the hair cycle (*J Invest Dermatol.* 2000, 114, 1050-1056). The protein is divided by two functional domains. The COOH-terminal region contains the SYLF (SH3YL1, Ysc84p/Lsb4p, Lsb3p, and plant FYVE proteins) domain, which interacts with phosphatidylinositol 3,4,5-trisphosphate (PI(3,4,5)P3) and phosphatidylinositol 3,4,5-bisphosphate (PI(3,4)P2) in the circular dorsal ruffle in response to PDGF, and the NH3-terminal region has a Src homology 3 (SH3) domain, which interacts with proline rich region (PRR) (*J Cell Biol.* 2011, 193, 901-916; *Biochem Soc Trans.* 2015, 43, 111-116). Moreover, SH3YL1 was shown to interact with Rac GEF Dock4 protein, which stimulates cell migration through Rac1 activation (*Cell Signal.* 2014, 26, 1082-1088).

Toll-like receptors (TLRs) recognize pathogen-associated molecular patterns (PAMPs) of microorganisms, including bacteria, viruses and fungi. Innate immunity not only kills invading microorganisms but also triggers acute cellular responses leading to sepsis and its associated organ failure (Alobaidi et al., 2015; Gluba et al., 2010; Kawai and Akira, 2011; Takeuchi and Akira, 2010).

SUMMARY OF THE INVENTION

Disclosed herein are monoclonal antibodies comprising:

(a) a heavy chain variable region comprising a heavy chain complementarity determining region 1 (CDR1) comprising the amino acid sequence NYAMS (SEQ ID NO:13), a heavy chain CDR2 comprising the amino acid sequence VISSDNSSTYYADSVKG (SEQ ID NO:14), and a heavy chain CDR3 comprising the amino acid sequence VWRHFDY (SEQ ID NO:15);

(b) a light chain variable region comprising a light chain CDR1 comprising the amino acid sequence SGSSSNIGSNNVN (SEQ ID NO:16), a light chain CDR2 comprising the amino acid sequence ADSHRPS (SEQ ID NO:17), and a light chain CDR3 comprising the amino acid sequence ASWDSSLSGYV (SEQ ID NO:18);

(c) a heavy chain variable region comprising a heavy chain CDR1 comprising the amino acid sequence NYYMS (SEQ ID NO:19), a heavy chain CDR2 comprising the amino acid sequence AISHNNSNTYYADSVKG (SEQ ID NO:20), and a heavy chain CDR3 comprising the amino acid sequence KFSFFDY (SEQ ID NO:21); or (d) a light chain variable region comprising a light chain CDR1 comprising the amino acid sequence SGSSSNIGSNYVS (SEQ ID NO:22), a light chain CDR2 comprising the amino acid sequence ANSHRPS (SEQ ID NO:23), and a light chain CDR3 comprising the amino acid sequence GAWDSSLNGYV (SEQ ID NO:24).

In some embodiments, the antibodies comprise:

(a) a heavy chain variable region comprising a heavy chain complementarity determining region 1 (CDR1) comprising the amino acid sequence NYAMS (SEQ ID NO:13), a heavy chain CDR2 comprising the amino acid sequence VISSDNSSTYYADSVKG (SEQ ID NO:14), and a heavy chain CDR3 comprising the amino acid sequence VWRHFDY (SEQ ID NO:15), and (b) a light chain variable region comprising a light chain CDR1 comprising the amino acid sequence SGSSSNIGSNNVN (SEQ ID NO:16), a light chain CDR2 comprising the amino acid sequence ADSHRPS (SEQ ID NO:17), and a light chain CDR3 comprising the amino acid sequence ASWDSSLSGYV (SEQ ID NO:18); or (c) a heavy chain variable region comprising a heavy chain CDR1 comprising the amino acid sequence NYYMS (SEQ ID NO:19), a heavy chain CDR2 comprising the amino acid sequence AISHNNSNTYYADSVKG (SEQ ID NO:20), and a heavy chain CDR3 comprising the amino acid sequence KFSFFDY (SEQ ID NO:21), and (d) a light chain variable region comprising a light chain CDR1 comprising the amino acid sequence SGSSSNIGSNYVS (SEQ ID NO:22), a light chain CDR2 comprising the amino acid sequence ANSHRPS (SEQ ID NO:23), and a light chain CDR3 comprising the amino acid sequence GAWDSSLNGYV (SEQ ID NO:24).

Also disclosed herein are monoclonal antibodies comprising:

(a) a heavy chain variable region comprising
a heavy chain complementarity determining region 1 (CDR1) comprising the amino acid sequence of SEQ ID NO:63,
a heavy chain CDR2 comprising the amino acid sequence of SEQ ID NO:64, and
a heavy chain CDR3 comprising the amino acid sequence of SEQ ID NO:65;

(b) a light chain variable region comprising
a light chain CDR1 comprising the amino acid sequence of SEQ ID NO:66,
a light chain CDR2 comprising the amino acid sequence of SEQ ID NO:67, and
a light chain CDR3 comprising the amino acid sequence of SEQ ID NO:68;

(c) a heavy chain variable region comprising
a heavy chain CDR1 comprising the amino acid sequence of SEQ ID NO:69,
a heavy chain CDR2 comprising the amino acid sequence of SEQ ID NO:70, and
a heavy chain CDR3 comprising the amino acid sequence of SEQ ID NO:71;

(d) a light chain variable region comprising
a light chain CDR1 comprising the amino acid sequence of SEQ ID NO:72,
a light chain CDR2 comprising the amino acid sequence of SEQ ID NO:73, and
a light chain CDR3 comprising the amino acid sequence of SEQ ID NO:74;

(e) a heavy chain variable region comprising
a heavy chain CDR1 comprising the amino acid sequence of SEQ ID NO:69,
a heavy chain CDR2 comprising the amino acid sequence of SEQ ID NO:75, and
a heavy chain CDR3 comprising the amino acid sequence of SEQ ID NO:76;

(f) a light chain variable region comprising
a light chain CDR1 comprising the amino acid sequence of SEQ ID NO:77,
a light chain CDR2 comprising the amino acid sequence of SEQ ID NO:78, and
a light chain CDR3 comprising the amino acid sequence of SEQ ID NO:79;

(g) a heavy chain variable region comprising
a heavy chain CDR1 comprising the amino acid sequence of SEQ ID NO:69,
a heavy chain CDR2 comprising the amino acid sequence of SEQ ID NO:80, and
a heavy chain CDR3 comprising the amino acid sequence of SEQ ID NO:81;

(h) a light chain variable region comprising
a light chain CDR1 comprising the amino acid sequence of SEQ ID NO:82,
a light chain CDR2 comprising the amino acid sequence of SEQ ID NO:83, and
a light chain CDR3 comprising the amino acid sequence of SEQ ID NO:84;

(i) a heavy chain variable region comprising
a heavy chain CDR1 comprising the amino acid sequence of SEQ ID NO:13,
a heavy chain CDR2 comprising the amino acid sequence of SEQ ID NO:85, and
a heavy chain CDR3 comprising the amino acid sequence of SEQ ID NO:86;

(j) a light chain variable region comprising
a light chain CDR1 comprising the amino acid sequence of SEQ ID NO:87,
a light chain CDR2 comprising the amino acid sequence of SEQ ID NO:88, and
a light chain CDR3 comprising the amino acid sequence of SEQ ID NO:74;

(k) a heavy chain variable region comprising
a heavy chain CDR1 comprising the amino acid sequence of SEQ ID NO:89,
a heavy chain CDR2 comprising the amino acid sequence of SEQ ID NO:90, and
a heavy chain CDR3 comprising the amino acid sequence of SEQ ID NO:91;

(l) a light chain variable region comprising
a light chain CDR1 comprising the amino acid sequence of SEQ ID NO:92,
a light chain CDR2 comprising the amino acid sequence of SEQ ID NO:73, and
a light chain CDR3 comprising the amino acid sequence of SEQ ID NO:74;

(m) a heavy chain variable region comprising
a heavy chain CDR1 comprising the amino acid sequence of SEQ ID NO:93,
a heavy chain CDR2 comprising the amino acid sequence of SEQ ID NO:94, and
a heavy chain CDR3 comprising the amino acid sequence of SEQ ID NO:95; or (n) a light chain variable region comprising
a light chain CDR1 comprising the amino acid sequence of SEQ ID NO:96,
a light chain CDR2 comprising the amino acid sequence of SEQ ID NO:97, and
a light chain CDR3 comprising the amino acid sequence of SEQ ID NO:74.

In some embodiments, the monoclonal antibodies comprise:

(a) a heavy chain variable region comprising
a heavy chain complementarity determining region 1 (CDR1) comprising the amino acid sequence of SEQ ID NO:63,
a heavy chain CDR2 comprising the amino acid sequence of SEQ ID NO:64, and
a heavy chain CDR3 comprising the amino acid sequence of SEQ ID NO:65; and (b) a light chain variable region comprising
a light chain CDR1 comprising the amino acid sequence of SEQ ID NO:66,
a light chain CDR2 comprising the amino acid sequence of SEQ ID NO:67, and
a light chain CDR3 comprising the amino acid sequence of SEQ ID NO:68;

(c) a heavy chain variable region comprising
a heavy chain CDR1 comprising the amino acid sequence of SEQ ID NO:69,
a heavy chain CDR2 comprising the amino acid sequence of SEQ ID NO:70, and
a heavy chain CDR3 comprising the amino acid sequence of SEQ ID NO:71; and (d) a light chain variable region comprising
a light chain CDR1 comprising the amino acid sequence of SEQ ID NO:72,
a light chain CDR2 comprising the amino acid sequence of SEQ ID NO:73, and
a light chain CDR3 comprising the amino acid sequence of SEQ ID NO:74;

(e) a heavy chain variable region comprising
a heavy chain CDR1 comprising the amino acid sequence of SEQ ID NO:69,
a heavy chain CDR2 comprising the amino acid sequence of SEQ ID NO:75, and
a heavy chain CDR3 comprising the amino acid sequence of SEQ ID NO:76; and
(f) a light chain variable region comprising
a light chain CDR1 comprising the amino acid sequence of SEQ ID NO:77,
a light chain CDR2 comprising the amino acid sequence of SEQ ID NO:78, and
a light chain CDR3 comprising the amino acid sequence of SEQ ID NO:79;
(g) a heavy chain variable region comprising
a heavy chain CDR1 comprising the amino acid sequence of SEQ ID NO:69,
a heavy chain CDR2 comprising the amino acid sequence of SEQ ID NO:80, and
a heavy chain CDR3 comprising the amino acid sequence of SEQ ID NO:81; and
(h) a light chain variable region comprising
a light chain CDR1 comprising the amino acid sequence of SEQ ID NO:82,
a light chain CDR2 comprising the amino acid sequence of SEQ ID NO:83, and
a light chain CDR3 comprising the amino acid sequence of SEQ ID NO:84;
(i) a heavy chain variable region comprising
a heavy chain CDR1 comprising the amino acid sequence of SEQ ID NO:13,
a heavy chain CDR2 comprising the amino acid sequence of SEQ ID NO:85, and
a heavy chain CDR3 comprising the amino acid sequence of SEQ ID NO:86; and
(j) a light chain variable region comprising
a light chain CDR1 comprising the amino acid sequence of SEQ ID NO:87,
a light chain CDR2 comprising the amino acid sequence of SEQ ID NO:88, and
a light chain CDR3 comprising the amino acid sequence of SEQ ID NO:74;
(k) a heavy chain variable region comprising
a heavy chain CDR1 comprising the amino acid sequence of SEQ ID NO:89,
a heavy chain CDR2 comprising the amino acid sequence of SEQ ID NO:90, and
a heavy chain CDR3 comprising the amino acid sequence of SEQ ID NO:91; and
(l) a light chain variable region comprising
a light chain CDR1 comprising the amino acid sequence of SEQ ID NO:92,
a light chain CDR2 comprising the amino acid sequence of SEQ ID NO:73, and
a light chain CDR3 comprising the amino acid sequence of SEQ ID NO:74; or
(m) a heavy chain variable region comprising
a heavy chain CDR1 comprising the amino acid sequence of SEQ ID NO:93,
a heavy chain CDR2 comprising the amino acid sequence of SEQ ID NO:94, and
a heavy chain CDR3 comprising the amino acid sequence of SEQ ID NO:95; and
(n) a light chain variable region comprising
a light chain CDR1 comprising the amino acid sequence of SEQ ID NO:96,
a light chain CDR2 comprising the amino acid sequence of SEQ ID NO:97, and
a light chain CDR3 comprising the amino acid sequence of SEQ ID NO:74.

In some embodiments, the heavy chain variable region comprises the amino acid sequence of SEQ ID NO:1 or 5. In some embodiments, the heavy chain variable region comprises the amino acid sequence of SEQ ID NO:31, 35, 39, 43, 47, 51, or 55.

In some embodiments, the light chain variable region comprises the amino acid sequence of SEQ ID NO:3 or 7. In some embodiments, the light chain variable region comprises the amino acid sequence of SEQ ID NO:33, 37, 41, 45, 49, 53, or 57.

The antibodies can further comprise heavy and/or light chain constant regions. In some embodiments, the heavy chain constant region is selected from the group consisting of human immunoglobulins $IgG_1$, $IgG_2$, $IgG_3$, and $IgG_4$. In some embodiments, the heavy chain constant region comprises an amino acid sequence of SEQ ID NO:9. In some embodiments, the heavy chain constant region comprises an amino acid sequence of SEQ ID NO:61.

In some embodiments, the light chain constant region is selected from the group consisting of human immunoglobulins IgGκ and IgGλ. In some embodiments, the light chain constant region comprises an amino acid sequence of SEQ ID NO:10. In some embodiments, the light chain constant region comprises an amino acid sequence of SEQ ID NO:62.

The antibodies can be a human antibody. The antibodies can be a single chain antibody (scFv), Fab, or dsFV.

Disclosed herein are monoclonal antibodies that bind to the same epitope of human SH3 domain-containing YSC84-like 1 (SH3YL1) as the antibodies disclosed herein.

Disclosed herein are monoclonal antibodies that specifically bind to human SH3 domain-containing YSC84-like 1 (SH3YL1) at an epitope comprising the amino acid sequence DSHFDWWE (SEQ ID NO:25).

Also disclosed herein are monoclonal antibodies that specifically bind to human SH3 domain-containing YSC84-like 1 (SH3YL1) at an epitope comprising the amino acid sequence LYEILDSF (SEQ ID NO:26).

Also disclosed are monoclonal antibodies that specifically bind to human SH3 domain-containing YSC84-like 1 (SH3YL1) at an epitope comprising the amino acid sequence of SEQ ID NO:98, 99, 100, or 60.

In some embodiments, the antibodies can further comprise a detectable label.

Disclosed herein are isolated nucleic acid molecules encoding the heavy chain variable region or heavy chain of the antibodies disclosed herein. Disclosed herein are isolated nucleic acid molecules encoding the light chain variable region or light chain of the antibodies disclosed herein. Disclosed herein are isolated nucleic acid molecules encoding the heavy chain variable region or heavy chain of the antibodies disclosed herein and 7 and the light chain variable region or light chain of the antibodies disclosed herein. In some embodiments, the nucleic acid molecule encodes a heavy chain variable region comprising the amino acid sequence of SEQ ID NO:1 or 5. In some embodiments, the nucleic acid molecule encodes a light chain variable region comprising the amino acid sequence of SEQ ID NO:3 or 7. In some embodiments, the nucleic acid molecule encodes a heavy chain variable region comprising the amino acid sequence of SEQ ID NO:31, 35, 39, 43, 47, 51, or 55. In some embodiments, the nucleic acid molecule encodes a light chain variable region comprising the amino acid sequence of SEQ ID NO:33, 37, 41, 45, 49, 53, or 57.

Also disclosed herein are isolated vectors comprising one or more of the nucleic acid molecules disclosed herein.

Also disclosed herein are host cells comprising one or more of the nucleic acid molecules disclosed herein, the vector disclosed herein. In some embodiments, the host cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

Disclosed herein are methods of producing a monoclonal antibody that binds to human SH3YL1 comprising culturing the host cell disclosed herein so that the nucleic acid molecule is expressed and the antibody is produced.

Disclosed herein are monoclonal antibodies that specifically bind to human SH3YL1 and is encoded by one or more of the isolated nucleic acid molecules disclosed herein.

Disclosed herein are pharmaceutical compositions comprising an antibody disclosed herein and a pharmaceutically acceptable excipient.

Disclosed herein are pharmaceutical compositions comprising an antibody, a nucleic acid molecule, a vector, or a host cell disclosed herein; and a pharmaceutically acceptable excipient.

Disclosed herein are methods of modulating an immune response in a subject, the method comprising administering to the subject an effective amount of an antibody, a nucleic acid molecule, a vector, a host cell, and/or a pharmaceutical composition disclosed herein. In some embodiments, the methods enhance or induce the immune response of the subject.

Disclosed herein are methods of treating diabetic nephropathy in a subject, the method comprising administering to the subject an effective amount of an antibody, a nucleic acid molecule, a vector, a host cell, and/or a pharmaceutical composition disclosed herein. In some embodiments, the methods further comprise administering to the subject losartan.

Disclosed herein are methods of treating non-alcoholic steatosis hepatitis in a subject, the method comprising administering to the subject an effective amount of an antibody, a nucleic acid molecule, a vector, a host cell, and/or a pharmaceutical composition disclosed herein.

Disclosed herein are methods for detecting SH3YL1 in a sample, comprising contacting the sample with an antibody disclosed herein.

Also disclosed are methods of treating acute kidney injury in a subject, the method comprising administering to the subject an effective amount of an antibody, a nucleic acid molecule, a vector, a host cell, and/or a pharmaceutical composition disclosed herein.

Disclosed herein are methods of treating inflammatory bowel disease in a subject, the method comprising administering to the subject an effective amount an antibody, a nucleic acid molecule, a vector, a host cell, and/or a pharmaceutical composition disclosed herein.

In some embodiments, the subject is human.

Also disclosed herein are kits comprising an antibody, a nucleic acid molecule, a vector, a host cell, and/or a pharmaceutical composition disclosed herein, and (a) a detection reagent, (b) an SH3YL1 antigen, (c) a notice that reflects approval for use or sale for human administration, or d) a combination thereof.

BRIEF DESCRIPTION OF THE DRAWINGS

The above and other aspects, features, and advantages of certain embodiments of the disclosure will be more apparent from the following description taken in conjunction with the accompanying drawings.

FIG. 15. Amino acid sequence of VH of A3 (SEQ ID NO:1).

FIG. 16. Nucleotide sequence of VH of A3 (SEQ ID NO:2).

FIG. 17. Amino acid sequence of VL of A3 (SEQ ID NO:3).

FIG. 18. Nucleotide sequence of VL of A3 (SEQ ID NO:4).

FIG. 19. Amino acid sequence of VH of A4 (SEQ ID NO:5).

FIG. 20. Nucleotide sequence of VH of A4 (SEQ ID NO:6).

FIG. 21. Amino acid sequence of VL of A4 (SEQ ID NO:7).

FIG. 22. Nucleotide sequence of VL of A4 (SEQ ID NO:8).

FIG. 23. Amino acid sequence of CH of A3, A4, and S4A (SEQ ID NO:9).

FIG. 24. Amino Acid sequence of CL of A3, A4, and S4A (SEQ ID NO:10).

FIG. 25. Amino acid sequence of SH3YL1 (SEQ ID NO:11)

FIG. 26. Nucleotide sequence of SH3YL1 (SEQ ID NO:12).

FIG. 27. Amino acid sequence of VH of S4A (SEQ ID NO:31).

FIG. 28. Nucleotide sequence of VH of S4A (SEQ ID NO:32).

FIG. 29. Amino acid sequence of VL of S4A (SEQ ID NO:33).

FIG. 30. Nucleotide sequence of VL of S4A (SEQ ID NO:34).

FIG. 31. Amino acid sequence of VH of 4F9 (SEQ ID NO:35).

FIG. 32. Nucleotide sequence of VH of 4F9 (SEQ ID NO:36).

FIG. 33. Amino acid sequence of VL of 4F9 (SEQ ID NO:37).

FIG. 34. Nucleotide sequence of VL of 4F9 (SEQ ID NO:38).

FIG. 35. Amino acid sequence of VH of 4F10 (SEQ ID NO:39).

FIG. 36. Nucleotide sequence of VH of 4F10 (SEQ ID NO:40).

FIG. 37. Amino acid sequence of VL of 4F10 (SEQ ID NO:41).

FIG. 38. Nucleotide sequence of VL of 4F10 (SEQ ID NO:42).

FIG. 39. Amino acid sequence of VH of 5D5 (SEQ ID NO:43).

FIG. 40. Nucleotide sequence of VH of 5D5 (SEQ ID NO:44).

FIG. 41. Amino acid sequence of VL of 5D5 (SEQ ID NO:45).

FIG. 42. Nucleotide sequence of VL of 5D5 (SEQ ID NO:46).

FIG. 43. Amino acid sequence of VH of 4G4 (SEQ ID NO:47).

FIG. 44. Nucleotide sequence of VH of 4G4 (SEQ ID NO:48).

FIG. 45. Amino acid sequence of VL of 4G4 (SEQ ID NO:49).

FIG. 46. Nucleotide sequence of VL of 4G4 (SEQ ID NO:50).

FIG. 47. Amino acid sequence of VH of 3E11 (SEQ ID NO:51).

FIG. 48. Nucleotide sequence of VH of 3E11 (SEQ ID NO:52).

FIG. 49. Amino acid sequence of VL of 3E11 (SEQ ID NO:53).

FIG. 50. Nucleotide sequence of VL of 3E11 (SEQ ID NO:54).

FIG. 51. Amino acid sequence of VH of 4H7 (SEQ ID NO:55).

FIG. 52. Nucleotide sequence of VH of 4H7 (SEQ ID NO:56).

FIG. 53. Amino acid sequence of VL of 4H7 (SEQ ID NO:57).

FIG. 54. Nucleotide sequence of VL of 4H7 (SEQ ID NO:58).

FIG. 55A. Secretion of SH3YL1 protein were induced in kidney tubular epithelial cells in response to cisplatin (20 μg/ml) stimulation. Kidney tubular epithelial cells were incubated with cisplatin (20 μg/ml) for 9 and 24 hrs. Cell supernatants were concentrated were subjected into immunoblotting with antibody to SH3YL1. FIGS. 55B-55D. Serum creatinine, blood urea nitrogen (BUN), and serum cystatin C were measured using the indicated ELISA kits described in “Materials & Methods” (Example 3.1) in the serum (N>9 per group, data shown as mean±SEM, $P<0.001$, $P<0.01$, $P<0.05$ as determined by student's t-test). FIGS. 55E-55F. Urinary albumin and albumin to creatinine ratio (ACR) were measured in urine (N>9 per group, data shown as mean±SEM, $P<0.001$, $P<0.005$, $P<0.01$ as determined by student's t-test).

FIG. 59A. The kidney section were stained with a hematoxylin and eosin solution. FIG. 59B. Histological changes due to tubular injury score were quantified by the percent of tubules that displayed cell necrosis, loss of brush border, cast formation, and tubule dilatation as follows: 0, none; 1, 1-25%; 2, 26-50%; 3, >50% (N>9 per group, data shown as mean±SEM, P<0.001 as determined by student's t-test).

(FIG. 60A) Kidney sections were stained with TdT-UDP nick end labeling. TUNEL positive areas were visualized by fluorescence microscopy (LSM880 airyscan, Carl Zeiss vison system) (FIG. 60B) Mean fluorescence intensity of TUNEL positive regions in 5 fields of each kidney (N>9 per group, data shown as mean±SEM, P<0.005, P<0.05 as determined by student's t-test).

FIG. 61A. Level of serum SH3YL1 in DSS-induced colitis model. FIG. 61B. Level of serum SH3YL1 in IBD patients.

FIG. 62A. Scheme of DSS-induced colitis model. FIG. 62B. Photomicrography of the colon tissues with H&E staining. FIG. 62C. Numeric grading of the H&E stained slides in FIG. 62B.

FIG. 63A. Scheme of DSS-induced colitis model. FIG. 63B. Photomicrography of the colon tissues with H&E staining. FIG. 63C. Numeric grading of the H&E stained slides in FIG. 63B.

FIG. 65. Binding affinity of antibodies 5D5, 3E11, 44F10, 4G4, 4F9, 4H7, and S4A.

FIG. 66. Amino acid sequence of human TLR5 extracellular domain (aa 21-639) of hTLR5-FC (SEQ ID NO:59).

DETAILED DESCRIPTION

Figure 1:
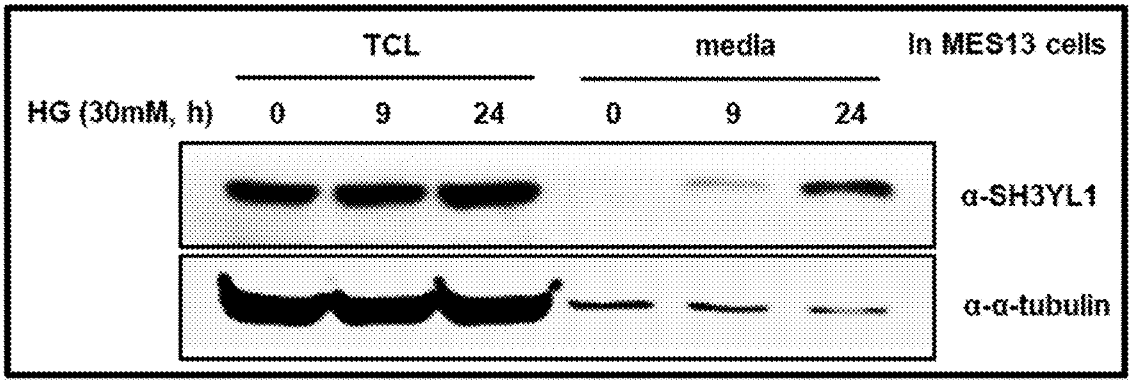
FIG. 1. Secretion of SH3YL1 protein were induced in MES13 mesangial cells in response to high glucose (HG) stimulation. Mouse mesangial cell line (MES13) were incubated with 30 mM of HG for 9 and 24 hrs. Cell supernatants were concentrated were subjected into immunoblotting with antibody to SH3YL1.

Cytosolic proteins are required for the regulation of NADPH oxidase (Nox) isozymes. SH3 domain-containing YSC84-like 1 (SH3YL1), as a novel Nox4 cytosolic regulator, mediates lipopolysaccharide (LPS)-induced $H_2O_2$ generation, leading to acute kidney injury. The SYLF region and SH3 domain of SH3YL1 contribute to forming a complex with Nox4-p22$^{phox}$. Interaction of p22$^{phox}$ with SH3YL1 was triggered by LPS, and the complex induced $H_2O_2$ generation and pro-inflammatory cytokine expression in mouse tubular epithelial cells. After LPS injection, SH3YL1 knockout mice showed lower levels of acute kidney injury biomarkers, decreased secretion of pro-inflammatory cytokines, decreased infiltration of macrophages and reduced tubular damage compared with WT mice. The results strongly suggest that SH3YL1 is involved in renal failure in LPS-induced AKI mice. Taken together, the formation of a ternary complex of p22$^{phox}$-SH3YL1-Nox4 leading to $H_2O_2$ generation induces severe renal failure in the LPS-induced AKI model.

To identify Nox4 regulator from kidney tissue, yeast two hybrid screening system with the COOH-terminal region of Nox4 was performed as bait. Based on this screening results, it was determined that SH3 domain containing YSC84-like 1 (SH3YL1) as a Nox4 regulator. SH3YL1 contained SH3 domain in COOH-terminal region and SYLF (SH3YL1, Ysc84p/Lsb4p, Lsb3p, and plant FYVE proteins) domain in NH3-terminal region. Two functional domains mediate cellular events including cell growth and migration. Disclosed herein is the role of SH3YL1 as a novel regulator of Nox4 and the novel function of the SH3YL1-Nox4 axis in sepsis-induced AKI.

Reference will now be made in detail to embodiments, examples of which are illustrated in the accompanying drawings, wherein like reference numerals refer to like elements throughout. In this regard, the present embodiments can have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising."

As used herein, the terms "about" and "approximately," when used to modify a numeric value or numeric range, indicate that deviations of 5% to 10% above and 5% to 10% below the value or range remain within the intended meaning of the recited value or range.

Antibodies

Disclosed herein are monoclonal antibodies comprising:
(a) a heavy chain variable region comprising
a heavy chain complementarity determining region 1 (CDR1) comprising the amino acid sequence NYAMS (SEQ ID NO:13),
a heavy chain CDR2 comprising the amino acid sequence VISSDNSSTYYADSVKG (SEQ ID NO:14), and
a heavy chain CDR3 comprising the amino acid sequence VWRHFDY (SEQ ID NO:15);
(b) a light chain variable region comprising
a light chain CDR1 comprising the amino acid sequence SGSSSNIGSNNVN (SEQ ID NO:16),
a light chain CDR2 comprising the amino acid sequence ADSHRPS (SEQ ID NO:17), and
a light chain CDR3 comprising the amino acid sequence ASWDSSLSGYV (SEQ ID NO:18);
(c) a heavy chain variable region comprising
a heavy chain CDR1 comprising the amino acid sequence NYYMS (SEQ ID NO:19),
a heavy chain CDR2 comprising the amino acid sequence AISHNNSNTYYADSVKG (SEQ ID NO:20), and
a heavy chain CDR3 comprising the amino acid sequence KFSFFDY (SEQ ID NO:21); or (d) a light chain variable region comprising
a light chain CDR1 comprising the amino acid sequence SGSSSNIGSNYVS (SEQ ID NO:22),
a light chain CDR2 comprising the amino acid sequence ANSHRPS (SEQ ID NO:23), and
a light chain CDR3 comprising the amino acid sequence GAWDSSLNGYV (SEQ ID NO:24).
(a) In some embodiments, the antibodies comprise:
(e) a heavy chain variable region comprising
a heavy chain complementarity determining region 1 (CDR1) comprising the amino acid sequence NYAMS (SEQ ID NO:13),
a heavy chain CDR2 comprising the amino acid sequence VISSDNSSTYYADSVKG (SEQ ID NO:14), and
a heavy chain CDR3 comprising the amino acid sequence VWRHFDY (SEQ ID NO:15), and
(f) a light chain variable region comprising
a light chain CDR1 comprising the amino acid sequence SGSSSNIGSNNVN (SEQ ID NO:16),
a light chain CDR2 comprising the amino acid sequence ADSHRPS (SEQ ID NO:17), and
a light chain CDR3 comprising the amino acid sequence ASWDSSLSGYV (SEQ ID NO:18); or
(g) a heavy chain variable region comprising
a heavy chain CDR1 comprising the amino acid sequence NYYMS (SEQ ID NO:19),
a heavy chain CDR2 comprising the amino acid sequence AISHNNSNTYYADSVKG (SEQ ID NO:20), and
a heavy chain CDR3 comprising the amino acid sequence KFSFFDY (SEQ ID NO:21), and
(h) a light chain variable region comprising
a light chain CDR1 comprising the amino acid sequence SGSSSNIGSNYVS (SEQ ID NO:22),
a light chain CDR2 comprising the amino acid sequence ANSHRPS (SEQ ID NO:23), and
a light chain CDR3 comprising the amino acid sequence GAWDSSLNGYV (SEQ ID NO:24).

Also disclosed herein are monoclonal antibodies comprising:
(a) a heavy chain variable region comprising
a heavy chain complementarity determining region 1 (CDR1) comprising the amino acid sequence of SEQ ID NO:63,
a heavy chain CDR2 comprising the amino acid sequence of SEQ ID NO:64, and
a heavy chain CDR3 comprising the amino acid sequence of SEQ ID NO:65;
(b) a light chain variable region comprising
a light chain CDR1 comprising the amino acid sequence of SEQ ID NO:66,
a light chain CDR2 comprising the amino acid sequence of SEQ ID NO:67, and
a light chain CDR3 comprising the amino acid sequence of SEQ ID NO:68;
(c) a heavy chain variable region comprising
a heavy chain CDR1 comprising the amino acid sequence of SEQ ID NO:69,
a heavy chain CDR2 comprising the amino acid sequence of SEQ ID NO:70, and
a heavy chain CDR3 comprising the amino acid sequence of SEQ ID NO:71;
(d) a light chain variable region comprising
a light chain CDR1 comprising the amino acid sequence of SEQ ID NO:72,
a light chain CDR2 comprising the amino acid sequence of SEQ ID NO:73, and
a light chain CDR3 comprising the amino acid sequence of SEQ ID NO:74;
(e) a heavy chain variable region comprising
a heavy chain CDR1 comprising the amino acid sequence of SEQ ID NO:69,
a heavy chain CDR2 comprising the amino acid sequence of SEQ ID NO:75, and
a heavy chain CDR3 comprising the amino acid sequence of SEQ ID NO:76;
(f) a light chain variable region comprising
a light chain CDR1 comprising the amino acid sequence of SEQ ID NO:77,
a light chain CDR2 comprising the amino acid sequence of SEQ ID NO:78, and
a light chain CDR3 comprising the amino acid sequence of SEQ ID NO:79;
(g) a heavy chain variable region comprising
a heavy chain CDR1 comprising the amino acid sequence of SEQ ID NO:69,
a heavy chain CDR2 comprising the amino acid sequence of SEQ ID NO:80, and
a heavy chain CDR3 comprising the amino acid sequence of SEQ ID NO:81;
(h) a light chain variable region comprising
a light chain CDR1 comprising the amino acid sequence of SEQ ID NO:82,
a light chain CDR2 comprising the amino acid sequence of SEQ ID NO:83, and
a light chain CDR3 comprising the amino acid sequence of SEQ ID NO:84;
(i) a heavy chain variable region comprising
a heavy chain CDR1 comprising the amino acid sequence of SEQ ID NO:13,
a heavy chain CDR2 comprising the amino acid sequence of SEQ ID NO:85, and
a heavy chain CDR3 comprising the amino acid sequence of SEQ ID NO:86;
(j) a light chain variable region comprising
a light chain CDR1 comprising the amino acid sequence of SEQ ID NO:87,
a light chain CDR2 comprising the amino acid sequence of SEQ ID NO:88, and
a light chain CDR3 comprising the amino acid sequence of SEQ ID NO:74;
(k) a heavy chain variable region comprising
a heavy chain CDR1 comprising the amino acid sequence of SEQ ID NO:89,
a heavy chain CDR2 comprising the amino acid sequence of SEQ ID NO:90, and
a heavy chain CDR3 comprising the amino acid sequence of SEQ ID NO:91;
(l) a light chain variable region comprising
a light chain CDR1 comprising the amino acid sequence of SEQ ID NO:92,
a light chain CDR2 comprising the amino acid sequence of SEQ ID NO:73, and
a light chain CDR3 comprising the amino acid sequence of SEQ ID NO:74;
(m) a heavy chain variable region comprising
a heavy chain CDR1 comprising the amino acid sequence of SEQ ID NO:93,
a heavy chain CDR2 comprising the amino acid sequence of SEQ ID NO:94, and
a heavy chain CDR3 comprising the amino acid sequence of SEQ ID NO:95; or (n) a light chain variable region comprising
a light chain CDR1 comprising the amino acid sequence of SEQ ID NO:96,
a light chain CDR2 comprising the amino acid sequence of SEQ ID NO:97, and
a light chain CDR3 comprising the amino acid sequence of SEQ ID NO:74.

In some embodiments, the monoclonal antibodies comprise:

(a) a heavy chain variable region comprising
a heavy chain complementarity determining region 1 (CDR1) comprising the amino acid sequence of SEQ ID NO:63,
a heavy chain CDR2 comprising the amino acid sequence of SEQ ID NO:64, and
a heavy chain CDR3 comprising the amino acid sequence of SEQ ID NO:65; and
(b) a light chain variable region comprising
a light chain CDR1 comprising the amino acid sequence of SEQ ID NO:66,
a light chain CDR2 comprising the amino acid sequence of SEQ ID NO:67, and
a light chain CDR3 comprising the amino acid sequence of SEQ ID NO:68;
(c) a heavy chain variable region comprising
a heavy chain CDR1 comprising the amino acid sequence of SEQ ID NO:69,
a heavy chain CDR2 comprising the amino acid sequence of SEQ ID NO:70, and
a heavy chain CDR3 comprising the amino acid sequence of SEQ ID NO:71; and
(d) a light chain variable region comprising
a light chain CDR1 comprising the amino acid sequence of SEQ ID NO:72,
a light chain CDR2 comprising the amino acid sequence of SEQ ID NO:73, and
a light chain CDR3 comprising the amino acid sequence of SEQ ID NO:74;
(e) a heavy chain variable region comprising
a heavy chain CDR1 comprising the amino acid sequence of SEQ ID NO:69,
a heavy chain CDR2 comprising the amino acid sequence of SEQ ID NO:75, and
a heavy chain CDR3 comprising the amino acid sequence of SEQ ID NO:76; and
(f) a light chain variable region comprising
a light chain CDR1 comprising the amino acid sequence of SEQ ID NO:77,
a light chain CDR2 comprising the amino acid sequence of SEQ ID NO:78, and
a light chain CDR3 comprising the amino acid sequence of SEQ ID NO:79;
(g) a heavy chain variable region comprising
a heavy chain CDR1 comprising the amino acid sequence of SEQ ID NO:69,
a heavy chain CDR2 comprising the amino acid sequence of SEQ ID NO:80, and
a heavy chain CDR3 comprising the amino acid sequence of SEQ ID NO:81; and
(h) a light chain variable region comprising
a light chain CDR1 comprising the amino acid sequence of SEQ ID NO:82,
a light chain CDR2 comprising the amino acid sequence of SEQ ID NO:83, and
a light chain CDR3 comprising the amino acid sequence of SEQ ID NO:84;
(i) a heavy chain variable region comprising
a heavy chain CDR1 comprising the amino acid sequence of SEQ ID NO:13,
a heavy chain CDR2 comprising the amino acid sequence of SEQ ID NO:85, and
a heavy chain CDR3 comprising the amino acid sequence of SEQ ID NO:86; and
(j) a light chain variable region comprising
a light chain CDR1 comprising the amino acid sequence of SEQ ID NO:87,
a light chain CDR2 comprising the amino acid sequence of SEQ ID NO:88, and
a light chain CDR3 comprising the amino acid sequence of SEQ ID NO:74;
(k) a heavy chain variable region comprising
a heavy chain CDR1 comprising the amino acid sequence of SEQ ID NO:89,
a heavy chain CDR2 comprising the amino acid sequence of SEQ ID NO:90, and
a heavy chain CDR3 comprising the amino acid sequence of SEQ ID NO:91; and
(l) a light chain variable region comprising
a light chain CDR1 comprising the amino acid sequence of SEQ ID NO:92,
a light chain CDR2 comprising the amino acid sequence of SEQ ID NO:73, and
a light chain CDR3 comprising the amino acid sequence of SEQ ID NO:74; or
(m) a heavy chain variable region comprising
a heavy chain CDR1 comprising the amino acid sequence of SEQ ID NO:93,
a heavy chain CDR2 comprising the amino acid sequence of SEQ ID NO:94, and
a heavy chain CDR3 comprising the amino acid sequence of SEQ ID NO:95; and
(n) a light chain variable region comprising
a light chain CDR1 comprising the amino acid sequence of SEQ ID NO:96,
a light chain CDR2 comprising the amino acid sequence of SEQ ID NO:97, and
a light chain CDR3 comprising the amino acid sequence of SEQ ID NO:74.

In some embodiments, the heavy chain variable region of the antibodies disclosed herein comprises the amino acid sequence of SEQ ID NO:1 or 5. In some embodiments, the light chain variable region of the antibodies disclosed herein comprises the amino acid sequence of SEQ ID NO:3 or 7. In some embodiments, the heavy chain variable region of the antibodies disclosed herein comprises the amino acid sequence of SEQ ID NO:31, 35, 39, 43, 47, 51, or 55. In some embodiments, the light chain variable region of the antibodies disclosed herein comprises the amino acid sequence of SEQ ID NO:33, 37, 41, 45, 49, 53, or 57. In some embodiments, the heavy chain variable region of the antibodies disclosed herein comprises the amino acid sequence of SEQ ID NO:1, 5, 31, 35, 39, 43, 47, 51, or 55 and the light chain variable region of the antibodies disclosed herein comprises the amino acid sequence of SEQ ID NO:3, 7, 33, 37, 41, 45, 49, 53, or 57, respectively.

In other embodiments, the antibodies comprise a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:1 or 5. In other embodiments, the antibodies comprise a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:31, 35, 39, 43, 47, 51, or 55.

In some embodiments, the antibodies comprise a light chain variable region comprising an amino acid sequence having at least 80%, at least 85%, at least 90%, at least 93%, at least 95%, at least 96%, at least 97%, at least 98%, at least 99%, or 100% identity to SEQ ID NO:3 or 7. In some embodiments, the antibodies comprise a light chain variable region comprising an amino acid sequence having at least 80%, at least 85%, at least 90%, at least 93%, at least 95%, at least 96%, at least 97%, at least 98%, at least 99%, or 100% identity to SEQ ID NO:3, 7, 33, 37, 41, 45, 49, 53, or 57.

In some embodiments, the antibodies comprise a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:1, 5, 31, 35, 39, 43, 47, 51, or 55 and a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:3, 7, 33, 37, 41, 45, 49, 53, or 57, respectively.

The antibodies can further comprise heavy and/or light chain constant regions. In some embodiments, the heavy chain constant region is selected from the group consisting of human immunoglobulins $IgG_1$, $IgG_2$, $IgG_3$, and $IgG_4$. In some embodiments, the heavy chain constant region comprises an amino acid sequence of SEQ ID NO:9. In some embodiments, the heavy chain constant region comprises an amino acid sequence of SEQ ID NO:61.

In some embodiments, the light chain constant region is selected from the group consisting of human immunoglobulins IgGκ and IgGλ. In some embodiments, the light chain constant region comprises an amino acid sequence of SEQ ID NO:10. In some embodiments, the light chain constant region comprises an amino acid sequence of SEQ ID NO:62.

In some embodiments, the antibodies comprise a heavy chain constant region comprising an amino acid sequence having at least 80%, at least 85%, at least 90%, at least 93%, at least 95%, at least 96%, at least 97%, at least 98%, at least 99%, or 100% identity to SEQ ID NO:9 or 61 and a light chain constant region comprising an amino acid sequence having at least 80%, at least 85%, at least 90%, at least 93%, at least 95%, at least 96%, at least 97%, at least 98%, at least 99%, or 100% identity to SEQ ID NO:10 or 62, respectively or in any combination thereof.

The antibodies can be a human antibody. The antibodies can be a single chain antibody (scFv), Fab, or dsFV.

Disclosed herein are monoclonal antibodies that bind to the same epitope of human SH3 domain-containing YSC84-like 1 (SH3YL1) as the antibodies disclosed herein.

Disclosed herein are monoclonal antibodies that specifically bind to human SH3 domain-containing YSC84-like 1 (SH3YL1) at an epitope comprising the amino acid sequence DSHFDWWE (SEQ ID NO:25).

Also disclosed herein are monoclonal antibodies that specifically bind to human SH3 domain-containing YSC84-like 1 (SH3YL1) at an epitope comprising the amino acid sequence LYEILDSF (SEQ ID NO:26).

Also disclosed are monoclonal antibodies that specifically bind to human SH3 domain-containing YSC84-like 1 (SH3YL1) at an epitope comprising the amino acid sequence of SEQ ID NO:98, 99, 100, or 60.

In some embodiments, the amino acid sequence of SH3YL1 is provided in SEQ ID NO:11 and the nucleotide sequence of SH3YL1 is provided in SEQ ID NO:12.

As used herein, the terms "antibody" and "antibodies" are terms of art and can be used interchangeably herein and refer to a molecule with an antigen-binding site that specifically binds an antigen. Antibodies can include, for example, monoclonal antibodies, which include recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), (scFv)2, sc(Fv)2, camelized antibodies, affybodies, Fab fragments, Fv, $F(ab')_2$ fragments, disulfide-linked Fvs (dsFv), anti-idiotypic (anti-Id) antibodies (including, e.g., anti-anti-Id antibodies), bispecific antibodies, multispecific antibodies, minibodies, triabodies, tetrabodies, or antibody-drug conjugates.

Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$, $IgG_2$, or $IgG_4$) or subclass thereof. In some embodiments, the antibody is a humanized monoclonal antibody. In other embodiments, the antibody is a human monoclonal antibody, e.g., that is an immunoglobulin.

As used herein, the terms "antigen-binding domain," "antigen-binding region," "antigen-binding site," and similar terms refer to the portion of the antibodies that comprise the amino acid residues that confer on the antibody molecule its specificity for the antigen (e.g., the complementarity determining regions (CDR)). The antigen-binding region can be derived from any animal species, such as rodents (e.g., mouse, rat, or hamster) and humans.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190:382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In some embodiments, the CDRs of the antibodies described herein have been determined according to the Kabat numbering scheme.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to an antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\varepsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50(Pt 4):339-350; McPherson A (1990) Eur J Biochem 189:1-23; Chayen N E (1997) Structure 5:1269-1274; McPherson A (1976) J Biol Chem 251:6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1):37-60; Bricogne G (1997) Meth Enzymol 276A: 361-423, ed Carter C W; Roversi P et al., (2000) Acta Crystallogr D Biol Crystallogr 56(Pt 10):1316-1323). Mutagenesis mapping studies can be accomplished using any method known to one of skill in the art. See, e.g., Champe M et al., (1995) J Biol Chem 270:1388-1394 and Cunningham B C & Wells J A (1989) Science 244:1081-1085 for a description of mutagenesis techniques, including alanine scanning mutagenesis techniques. In some embodiments, the epitope of an antibody is determined using alanine scanning mutagenesis studies.

As used herein, the terms "immunospecifically binds," "immunospecifically recognizes," "specifically binds," and "specifically recognizes" are analogous terms in the context of antibodies and refer to molecules that bind to an antigen (e.g., epitope, immune complex, or binding partner of an antigen-binding site) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In some embodiments, molecules that immunospecifically bind to an antigen bind to the antigen with a K A that is at least 2 logs, 2.5 logs, 3 logs, 4 logs or greater than the K A when the molecules bind to another antigen.

In other embodiments, molecules that immunospecifically bind to an antigen do not cross react with other proteins under similar binding conditions. In some embodiments, molecules that immunospecifically bind to an antigen do not cross react with other proteins. In some embodiments, provided herein is an antibody that binds to a specified antigen with higher affinity than to another unrelated antigen. In certain embodiments, provided herein is an antibody that binds to a specified antigen (e.g., human SH3YL1) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In some embodiments, the extent of binding of an antibody described herein to an unrelated, protein is less than 10%, 15%, or 20% of the binding of the antibody to the specified antigen as measured by, e.g., a radioimmunoassay.

In some embodiments, provided herein are monoclonal antibodies that bind to a human antigen with higher affinity than to another species of the antigen. In certain embodiments, provided herein are monoclonal antibodies that bind to a human antigen (e.g., human SH3YL1) with a 5%, 10%, 15%, 20%, 25%, 30%, 35%, 40%, 45%, 50%, 55%, 60%, 65%, 70% or higher affinity than to another species as measured by, e.g., a radioimmunoassay, surface plasmon resonance, or kinetic exclusion assay. In some embodiments, the antibodies described herein, which bind to a human antigen (e.g., human SH3YL1), will bind to another species of the antigen protein with less than 10%, 15%, or 20% of the binding of the antibody to the human antigen protein as measured by, e.g., a radioimmunoassay, surface plasmon resonance, or kinetic exclusion assay.

In certain aspects, an antibody described herein can be described by its VL domain alone, or its VH domain alone, or by its 3 VL CDRs alone, or its 3 VH CDRs alone. See, for example, Rader C et al., (1998) PNAS 95:8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. See also Kim S J & Hong H J, (2007) J Microbiol 45:572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody can be determined according to the Chothia numbering scheme, which refers to the location of immunoglobulin structural loops (see, e.g., Chothia C & Lesk A M, (1987), J Mol Biol 196:901-917; Al-Lazikani B et al., (1997) J Mol Biol 273:927-948; Chothia C et al., (1992) J Mol Biol 227:799-817; Tramontano A et al., (1990) J Mol Biol 215(1):175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are monoclonal antibodies that specifically bind to SH3YL1 and comprise the Chothia VL CDRs of a VL. In certain aspects, provided herein are monoclonal antibodies that specifically bind to SH3YL1 (e.g., human SH3YL1) and comprise the Chothia VH CDRs of a VH. In certain aspects, provided herein are monoclonal antibodies that specifically bind to SH3YL1 (e.g., human SH3YL1) and comprise the Chothia VL CDRs of a VL and comprise the Chothia VH CDRs of a VH. In certain embodiments, monoclonal antibodies that specifically bind to SH3YL1 (e.g., human SH3YL1) comprise one or more CDRs, in which the Chothia and Kabat CDRs have the same amino acid sequence. In certain embodiments, provided herein are monoclonal antibodies that specifically bind to SH3YL1 (e.g., human SH3YL1) and comprise combinations of Kabat CDRs and Chothia CDRs.

In certain aspects, the CDRs of an antibody can be determined according to the IMGT numbering system as described in Lefranc M-P, (1999) The Immunologist 7:132-136 and Lefranc M-P et al., (1999) Nucleic Acids Res 27:209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

In certain aspects, the CDRs of an antibody can be determined according to MacCallum R M et al., (1996) J Mol Biol 262:732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001).

In certain aspects, the CDRs of an antibody can be determined according to the AbM numbering scheme, which refers AbM hypervariable regions which represent a compromise between the Kabat CDRs and Chothia structural loops and are used by Oxford Molecular's AbM antibody modeling software (Oxford Molecular Group, Inc.).

In some embodiments, the position of one or more CDRs along the VH (e.g., CDR1, CDR2, or CDR3) and/or VL (e.g., CDR1, CDR2, or CDR3) region of an antibody described herein can vary by one, two, three, four, five, or six amino acid positions so long as immunospecific binding to an antigen is maintained (e.g., substantially maintained, for example, at least 50%, at least 60%, at least 70%, at least 80%, at least 90%, at least 95%). For example, the position defining a CDR of an antibody described herein can vary by shifting the N-terminal and/or C-terminal boundary of the CDR by one, two, three, four, five, or six amino acids, relative to the CDR position of an antibody described herein, so long as immunospecific binding to the antigen(s) is maintained (e.g., substantially maintained, for example, at least 50%, at least 60%, at least 70%, at least 80%, at least 90%, at least 95%). In other embodiments, the length of one or more CDRs along the VH (e.g., CDR1, CDR2, or CDR3) and/or VL (e.g., CDR1, CDR2, or CDR3) region of an antibody described herein can vary (e.g., be shorter or longer) by one, two, three, four, five, or more amino acids, so long as immunospecific binding to the antigen(s) is maintained (e.g., substantially maintained, for example, at least 50%, at least 60%, at least 70%, at least 80%, at least 90%, at least 95%).

In some embodiments, a VL CDR1, VL CDR2, VL CDR3, VH CDR1, VH CDR2, and/or VH CDR3 described herein can be one, two, three, four, five or more amino acids shorter than one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, a VL CDR1, VL CDR2, VL CDR3, VH CDR1, VH CDR2, and/or VH CDR3 described herein can be one, two, three, four, five or more amino acids longer than one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the amino terminus of a VL CDR1, VL CDR2, VL CDR3, VH CDR1, VH CDR2, and/or VH CDR3 described herein can be extended by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the carboxy terminus of a VL CDR1, VL CDR2, VL CDR3, VH CDR1, VH CDR2, and/or VH CDR3 described herein can be extended by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the amino terminus of a VL CDR1, VL CDR2, VL CDR3, VH CDR1, VH CDR2, and/or VH CDR3 described herein can be shortened by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In some embodiments, the carboxy terminus of a VL CDR1, VL CDR2, VL CDR3, VH CDR1, VH CDR2, and/or VH CDR3 described herein can be shortened by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). Any method known in the art can be used to ascertain whether immunospecific binding to the antigen(s) is maintained, for example, the binding assays and conditions described in the "Examples" section herein.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87:2264-2268, modified as in Karlin S & Altschul S F (1993) PNAS 90:5873-5877. Such an algorithm is incorporated into the NBLAST and XBLAST programs of Altschul S F et al., (1990) J Mol Biol 215:403. BLAST nucleotide searches can be performed with the NBLAST nucleotide program parameters set, e.g., for score=100, wordlength=12 to obtain nucleotide sequences homologous to nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, nonlimiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, an "isolated" antibody is one which is separated from other antibodies that are present in the natural source (e.g., in a mouse or a human) of the antibody. Moreover, an "isolated" antibody can be substantially free of other cellular material, or culture medium when produced by recombinant techniques, or substantially free of chemical precursors or other chemicals when chemically synthesized. For example, the language "substantially free" includes preparations of antibodies having less than about 15%, 10%, 5%, 2%, 1%, 0.5%, or 0.1% (in particular less than about 10%) of other material, e.g., cellular material, culture medium, other antibodies, chemical precursors and/or other chemicals.

An antibody can be fused or conjugated (e.g., covalently or noncovalently linked) to a detectable label or substance. Examples of detectable labels or substances include enzyme labels, such as, glucose oxidase; radioisotopes, such as iodine ($^{125}$I, $^{121}$I, carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labeled antibodies can be used to detect antigen proteins.

Antibody Production

The antibodies disclosed herein can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al. L Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In some embodiments, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In some aspects, provided herein is a method of making an antibody disclosed herein comprising culturing a cell or host cell described herein. In some aspects, provided herein is a method of making an antibody comprising expressing (e.g., recombinantly expressing) the antibody using a cell or host cell described herein (e.g., a cell or a host cell comprising polynucleotides encoding an antibody described herein). In some embodiments, the cell is an isolated cell. In some embodiments, the exogenous polynucleotides have been introduced into the cell. In some embodiments, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein.

A "monoclonal antibody," as used herein, is an antibody produced by a single cell (e.g., hybridoma or host cell producing a recombinant antibody), wherein the antibody immunospecifically binds to an antigen (e.g., human SH3YL1) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody can be a Fab fragment or a F(ab') 2 fragment. Monoclonal antibodies described herein can, for example, be made by the hybridoma method as described in Kohler G & Milstein C (1975) Nature 256:495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the antigen (e.g., human SH3YL1)) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., human SH3YL1)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that can contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133:3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against an antigen. The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein can be generated by any technique known to those of skill in the art. For example, Fab and $F(ab')_2$ fragments can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of a tetrameric antibody molecule and contains the complete light chain paired with the VH and CH1 domains of the heavy chain. A $F(ab')_2$ fragment contains the two antigen-binding arms of a tetrameric antibody molecule linked by disulfide bonds in the hinge region.

Further, the antibodies described herein can also be generated using various phage display methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182:41-50; Ames R S et al., (1995) J Immunol Methods 184:177-186; Kettleborough C A et al., (1994) Eur J Immunol 24:952-958; Persic L et al., (1997) Gene 187:9-18; Burton D R & Barbas C F (1994) Advan Immunol 57:191-280; PCT/GB91/001134; WO90/02809, WO91/10737, WO92/01047, WO92/18619, WO93/11236, WO95/15982, WO95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate antibodies, including human antibodies, and expressed in any desired host, including mammalian cells, insect cells, plant cells, yeast, and bacteria, e.g., as described below. Techniques to recombinantly produce antibodies such as Fab, Fab' and $F(ab')_2$ fragments can also be employed using methods known in the art such as those disclosed in WO92/22324; Mullinax R L et al., (1992) BioTechniques 12(6):864-9; Sawai H et al., (1995) Am J Reprod Immunol 34:26-34; and Better M et al., (1988) Science 240:1041-1043.

In some aspects, to generate antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229:1202-7; Oi V T & Morrison S L (1986) BioTechniques 4:214-221; Gillies S D et al., (1989) J Immunol Methods 125:191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (EP 239400; WO91/09967; and U.S. Pat. Nos. 5,225,539, 5,530,101, and 5,585,089), veneering or resurfacing (EP 592106 and EP 519596; Padlan E A (1991) Mol Immunol 28(4/5):489-498; Studnicka G M et al., (1994) Prot Engineering 7(6):805-814; and Roguska M A et al., (1994) PNAS 91:969-973), chain shuffling (U.S. Pat. No. 5,565,332), and techniques disclosed in, e.g., U.S. Pat. Nos. 6,407,213, 5,766,886, WO93/17105; Tan P et al., (2002) J Immunol 169:1119-25; Caldas C et al., (2000) Protein Eng. 13(5):353-60; Morea V et al., (2000) Methods 20(3):267-79; Baca M et al., (1997) J Biol Chem 272(16):10678-84; Roguska M A et al., (1996) Protein Eng 9(10):895 904; Couto J R et al., (1995) Cancer Res. 55 (23 Supp):5973s-5977s; Couto J R et al., (1995) Cancer Res 55(8):1717-22; Sandhu J S (1994) Gene 150(2):409-10 and Pedersen J T et al., (1994) J Mol Biol 235(3):959-73. See also US 2005/0042664 A1 (Feb. 24, 2005), which is incorporated by reference herein in its entirety.

Single domain antibodies, for example, antibodies lacking the light chains, can be produced by methods well known in the art. See Riechmann L & Muyldermans S (1999) J Immunol 231:25-38; Nuttall S D et al., (2000) Curr Pharm Biotechnol 1(3):253-263; Muyldermans S, (2001) J Biotechnol 74(4):277-302; U.S. Pat. No. 6,005,079; and WO94/04678, WO94/25591 and WO01/44301.

Further, antibodies that immunospecifically bind to an antigen can, in turn, be utilized to generate anti-idiotype antibodies that "mimic" an antigen using techniques well known to those skilled in the art. See, e.g., Greenspan N S & Bona C A (1989) FASEB J 7(5):437-444; and Nissinoff A (1991) J Immunol 147(8):2429-2438.

In particular embodiments, an antibody described herein, which binds to the same epitope of an antigen of interest (e.g., human SH3YL1) as an antibody described herein, is a human antibody. In particular embodiments, an antibody described herein, which competitively blocks (e.g., in a dose-dependent manner) any one of the antibodies described herein from binding to SH3YL1 (e.g., human SH3YL1), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., WO98/24893, WO96/34096 and WO96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to an antigen can be made by a variety of methods known in the art including phage display methods described above using antibody libraries derived from human immunoglobulin sequences. See also U.S. Pat. Nos. 4,444,887, 4,716,111, and 5,885,793; and WO98/46645, WO98/50433, WO98/24893, WO98/16654, WO96/34096, WO96/33735, and WO91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen. Such methods are known and are described in the art, see, e.g., Shinmoto H et al., (2004) Cytotechnology 46:19-23; Naganawa Y et al., (2005) Human Antibodies 14:27-31.

Polynucleotides, Vectors, and Cells

Disclosed herein are isolated nucleic acid molecules encoding the heavy chain variable region or heavy chain of the antibodies disclosed herein. Disclosed herein are isolated nucleic acid molecules encoding the light chain variable region or light chain of the antibodies disclosed herein.

Disclosed herein are isolated nucleic acid molecules encoding the heavy chain variable region or heavy chain of the antibodies disclosed herein and the light chain variable region or light chain of the antibodies disclosed herein.

Disclosed herein are isolated nucleic acid molecules further comprising nucleic acid molecules encoding a heavy chain variable region comprising the amino acid sequence of SEQ ID NO:1 or 5. Disclosed herein are isolated nucleic acid molecules further comprising nucleic acid molecules encoding a light chain variable region comprising the amino acid sequence of SEQ ID NO:3 or 7. In some embodiments, the nucleic acid molecule encodes a light chain variable region comprising the amino acid sequence of SEQ ID NO:3 or 7. In some embodiments, the nucleic acid molecule encodes a heavy chain variable region comprising the amino acid sequence of SEQ ID NO:31, 35, 39, 43, 47, 51, or 55. In some embodiments, the nucleic acid molecule encodes a light chain variable region comprising the amino acid sequence of SEQ ID NO:33, 37, 41, 45, 49, 53, or 57.

Also disclosed are isolated vectors comprising a nucleic acid molecule disclosed herein. Further disclosed are host cells comprising a nucleic acid molecule disclosed herein. In some embodiments, the host cell is *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, or human cell in tissue culture.

Disclosed herein are methods of producing antibodies that bind to human SH3YL1, comprising culturing a host cell disclosed herein so that a nucleic acid molecule disclosed herein is expressed and the antibody is produced.

In certain aspects, provided herein are polynucleotides comprising a nucleotide sequence encoding an antibody described herein or a fragment thereof (e.g., a variable light chain region and/or variable heavy chain region) that immunospecifically binds to an antigen, and vectors, e.g., vectors comprising such polynucleotides for recombinant expression in host cells (e.g., *E. coli* and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In some embodiments, a nucleic acid molecule(s) encoding an antibody described herein is isolated or purified.

In particular aspects, provided herein are polynucleotides comprising nucleotide sequences encoding antibodies, which immunospecifically bind to an antigen polypeptide (e.g., human SH3YL1) and comprises an amino acid sequence as described herein, as well as antibodies that compete with such antibodies for binding to an antigen polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein. The polynucleotides can comprise nucleotide sequences encoding a heavy chain comprising the VH FRs and CDRs of antibodies described herein.

In specific embodiments, provided herein are polynucleotides comprising a nucleotide sequence encoding an antibody comprising a Fab comprising three VH chain CDRs, e.g., containing VL CDR1, VL CDR2, and VL CDR3 of an antibody to human SH3YL1 described herein and three VH chain CDRs, e.g., containing VH CDR1, VH CDR2, and VH CDR3 of an antibody to human SH3YL1 described herein.

In particular embodiments, provided herein are polynucleotides comprising a nucleotide sequence encoding an antibody or a fragment thereof comprising a VL domain.

In certain embodiments, a polynucleotide described herein comprises a nucleotide sequence encoding an antibody provided herein comprising a light chain variable region comprising an amino acid sequence described herein (e.g., SEQ ID NO:3 or 7), wherein the antibody immunospecifically binds to SH3YL1 (e.g., human SH3YL1).

In certain embodiments, a polynucleotide described herein comprises a nucleotide sequence encoding an antibody provided herein comprising a heavy chain variable region comprising an amino acid sequence described herein (e.g., SEQ ID NO:1 or 5), wherein the antibody immunospecifically binds to SH3YL1 (e.g., human SH3YL1).

In specific aspects, provided herein is a polynucleotide comprising a nucleotide sequence encoding an antibody comprising a light chain and a heavy chain, e.g., a separate light chain and heavy chain. With respect to the light chain, in some embodiments, a polynucleotide provided herein comprises a nucleotide sequence encoding a kappa light chain. In other embodiments, a polynucleotide provided herein comprises a nucleotide sequence encoding a lambda light chain. In yet other embodiments, a polynucleotide provided herein comprises a nucleotide sequence encoding an antibody described herein comprising a human kappa light chain or a human lambda light chain. In some embodiments, a polynucleotide provided herein comprises a nucleotide sequence encoding an antibody, which immunospecifically binds to SH3YL1 (e.g., human SH3YL1), wherein the antibody comprises a light chain, and wherein the amino acid sequence of the VL domain can comprise the amino acid sequence set forth in SEQ ID NO:3 or 7 and wherein the constant region of the light chain comprises the amino acid sequence of a human kappa light chain constant region. For example, human constant region sequences can be those described in U.S. Pat. No. 5,693,780.

Also provided herein are polynucleotides encoding an antibody or a fragment thereof that are optimized, e.g., by codon/RNA optimization, replacement with heterologous signal sequences, and elimination of mRNA instability elements. Methods to generate optimized nucleic acids encoding an antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an antibody described herein or a fragment thereof (e.g., VL domain or VH domain) can hybridize to an antisense (e.g., complementary) polynucleotide of an unoptimized polynucleotide sequence encoding an antibody described herein or a fragment thereof (e.g., VL domain or VH domain). In specific embodiments, an optimized nucleotide sequence encoding an antibody described herein or a fragment hybridizes under high stringency conditions to antisense polynucleotide of an unoptimized polynucleotide sequence encoding an antibody described herein or a fragment thereof. In some embodiments, an optimized nucleotide sequence encoding an antibody described herein or a fragment thereof hybridizes under high stringency, intermediate or lower stringency hybridization conditions to an antisense polynucleotide of an unoptimized nucleotide sequence encoding an antibody described herein or a fragment thereof. Information regarding hybridization conditions has been described, see, e.g., US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17:242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, such as poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding antibodies described herein can be readily isolated and sequenced using conventional procedures (e.g., by using oligonucleotide probes that are capable of binding specifically to genes encoding the heavy and light chains of the antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of antibodies in the recombinant host cells.

To generate antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

In other embodiments, the isolated nucleic acid molecule comprises a nucleic acid sequence having at least 80%, at least 85%, at least 90%, at least 93%, at least 95%, at least 96%, at least 97%, at least 98%, at least 99%, or 100% identity to SEQ ID NO:2 or 6. In some embodiments, the nucleic acid molecule comprises a nucleic acid sequence having at least 80%, at least 85%, at least 90%, at least 93%, at least 95%, at least 96%, at least 97%, at least 98%, at least 99%, or 100% identity to SEQ ID NO:4 or 8. In other embodiments, the isolated nucleic acid molecule comprises a nucleic acid sequence having at least 80%, at least 85%, at least 90%, at least 93%, at least 95%, at least 96%, at least 97%, at least 98%, at least 99%, or 100% identity to SEQ ID NO:32, 36, 40, 44, 48, 52, or 56. In some embodiments, the nucleic acid molecule comprises a nucleic acid sequence having at least 80%, at least 85%, at least 90%, at least 93%, at least 95%, at least 96%, at least 97%, at least 98%, at least 99%, or 100% identity to SEQ ID NO:34, 38, 42, 46, 50, 54, or 58.

In some embodiments, the nucleic acid molecule encodes a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:1 and/or a light chain variable region comprising an amino acid sequence having at least 80%, at least 85%, at least 90%, at least 93%, at least 95%, at least 96%, at least 97%, at least 98%, at least 99%, or 100% identity to SEQ ID NO:3. In some embodiments, the nucleic acid molecule encodes a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:5 and/or a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:7. In some embodiments, the nucleic acid molecule encodes a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:1, 5, 31, 35, 39, 43, 47, 51, or 55 and/or a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:3, 7, 33, 37, 41, 45, 49, 53, or 57, respectively or in any combination thereof.

As used herein, the term "host cell" can be any type of cell, e.g., a primary cell, a cell in culture, or a cell from a cell line. In embodiments, the term "host cell" refers to a cell transfected with a nucleic acid molecule and the progeny or potential progeny of such a cell. Progeny of such a cell cannot be identical to the parent cell transfected with the nucleic acid molecule, e.g., due to mutations or environmental influences that can occur in succeeding generations or integration of the nucleic acid molecule into the host cell genome.

In certain aspects, provided herein are cells (e.g., host cells) expressing (e.g., recombinantly) the antibodies described herein which specifically bind to SH3YL1 (e.g., human SH3YL1) and related polynucleotides and expression vectors. Provided herein are vectors (e.g., expression vectors) comprising polynucleotides comprising nucleotide sequences encoding the antibodies or a fragment for recombinant expression in host cells, such as mammalian cells. Also provided herein are host cells comprising such vectors for recombinantly expressing the antibodies described herein (e.g., human or humanized antibody). Also provided herein are methods for producing an antibody described herein, comprising expressing such antibody in a host cell.

Recombinant expression of an antibody or fragment thereof described herein (e.g., a heavy or light chain of an antibody described herein) that specifically binds to involves construction of an expression vector containing a polynucleotide that encodes the antibody or fragment. Once a polynucleotide encoding an antibody or fragment thereof (e.g., heavy or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., WO86/05807 and WO89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein.

A variety of host-expression vector systems can be utilized to express antibody molecules described. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some embodiments, cells for expressing antibodies described herein (e.g., an antibody comprising the CDRs of any one of antibodies pab1949 or pab2044) are CHO cells, for example CHO cells from the CHO GS System™ (Lonza). In some embodiments, cells for expressing antibodies described herein are human cells, e.g., human cell lines. In some embodiments, a mammalian expression vector is pOptiVEC™ or pcDNA3.3. In some embodiments, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45:101-105; and Cockett M I et al., (1990) Biotechnology 8:662-667). In certain embodiments, antibodies described herein are produced by CHO cells or NS0 cells. In some embodiments, the expression of nucleotide sequences encoding antibodies described herein is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2:1791-1794), in which the antibody coding sequence can be ligated individually into the vector in frame with the lac Z coding region so that a fusion protein is produced; pIN vectors (Inouye S & Inouye M (1985) Nuc Acids Res 13:3101-3109; Van Heeke G & Schuster S M (1989) J Biol Chem 24:5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region El or E3) will result in a recombinant virus that is viable and capable of expressing the antibody molecule in infected hosts (e.g., see Logan J & Shenk T (1984) PNAS 81:3655-3659). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol 153:516-544).

In addition, a host cell strain can be chosen which modulates the expression of the inserted sequences or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS 1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, the antibodies described herein (e.g., an antibody comprising the CDRs are produced in mammalian cells, such as CHO cells.

In some embodiments, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express antibodies can be engineered. In specific embodiments, a cell provided herein stably expresses a light chain/light chain variable domain and a heavy chain/heavy chain variable domain which associate to form an antibody described herein (e.g., an antibody comprising the CDRs).

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) Cell 11(1):223-232), hypoxanthine-guanine phosphoribosyltransferase (Szybalska E H & Szybalski W (1962) PNAS 48(12):2026-2034) and adenine phosphoribosyltransferase (Lowy I et al., (1980) Cell 22(3): 817-823) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6):3567-3570; O'Hare K et al., (1981) PNAS 78:1527-1531); gpt, which confers resistance to mycophenolic acid (Mulligan R C & Berg P (1981) PNAS 78(4): 2072-2076); neo, which confers resistance to the aminoglycoside G-418 (Wu G Y & Wu C H (1991) Biotherapy 3:87-95; Tolstoshev P (1993) Ann Rev Pharmacol Toxicol 32:573-596; Mulligan R C (1993) Science 260:926-932; and Morgan R A & Anderson W F (1993) Ann Rev Biochem 62:191-217; Nabel G J & Felgner P L (1993) Trends Biotechnol 11(5):211-215); and hygro, which confers resistance to hygromycin (Santerre R F et al., (1984) Gene 30(1-3):147-156). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150:1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3:257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322:562-565; and Köhler G (1980) PNAS 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

The vector can comprise a nucleic acid molecule encoding an antigen binding fragment (Fab) that binds to SH3YL1.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, a monoclonal antibody described herein is isolated or purified. Generally, an isolated antibody is one that is substantially free of other antibodies with different antigenic specificities than the isolated antibody. For example, in some embodiments, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the antibody or fragment is recombinantly produced, it is also generally substantially free of culture medium, i.e., culture medium represents less than about 20%, 10%, 2%, 1%, 0.5%, or 0.1% of the volume of the protein preparation. When the antibody or fragment is produced by chemical synthesis, it is generally substantially free of chemical precursors or other chemicals, i.e., it is separated from chemical precursors or other chemicals which are involved in the synthesis of the protein. Accordingly, such preparations of the antibody or fragment have less than about 30%, 20%, 10%, or 5% (by dry weight) of chemical precursors or compounds other than the antibody or fragment of interest. In some embodiments, antibodies described herein are isolated or purified.

Compositions

Provided herein are compositions comprising an antibody described herein having the desired degree of purity in a physiologically acceptable carrier, excipient or stabilizer (Remington's Pharmaceutical Sciences (1990) Mack Publishing Co., Easton, PA). Also disclosed herein are pharmaceutical compositions comprising an antibody described herein and a pharmaceutically acceptable excipient. Acceptable carriers, excipients, or stabilizers are nontoxic to recipients at the dosages and concentrations employed.

The pharmaceutical composition of the present disclosure can provide rapid, sustained or delayed release of an active ingredient after being administered to a subject and can be formulated using a method well known to those skilled in the art. The formulations can be in the form of a tablet, pill, powder, sachet, elixir, suspension, emulsion, solution, syrup, aerosol, soft or hard gelatin capsule, sterile injectable solution, sterile powder, or the like. Examples of suitable carriers, excipients, and diluents are lactose, dextrose, sucrose, sorbitol, mannitol, xylitol, erythritol, maltitol, starches, gum acacia, alginate, gelatin, calcium phosphate, calcium silicate, cellulose, microcrystalline cellulose, polyvinyl pyrrolidone, water, methylhydroxybenzoate, propylhydroxybenzoate, talc, magnesium stearate and mineral oil. Further, the formulations can additionally include a filler, an anti-agglutinating agent, a lubricating agent, a wetting agent, a favoring agent, an emulsifier, a preservative, and the like.

Pharmaceutical compositions described herein can be useful in enhancing, inducing, or activating the activities of antibodies and treating a disease or condition, such as autoimmune conditions or diseases.

In some embodiments, the composition comprises the antibody and an excipient such as, e.g., PBS or water. In some embodiments, the composition is suitable for injection, such as by, e.g., intraperitoneal or intravenous injection. In some embodiments, the composition comprising the antibody can be administered in an amount of 0.1 mg/kg to 100 mg/kg, 0.1 mg/kg to 50 mg/kg, 1 mg/kg to 50 mg/kg, 5 mg/kg to 25 mg/kg, 10 mg/kg to 20 mg/kg body weight per week, or any ranges therein.

The compositions to be used for in vivo administration can be sterile. This is readily accomplished by filtration through, e.g., sterile filtration membranes.

Uses and Methods

Disclosed herein are methods of modulating an immune response in a subject, e.g., a subject in need thereof, the method comprising administering to the subject an effective amount of an antibody disclosed herein, a nucleic acid molecule disclosed herein, a vector disclosed herein, or a host cell disclosed herein, or a pharmaceutical composition disclosed herein. In some embodiments, the methods enhance or induce an immune response of the subject.

Disclosed herein are methods of treating diabetic nephropathy in a subject, e.g., a subject in need thereof, the methods comprising administering to the subject an effective amount of an antibody disclosed herein, a nucleic acid molecule disclosed herein, a vector disclosed herein, or a host cell disclosed herein, or a pharmaceutical composition disclosed herein. Disclosed herein are methods of treating kidney fibrosis in a subject, e.g., a subject in need thereof, the methods comprising administering to the subject an effective amount of an antibody disclosed herein, a nucleic acid molecule disclosed herein, a vector disclosed herein, or a host cell disclosed herein, or a pharmaceutical composition disclosed herein. In some embodiments, the methods or antibodies disclosed herein reduce inflammation of the kidney in the subject. In some embodiments, the methods or antibodies disclosed herein can decrease albumin secretion in urine, decrease the ratio of albumin to creatinine, and/or reduce mesangial expansion. In some embodiments, the methods further comprise administering to the subject losartan.

Disclosed herein are methods of treating non-alcoholic steatosis hepatitis in a subject, e.g., a subject in need thereof, the method comprising administering to the subject an effective amount of an antibody disclosed herein, a nucleic acid molecule disclosed herein, a vector disclosed herein, or a host cell disclosed herein, or a pharmaceutical composition disclosed herein. Disclosed herein are methods of treating liver fibrosis in a subject, e.g., a subject in need thereof, the method comprising administering to the subject an effective amount of an antibody disclosed herein, a nucleic acid molecule disclosed herein, a vector disclosed herein, or a host cell disclosed herein, or a pharmaceutical composition disclosed herein. In some embodiments, the methods or antibodies disclosed here can reduce inflammation of the liver in the subject.

Acute kidney injury (AKI) is defined as a clinical syndrome characterized by the rapid loss of the kidney's excretory function and is typically diagnosed by the accumulation of end products of nitrogen metabolism (urea and creatinine) (1). It is an important complication in patients admitted to hospital (10%-15% of all hospitalisations) (2) and in patients in the intensive care unit (ICU) where its prevalence can sometimes exceed 50% (3, 4). AKI is classified according to the classification system known as Risk, Injury, Failure, Loss, and End Stage Renal Disease (RIFLE) as outlined in the Kidney Disease Global Initiative AKI Guidelines (5). The causes of AKI are traditionally considered to be dehydration, hemorrhagic shock, glomerulonephritis, and acute intoxication, and recently it is believed to be caused by other diseases as well (4). The kidneys are the major targets for the toxic effects of various chemical agents and thus drug-induced AKI is a frequent entity in clinical medicine. Cisplatin (cis-diamminedichlorolatinum (II), CDDP) is a widely used anticancer drug especially in solid malignant tumors (6-8). The use of cisplatin is often limited by a number of important side effects, including nephrotoxicity (7, 9). It is important to prevent cisplatin-induced AKI in order to improve the survival of cancer patients receiving cisplatin-based treatments.

Disclosed herein are methods of treating acute kidney injury in a subject, e.g., a subject in need thereof, the method comprising administering to the subject an effective amount of an antibody disclosed herein, a nucleic acid molecule disclosed herein, a vector disclosed herein, or a host cell disclosed herein, or a pharmaceutical composition disclosed herein. In some embodiments, the methods or antibodies disclosed herein can reduce kidney injury markers, suppress renal dysfunction, attenuate pro-inflammatory cytokine production, attenuate tubular cell damage, and/or protect against renal damage.

Inflammatory bowel disease (IBD) including ulcerative colitis (UC) and Crohn's disease (CD) is a chronic inflammatory disease characterized by loss of mucosal integrity, infiltration of immune cells, severe inflammation and bloody diarrhea (1-3). Anti-inflammatory agents including aminosalicylates and corticosteroids are conventional therapeutics for IBD. Recently, biologic therapies including monoclonal antibodies to tumor necrosis factor-α (TNF-α), interleukin (IL)-12/23, or integrins (1). Although biologic therapies reduced the risk of disease-related complications, including surgery and hospitalization, most of patients (up to 60% including recurrence) did not respond to the treatment. These clinical observations suggest a novel therapeutic target for the management of IBD.

Disclosed herein are methods of treating inflammatory bowel disease in a subject, e.g., a subject in need thereof, the method comprising administering to the subject an effective amount of an antibody disclosed herein, a nucleic acid molecule disclosed herein, a vector disclosed herein, or a host cell disclosed herein, or a pharmaceutical composition disclosed herein. In some embodiments, the methods or antibodies disclosed herein can inhibit reduction in mucosal layers.

Also disclosed herein are methods for treating kidney diseases, diabetic complications, non-alcoholic steatosis hepatitis, and/or liver fibrosis in a subject, e.g., a subject in need thereof, comprising administering to the subject a therapeutically effective amount of an antibody disclosed herein.

In some embodiments, the kidney disease is acute injury, ESKD, systemic lupus erythematosus, diabetic nephropathy (DN), diabetes mellitus nephropathy (DMN), IgA nephritis (IgAN), HIV-associated nephropathy, non-diabetic chronic kidney disease, focal segmental glomerulosclerosis (FSGS), minimal change nephrotic syndrome (MCD), or xanthine oxidase deficiency. In some embodiments, the diabetic complications are diabetic retinopathy, diabetic foot ulcer, or diabetic neuropathic pain.

As used herein, the terms "subject" and "patient" are used interchangeably. The subject can be in need of the treatment. The subject can be an animal. In some embodiments, the subject is a mammal such as a non-primate (e.g., cow, pig, horse, cat, dog, rat, etc.) or a primate (e.g., monkey or human), or a human. In some embodiments, the subject is a cynomolgus monkey. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

Disclosed herein are methods for detecting SH3YL1 in a sample, comprising contacting the sample with an antibody disclosed herein.

In some aspects, disclosed herein are methods for modulating one or more immune functions or responses in a subject, e.g., a subject in need thereof, comprising to a subject in need thereof administering an antibody described herein, or a composition thereof. Disclosed herein are methods for activating, enhancing or inducing one or more immune functions or responses in a subject, e.g., a subject in need thereof, comprising to a subject in need thereof administering an antibody or a composition thereof. In some embodiments, presented herein are methods for preventing and/or treating diseases in which it is desirable to activate or enhance one or more immune functions or responses, comprising administering to a subject in need thereof an antibody described herein or a composition thereof. In certain embodiments, presented herein are methods of treating an autoimmune disease or condition comprising administering to a subject in need thereof an antibody or a composition thereof.

In some embodiments, an antibody described herein activates or enhances or induces one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the antibody described herein using assays well known in the art, e.g., ELISPOT, ELISA, and cell proliferation assays.

Routes of Administration & Dosage

The pharmaceutical compositions of the present disclosure can be administered to a subject through a variety of administration routes including oral, transcutaneous, subcutaneous, intravenous, and intramuscular administration routes.

As used herein, the term "effective amount" in the context of the administration of a therapy to a subject refers to the amount of a therapy that achieves a desired prophylactic or therapeutic effect. The amount of an antibody or composition which will be effective in the treatment and/or prevention of a condition will depend on the nature of the disease and can be determined by standard clinical techniques.

In the present disclosure, the amount of the antibody actually administered is determined in light of various relevant factors including the disease to be treated, a selected route of administration, the age, sex and body weight of a patient, and severity of the disease, and the type of a bioactive polypeptide as an active ingredient. Since the antibody of the present disclosure has a very excellent sustainability in blood, the number and frequency of administration of the peptide preparations comprising the fusion protein of the present disclosure can be noticeably reduced.

The precise dose to be employed in a composition will also depend on the route of administration, and the seriousness of the disease, and should be decided according to the judgment of the practitioner and each subject's circumstances. For example, effective doses can also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses can be extrapolated from dose response curves derived from in vitro or animal model test systems.

Generally, human antibodies have a longer half-life within the human body than antibodies from other species due to the immune response to the foreign polypeptides. Thus, lower dosages of human antibodies and less frequent administration is often possible In some embodiments, the composition is suitable for injection, such as by, e.g., intraperitoneal or intravenous injection. In some embodiments, the composition comprising the antibody can be administered in an amount of 0.1 mg/kg to 100 mg/kg, 0.1 mg/kg to 50 mg/kg, 1 mg/kg to 50 mg/kg, 5 mg/kg to 25 mg/kg, 10 mg/kg to 20 mg/kg of body weight of the subject per week, or any ranges therein. In some embodiments, the composition comprises an antibody disclosed herein and PBS, suitable for administration to a subject in need there of in an amount of 10 mg/kg of body weight per week.

Kits

Provided herein are kits comprising one or more antibodies described herein or conjugates thereof. Disclosed herein are kits comprising an antibody disclosed herein, a nucleic acid molecule disclosed herein, a vector disclosed herein, or a host cell disclosed herein, or a pharmaceutical composition disclosed herein, and (a) a detection reagent, (b) an SH3YL1 antigen, (c) a notice that reflects approval for use or sale for human administration, or d) a combination thereof.

In some embodiments, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. Optionally associated with such container(s) can be a notice in the form prescribed by a governmental agency regulating the manufacture, use or sale of pharmaceuticals or biological products, which notice reflects approval by the agency of manufacture, use or sale for human administration. Also provided herein are kits that can be used in the above methods. In some embodiments, a kit comprises an antibody described herein, e.g., a purified antibody, in one or more containers. In some embodiments, kits described herein contain a substantially isolated antigen(s) (e.g., human SH3YL1) that can be used as a control. In other embodiments, the kits described herein further comprise a control antibody which does not react with a SH3YL1 antigen. In other embodiments, kits described herein contain one or more elements for detecting the binding of an antibody to a SH3YL1 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized SH3YL1 antigen. The SH3YL1 antigen provided in the kit can also be attached to a solid support. In some embodiments, the detecting means of the above-described kit includes a solid support to which a SH3YL1 antigen is attached. Such a kit can also include a non-attached reporter-labeled anti-human antibody or anti-mouse/rat antibody. In binding of the antibody to the SH3YL1 antigen can be detected by binding of the said reporter-labeled antibody.

Hereinafter, the present disclosure will be described with reference to several embodiments and the accompanying drawings. The following embodiments and drawings are provided for illustration purpose only and not for the purpose of limiting the present disclosure as defined by the appended claims.

EXAMPLES

Example 1. Anti-SH3YL1 Monoclonal Antibodies and Diabetic Nephropathy

Example 1.1. Materials and Methods

Preparation of Murine Mesangial Cells (MMCs)

Kidneys were isolated from the mouse and maintained in the PBS containing 1% penicillin and streptomycin (Gibco). Glomeruli were collected from the 75 um and 63 um sieves by centrifugation at 1300 rpm for 3 minutes. Isolated glomeruli were plated onto culture dish and maintained at 37° C. under 5% $CO_2$ condition in low glucose Dulbecco's modified Eagle's medium (DMEM; Gibco) supplemented with 20% (v/v) fetal bovine serum (FBS; welgene) and 1% antibiotic-antimycotic solution (Welgene). Isolated glomeruli were left undisturbed until the glomerular mesangial cells spread out. The cells were then sub-cultured onto culture dish and used for the further experiments.

Mouse Mesangial Cell Line (MES13) Culture

Mouse mesangial cell line (MES13) were purchased from ATCC. The cells were grown at 37° C. under 5% $CO_2$ condition in low glucose DMEM (Gibco) supplemented with 5% FBS and 1% antibiotic-antimycotic solution (Welgene).

Animals

All procedures of animals were approved and performed by the Institutional Animal Care and Use Committes (IACUC) and ethical guidances at Ewha Womans University.

Six-week-old male diabetic db/db mice (BKS.Cg-Dock7$^{m}$+/+Lepr$^{db}$/J) were purchased from the Jackson Laboratory (Bar Harbor, ME, USA). To investigate the effect of SH3YL1 antibodies (CRB-A4, CRB-E10). The db/m and db/db mice (8-week-old) were divided into four groups: (1) control db/m mice (n=5), (2) control db/db mice treated with vehicle (n=5), (3) db/db mice treated with CRB-A4 (n=5), and (4) db/db mice treated with CRB-E10 (n=5). Antibodies were injected intraperitoneally at a dose of 10 mg/kg per week for 12 weeks. Body weight, blood glucose level, Urine volume were measured every 4 weeks. Blood glucose level was measured using glucometer (Accucheck; Roche, Basel, Switzerland). Mice were separated in metabolic cages individually for 24 hrs for the urine collection. After 12 weeks, mice were sacrificed and obtained serum by cardiac puncture for further analysis, and kidneys were dissected rapidly for paraffin/frozen section or protein/RNA analysis.

Measurements of Metabolic Parameters

The urinary albumin was measured using commercial ELISA (ALPCO, Westlake, OH, USA). Serum and urinary creatinine level were determined with enzymatic colorimetric assay (ARBOR ASSAYS, Ann Arbor, MI, USA). Albumin to creatinine ratio (ACR) was calculated using total albumin with urinary creatinine. To calculate creatinine clearance (CCR), the standard formula was used. Blood urea nitrogen (BUN) was measured with colorimetric assay kit (ARBOR ASSAYS, Ann Arbor, MI, USA).

MIP2 and KC ELISA pMMC were isolated and cultured in 35 mm plates ($5\times10^5$). pMMCs were serum starved for 4 hr and then incubated with Flagellin (100 ng/ml) or SH3YL1 (1 ug/ml) for 24 hrs, and then the medium was collected. MIP2 and KC protein levels were determined by ELISA assay kit according to the manufacturer's instruction (R&D systems, Minneapolis, MN, USA).

Measurement of Intracellular H2O2 by Peroxy Orange-1

The confluent cells were starved overnight with serum free medium. After the cell culture media was swapped out, cells were washed with Dulbecco's PBS and then cells were incubated with both SH3YL1(1 ug/ml) and 5um PO-1 in PBS at 37° C. for 10 min. After incubation, the cells were washed again with PBS and then examined with a laser scanning confocal microscope LSM 880 airyscan (Carl Zeiss vision system) at an excitation wavelength of 540 nm. Five groups of cells were randomly selected from each sample, relative fluorescence intensity was measured, and then averaged for each group. All experiments were repeated at least three times.

Library Panning

For panning of the library against target molecules, an immunotube (NUNC 470319, Thermo Fisher Scientific, Waltham, MA, USA) was coated with antigen (10 μg/mL in PBS). The tube was coated for 1 h at 37° C. and subsequently blocked by filling the tube with 3% skim milk in PBST (PBS with 0.05% Tween 20, pH 7.4) for 1 h at RT. The blocking solution was removed and the phage library was added to the antigen-coated immunotube. The tube was then incubated with shaking at 37° C. for 2 h, and the unbound phages were washed out three times with PBST. The bound phages were eluted with 1 mL of 100 mM TEA (triethanolamine) for 10 min at RT, and the eluted phage solution was neutralized with 500 μL of 1 M Tris-HCl (pH 7.4). The neutralized phages were applied to 8.5 mL mid-log phase ER2537 and incubated for 1 h at 37° C. with shaking at 120 rpm. Infected ER2537 cells were plated on ampicillin-LB agarose plate with 2% (w/v) glucose and grown overnight at 37° C. The next day, the bacteria were harvested and phage library was rescued. Identical panning steps were repeated three times for the enrichment of antibody specific to the target peptide (Kim, D. G. et al., *Biomolecules* 10:820 (2020)).

CHO Cell Culture and Transient Transfection

ExpiCHO expression system (gibco) was used for the expression of the antibodies. ExpiCHO-S cells were cultured in ExpiCHO Expression medium (Gibco) in a humidified 8% $CO_2$ at 37° C. and 125 rpm. The heavy and light chains were transiently transfected in a 1:2 ratio. Antibody transfections were performed using the ExpiCHO Expression System Kit (Gibco) according to the manufacturer's protocol (standard protocol).

Antibody Purification

IgG antibodies were purified using Protein G Sepharose® 4 FastFlow (GE Healthcare). Protein G sepharose were loaded on to poly-prep chromatography columns (Bio-rad) and then washed with endotoxin tested DPBS (Gibco). At the same time, transfected CHO cells were centrifuged twice at 3000 rpm for 5 min to obtain supernatant. Transiently transfected Cell supernatant loaded onto protein G bead column then allow the column to empty by gravity flow. Then the column was washed with PBS (Welgene). Following the wash step, antibodies were eluted with 100 mM glycine, pH 2.0. Following elution, the IgG was brought to neutral pH with 1M Tris-HCl, pH 8.0. Purified antibodies were then exchanged buffer with PBS using Amicon® Ultra Centrifugal Filter Devices (Millipore) and filtered using a 0.22 um centrifuge tube filter (Corning).

IgG Conversion

The clones selected through scFv library panning were converted to $IgG_1$. VH and VL genes were amplified by PCR and cloned to vector containing human IgG constant region genes. For VH region conversion, forward primer (5'-TTC TCC AGC GCT TAT TCC GAG GTG CAG CTG TTG GAG-3') (SEQ ID NO:27) and reverse primer (5'-CTT GGT GCT AGC TGA GCT CAC GGT GAC CAG-3') (SEQ ID NO:28) were used. For VL region conversion, forward primer (5'-TTC TCC AGC GCT TAT TCC CAG TCT GTG CTG ACT CAG-3') (SEQ ID NO:29) and reverse primer (5'-GGG CTG ACC TAG GAC CGT CAG CTT-3') (SEQ ID NO:30) were used.

Epitope Mapping

Customized peptide microarray (Axxelera) has been used for the identification of epitope of the antibodies. The microarray contains 200,000 peptides of SH3YL1. Pre-stained with secondary and control IgG1 antibody reduced background signal. The peptide microarray was incubated with primary antibody (A3 or A4 antibody) and washed with PBS. Secondary antibody to IgG1 was incubated with the peptide array and then scanned the peptide microarray using 635 nm fluorescence channels.

Measurement of Antibody Affinity.

The affinity of antigen-antibody was measured by Octet Red 96e system (ForteBio) with AR2G sensor. Affinity measurement protocol was followed by the manufacturer's recommendations.

Immunoprecipitation (IP)

MES13 cells seeded and grown onto 30 mm culture dish. When cells were grown confluent, serum was starved for 4 hrs and stimulated with 100 mg/ml LPS for 24 hrs. the cell supernatant were concentrated using Amicon® Ultra Centrifugal Filter Devices (Millipore) and cells were lysed with NP40 lysis buffer (0.5% NP40, 1% Triton X-100, 50 mM Tris(pH8.0), 1 mM EDTA, 150 mM NaCl, 1 ug/ml aprotinine, 1 ug/ml leupeptin). Concentrated supernatant and cell lysates were incubated with Soluble ectodomain of human TLRS fused to an IgG1 Fc domain (hTLR5-FC; Invivogen) at 4° C. overnight with continuous rotation. Then incubated with Protein G Sepharose (GE Healthcare) at 4° C. for 2 hrs with continuous rotation. Immune complexes were washed with lysis buffer and immunoprecipitated proteins were mixed with 2×SDS-PAGE sample buffer and boiled at 95° C. for 10 min. The precipitates were subjected to western blot with indicated antibodies.

Western Blot

Cells were lysed with NP40 lysis buffer (0.5% NP40, 1% Triton X-100, 50 mM Tris (pH 8.0), 1 mM EDTA, 150 mM NaCl, 1 ug/ml aprotinine, 1 ug/ml leupeptin). The lysates were incubated at 4° C. for 30 min and performed centrifugation at 14000 rpm for 30 min. the protein concentration was determined by the bicinchoninic acid (BCA) assay (Pierce, Rockford, IL, USA). The proteins were denatured with 5× sample buffer at 95° C. for 10 min. the protein samples were subjected to SDS-PAGE on 10% polyacrylamide gel and transferred on nitrocellulose (NC) membrane (GVS, BO, Italy) at 100 V for 1 hr. Then the transferred blots blocked for 30 min at room temperature in 5% skim milk, and incubated with the indicated primary antibody at 4° C. overnight. The blots were washed with TBS-T buffer with 0.1% tween 20 three times, then incubated at RT for 1 hr with HRP-conjugated secondary antibody. After washed three times with 0.1% TBS-T buffer, the blots were detected using ECL solution (Young In Frontier, Seoul, Republic of Korea) and images were obtained by Amersham Imager 680 (GE Healthcare Life Sciences, Chicago, USA).

Immunohistochemistry

Kidneys and livers were fixed with 10% formalin and processed for histology or immunostaining using standard techniques. 4 um histological section of the kidneys were stained with α-SMA (Dako), 3.5 um section of the livers were stained with α-SMA and F4/80 (Abcam). Sections were rehydrated with series of decreasing alcohol concentrations (100%, 95%, 90%, 80%, 70%). Antigen retrieval step was done by Tris-EDTA, pH9.0 with heating for 15 min at 95-100° C. To block endogenous hydrogen peroxidase activity of the tissue, 3% $H_2O_2$ was applied for 10 min at room temperature. Then the samples were blocked by 2.5% normal goat serum (α-SMA), dako protein block solution (F4/80) at RT for 30 min. the slides were incubated with α-SMA antibody (Dako) for 4° C. overnight. Then slides were washed with PBS and incubated with HRP conjugated secondary antibody for 30 min RT. Then slides treated with a mixture of DAB+ substrate buffer and DAB (3,3'-diaminobenzidine) (Dako; Agilent, Santa Clara, CA, USA) chromogen for color fixation followed by Mayer's hematoxylin (Vector Lab, Burlingame, CA, USA) counterstaining for nuclei. Complete stained samples were dehydrated and mounted with mounting solution (Thermo Scientific, Waltham, MA, USA). Images of the tissue were analyzed at least 20 to 30 glomeruli of fields for indicated magnifications with ImagePro plus 7.0 software.

Periodic Acid-Schiff (PAS), Masson's Trichrome Staining

Paraffin embedded mouse kidney sections were cut in 4 um thick and periodic acid-Schiff (PAS) and masson's trichrome staining were performed. The PAS staining was performed using periodic acid (Junser, Chuo-ku, Tokyo, Japan) and Schiff reagent (sigma, St/Louis, MO) with standard protocol. For masson's trichrome staining (Polyscience), sections were stained with protocol provided from manufacturer.

Statistical Analysis

All values were expressed as the mean±SD or ±SEM. Statistical significance between groups was determined using two tailed Student's t-test. P value less than 0.05 was considered statistically significant and all tests were two sided.

Example 1.2. Results

TLR5 Acts as a SH3YL1 Receptor

Secretion of SH3YL1 protein was induced in MES13 mesangial cells in response to high glucose (HG) stimulation (FIG. 1). Mouse mesangial cell line (MES13) were incubated with 30 mM of HG for 9 and 24 hrs. Cell supernatants were concentrated were subjected into immunoblotting with antibody to SH3YL1.

Figure 2:
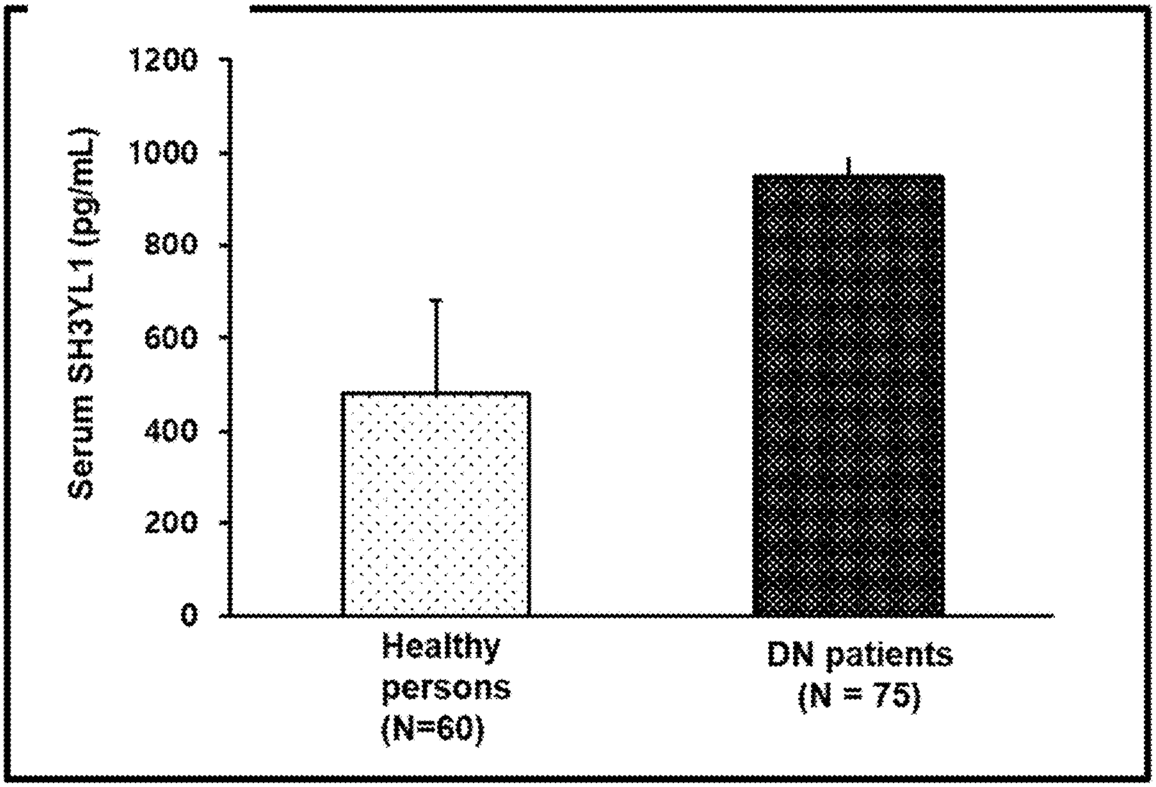
FIG. 2. Serum SH3YL1 protein in diabetic nephropathy patients was induced compared to that in heathy persons. Serum SH3YL1 was detected in healthy persons and DN using a human SH3YL1 ELISA kit.

Serum SH3YL1 protein in diabetic nephropathy patients was induced compared to that in heathy persons (FIG. 2). Serum SH3YL1 was detected in healthy persons and DN using human SH3YL1 ELISA kit.

Figure 3:
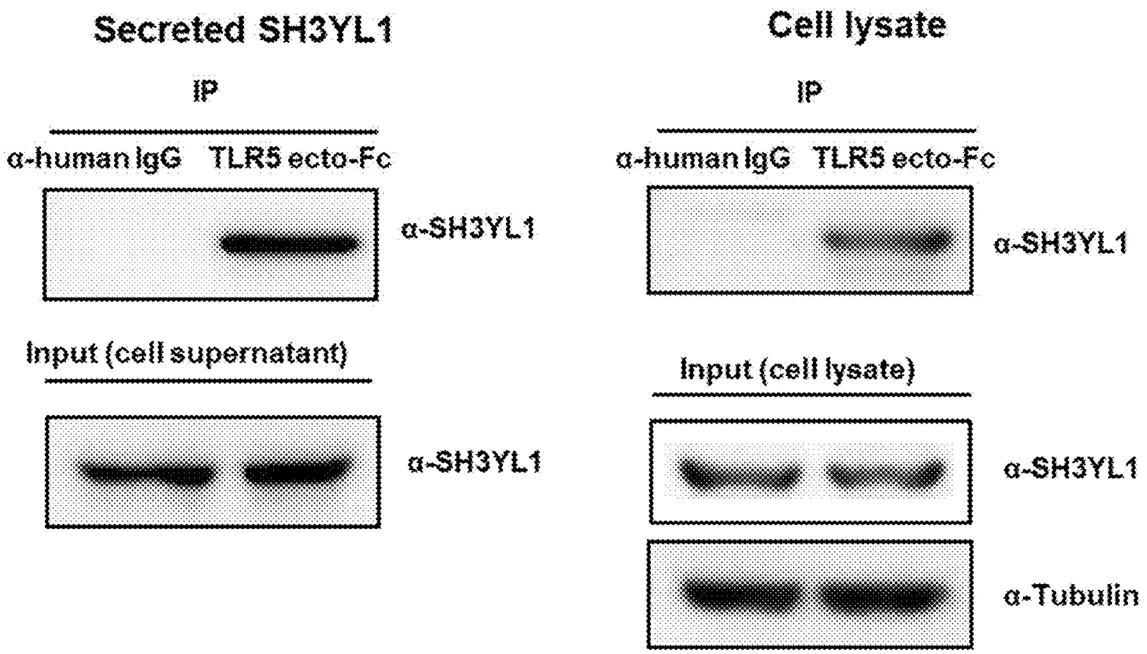
FIG. 3. SH3YL1 interacted with the extracellular domain of TLR5. Interaction of SH3YL1 with the ectodomain of TLR5 was measured by immunoprecipitation (IP) with TLR5-ecto-Fc (hTLR5-FC; Invivogen). MES13 was stimulated with 100 ng/ml LPS for 24 hrs. Cell supernatants and cell lysates were immunoprecipitated with TLR5-ecto-Fc or human control IgG as a negative control. The resulting precipitates were subjected to immunoblot analysis with antibodies to SH3YL1.
Figure 4:
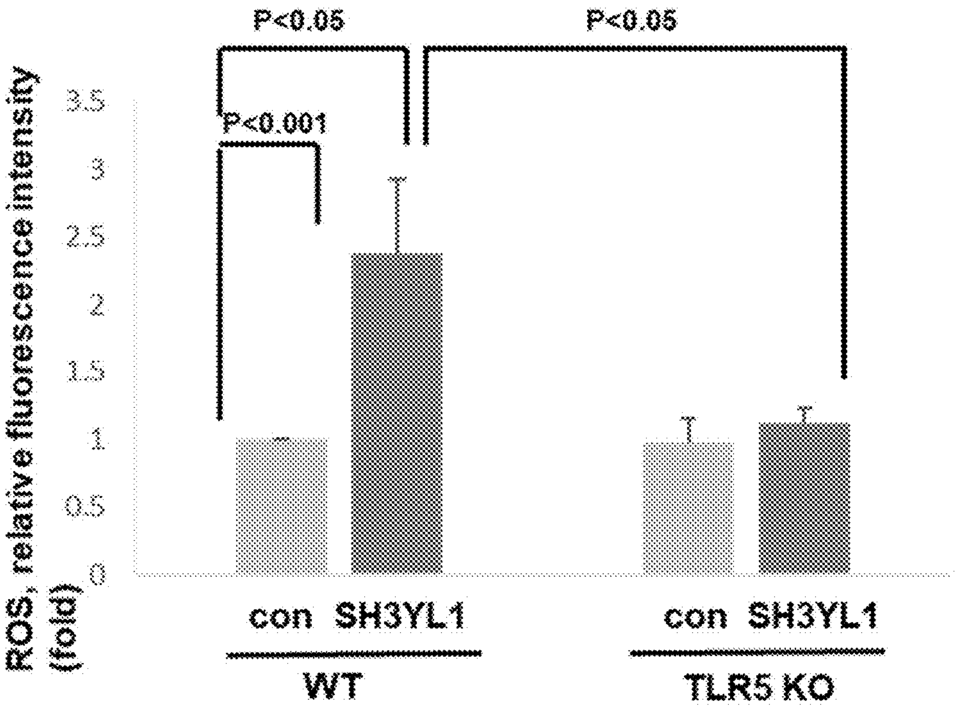
FIG. 4. SH3YL1 stimulated ROS generation in pMMC through TLR5. Primary mesangial cells (pMMC) from wild-type and TLR5 knockout mice were stimulated with SH3YL1 (1 ug/ml) for 10 min. The generation of ROS (reactive oxygen species) was monitored by confocal microscopy with PO-1 fluorescence (N=3, data shown as mean±SD, $p<0.001$, $P<0.05$ as determined by student's t-test).
Figure 5:
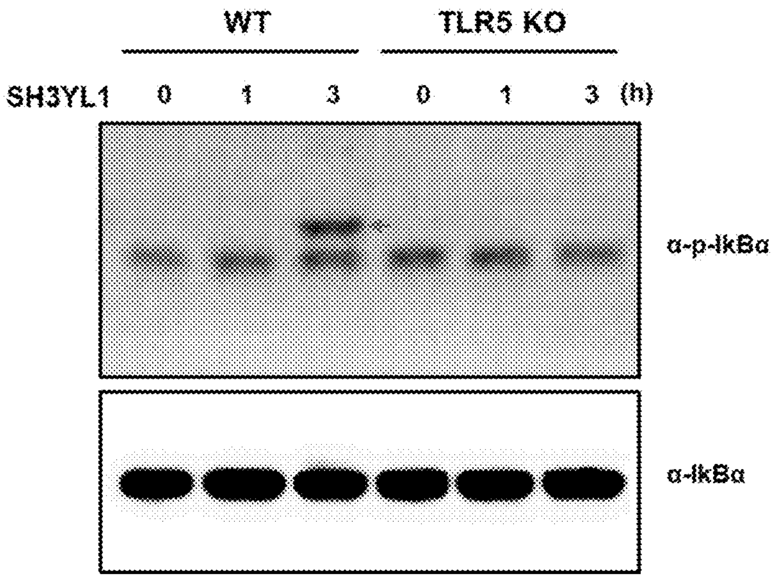
FIG. 5. SH3YL1 regulated TLR5-dependent NF-κB activation. PMMC from wild-type and TLR5 knockout mice were stimulated with SH3YL1 (1 ug/ml) for 1 hr or 3 hr. The IκB phosphorylation were subjected to immunoblot analysis with antibodies to total IκBα and phospho-IκBα antibodies.
Figure 6:
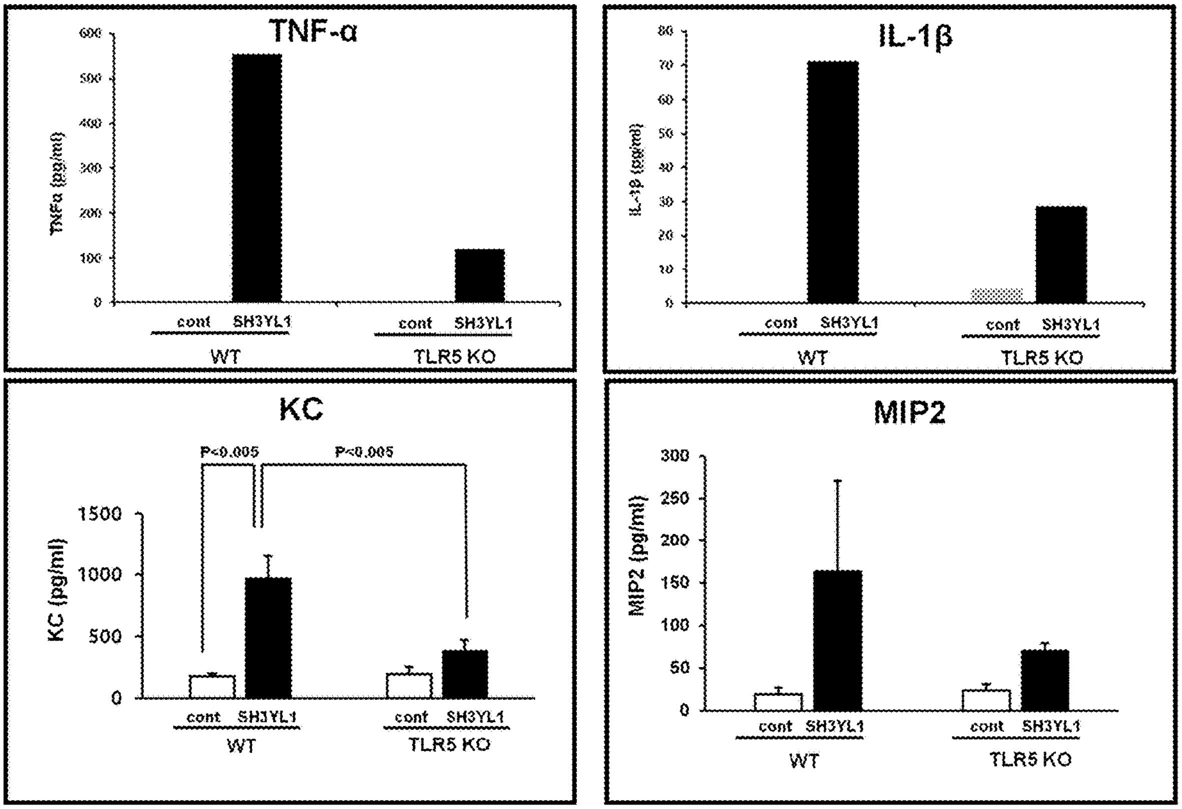
FIG. 6. SH3YL1 failed to stimulate the production of pro-inflammatory mediators in pMMC from TLR5 KO mice. PMMC from wild type and TLR5 knockout mice were stimulated with SH3YL1 (1 ug/ml) for 24 hr. TNF-α, IL-1β, KC, and MIP2 secretion were analyzed using an ELISA kit according to the manufacturer's instructions.

To investigate the function of secreted SH3YL1 protein, integral proteins working as its receptor were screened. TLR5 was identified as a secreted SH3YL1 protein. The ectodomain of TLR5 was found to bind to SH3YL1 (FIG. 3). To validate the SH3YL1-TLR5 function in cell, primary mouse mesangial cells (pMMCs) from TLR5 KO mice were obtained. Stimulation of TLR5 KO pMMCs with SH3YL1 failed to induce ROS generation (FIG. 4) and NFkB activation (FIG. 5), compared to WT pMMCs. Furthermore, pro-inflammatory cytokines production in response to secreted SH3YL1 stimulation was measured. Incubation of TLR5 KO pMMCs with SH3YL1 resulted in significantly reduced pro-inflammatory cytokines production including IL-1β, TNF-α, KC and MIP2 (FIG. 6).

Generation of Monoclonal Antibodies Against SH3YL1

After observation of secreted SH3YL1 protein, therapeutic antibodies against SH3YL1 were generated. To generate therapeutic antibodies to SH3YL1, a synthetic human single chain variable fragment (scFv) library with a single scaffold (human variable heavy chain VH3-23 (DP47) and human variable light chain Vλ1g (DPL3) joined by a 15-amino acid linker (GGGGS)3) and six randomized complementarity determining regions (CDRs) was used. After three times of panning phage library, two different scFv antibodies (A3 and A4) were obtained. CDRs of each scFv antibody (A3 or A4) were determined (SEQ ID NOS:13, 14, and 15 or SEQ ID NOS:16, 17, and 18, respectively). To obtain human IgG1 antibody against SH3YL1 from scFv antibody (A3 or A4 clone), variable regions of light and heavy chain in each scFv of A3 or A4 were subcloned into vectors of constant light chain and heavy chain, respectively. The affinity of each IgG1 antibody (A3 or A4) was measured using ForteBio Octet with AR2G sensor. It was found that the affinity of A3 or A4 was $1.0\times10^{-12}$ or $3.65\times10^{-10}$. To determine the epitope of each antibody (A3 or A4 antibody), the customized peptide microarray (Axxelera, Germany) has been applied. It was found that A3 antibody recognized the peptide 317DSHFDWWE324 (SEQ ID NO:25) of SH3YL1 and the epitope of A4 was 203LYEILDSF210 (SEQ ID NO:26) of SH3YL1.

Figure 7:
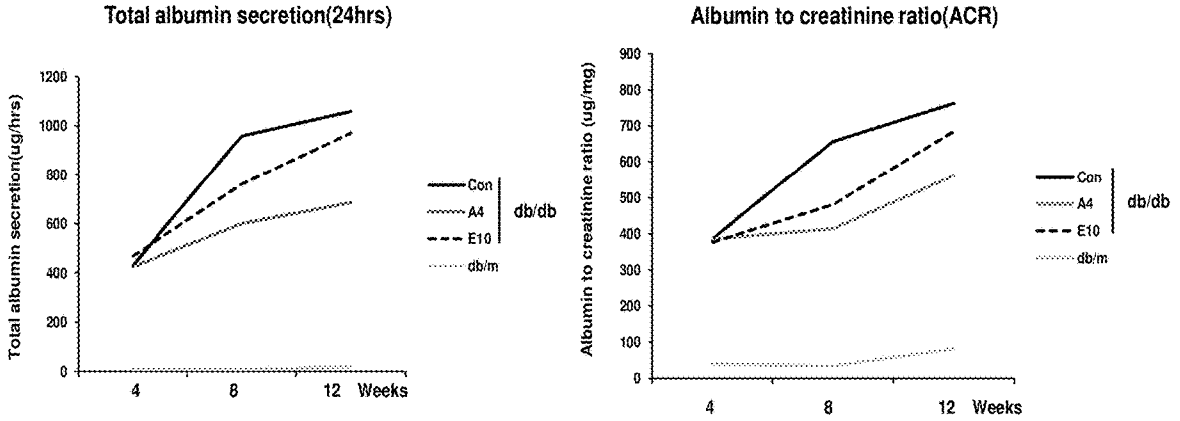
FIG. 7. Therapeutic effect of SH3YL1 antibodies on db/db mice. The db/m and db/db mice (8-week-old) were divided into four groups: (1) control db/m mice (n=5), (2) control db/db mice treated with vehicle (n=5), (3) db/db mice treated with CRB-A4 (n=5), and (4) db/db mice treated with CRB-E10 (n=5). Antibodies were injected intraperitoneally at a dose of 10 mg/kg per week for 12 weeks. Fasting blood glucose was monitored every 4 weeks. Reduction of albumin secretion in urine by SH3YL1 antibodies treatment in db/db mice. Urine were collected every 4 weeks and measured albumin and creatinine levels. Total albumin secretion per day and albumin to creatinine ratio (ACR) were measured in urine.
Figure 8:
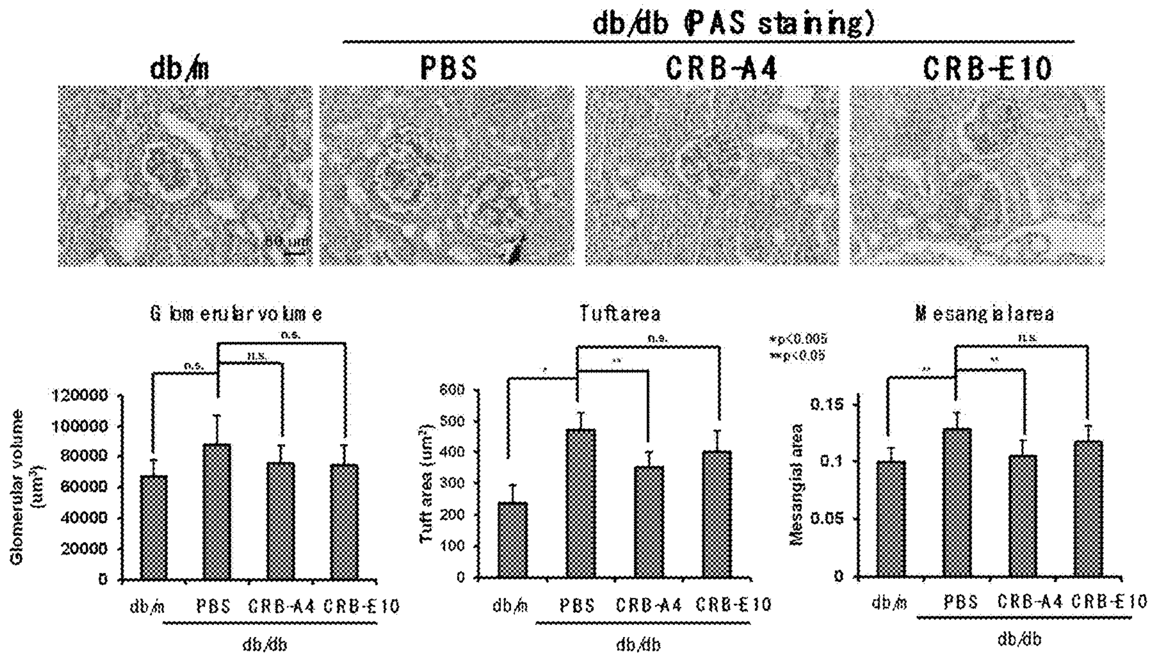
FIG. 8. Reduction of kidney mesangial expansion by SH3YL1 antibody treatment in db/db mice. Paraffin section of kidney tissues were subjected into PAS staining. Glomerulus images were taken by microscopy. The glomerular volume, tuft area and fractional mesangial area (PAS positive area/tuft area) were evaluated using Image Pro Plus 7 software (N=5 per group, data shown as mean±SD, *$P<0.005$, **$P<0.05$ as determined by student's t-test).
Figure 9:
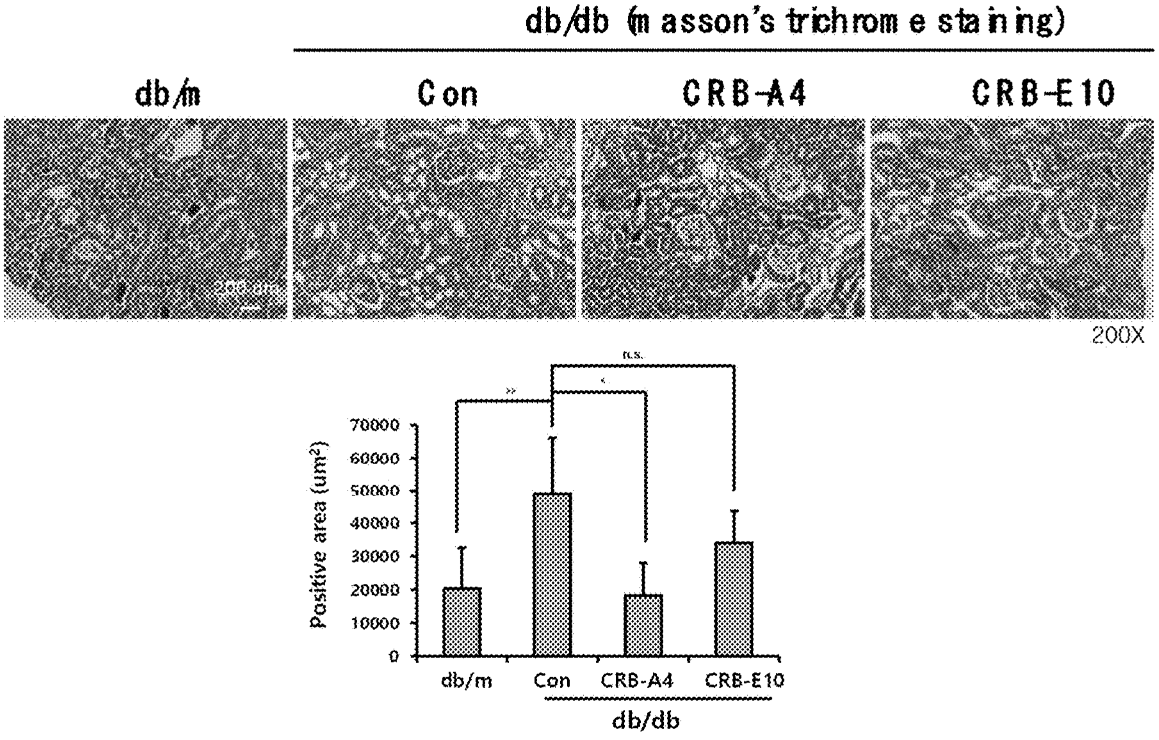
FIG. 9. SH3YL1 antibody treatment protected from renal fibrosis in db/db mice. The kidney sections were stained with masson's trichrome staining. Positively stained collagen area was shown with dark color in masson's trichrome staining. Quantification of positive stained area was done in 25-30 different fields using Image Pro plus 7 program (N=5 per group, data shown as mean±SD, *$P<0.005$, **$P<0.05$ as determined by student's t-test).
Figure 10:
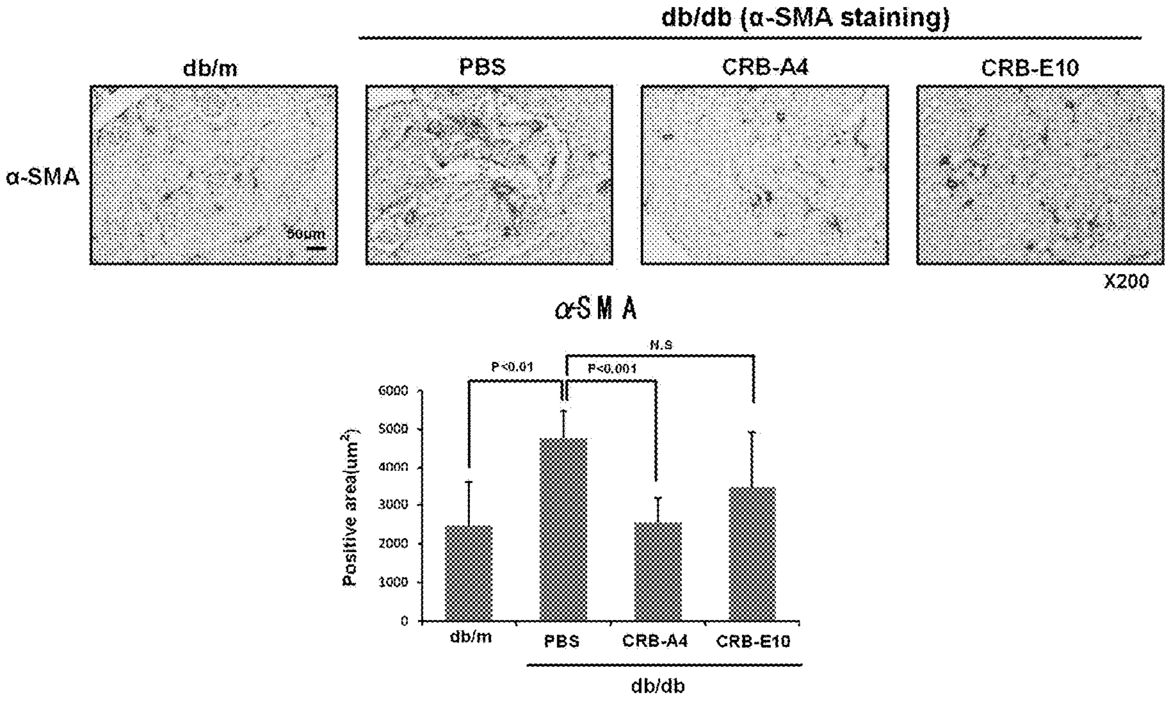
FIG. 10. Inhibition of α-SMA expression as a fibrosis marker by SH3YL1 antibody treatment. The kidney sections were IHC stained with antibody against α-SMA. Positively stained area of IHC staining turned brown after exposure to 3,3'-diaminobenzidine. Quantification of positive stained area was done 20-25 field using Image Pro plus 7 program (N=5 per group, data shown as mean±SD, $P<0.01$, $P<0.001$ as determined by student's t-test).

Evaluation of Therapeutic Antibody Efficacy in db/db Mice as Diabetic Nephropathy Animal Model The therapeutic efficacy for SH3YL1 antibodies was investigated in db/db mice as type 2 diabetic nephropathy animal model. SH3YL1 antibodies (A4 and E10, 10 mpk/week for 12 weeks, i.p. injection) have been injected into db/db mice (N=5) or db/m mice (N=5) as a control for 12 weeks and then sacrificed them. Both of control PBS-injected and SH3YL1 antibodies-injected db/db mice showed high serum glucose levels, indicating that the antibody injection did not affect diabetic condition in db/db mice. Albumin secretion in urine and ratio of albumin to creatinine were significantly decreased in SH3YL1 antibodies-injected db/db mice (FIG. 7). A4 antibody showed higher therapeutic efficacy than E10 antibody (FIG. 7). Mesangial expansion is a well-known parameter in diabetic nephropathy. Thus, mesangial expansion in control PBS-injected and SH3YL1 antibodies-injected db/db mice was performed. Glomerular volume, tuft area and mesangial area were increased in control PBS-injected db/db mice (FIG. 8). However, SH3YL1 antibodies-injected db/db mice showed a reduction of three parameters with db/m mice as control level (FIG. 8). Next, it was determined whether SH3YL1 antibodies control fibrosis in kidney. Masson's trichrome and α-SMA staining were performed as a fibrosis marker in control PBS-injected and SH3YL1 antibodies-injected db/db mice. Masson's trichrome and α-SMA staining were significantly reduced in SH3YL1 antibodies-injected db/db mice, compared to control PBS-injected db/db mice (FIGS. 9 and 10). A4 antibody showed higher fibrosis protection activity than E10 antibody (FIGS. 8-10). Taken together, SH3YL1 antibodies injection showed good therapeutic efficacy in diabetic nephropathy.

Figure 64:
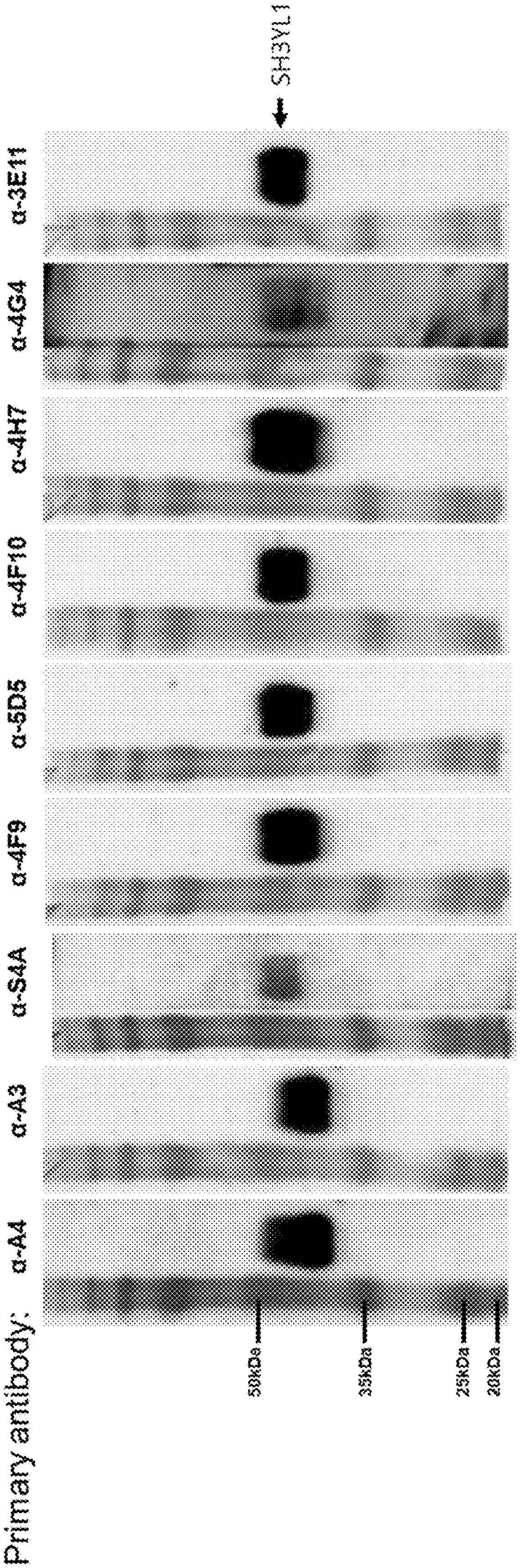
FIG. 64. Western blot of antibodies A4, A3, S4A, 4F9, 5D5, 4F10, 4H7, 4G4, and 3E11.

Additional antibodies identified using the methods provided herein are 5D5, 3E11, 44F10, 4G4, 4F9, $4H_7$, and S4A. The Western blot results for antibodies A4, A3, S4A, 4F9, 5D5, 4F10, 4H7, 4G4, and 3E11 are shown in FIG. 64. The binding affinities of antibodies 5D5, 3E11, 44F10, 4G4, 4F9, 4H7, and S4A are shown in FIG. 65.

Provided below is Table 1 showing the amino acid (AA) and nucleotide (NT) sequences of antibodies A3, A4, S4A, 4F9, 4F10, 5D5, 4G4, 3E11, and 4H7.

TABLE 1

| Antibody | Variable Region AA: CDR1, 2, and 3 SEQ ID NOS: | Variable Region AA SEQ ID NO: | Variable Region NT SEQ ID NO: | Constant Region AA SEQ ID NO: | SH3YL1 Epitope AA SEQ ID NO: |
|---|---|---|---|---|---|
| A3 Heavy Chain | 13, 14, 15 | 1 | 2 | 9 | 25 |
| A3 Light Chain | 16, 17, 18 | 3 | 4 | 10 | |
| A4 Heavy Chain | 19, 20, 21 | 5 | 6 | 9 | 26 |
| A4 Light Chain | 22, 23, 24 | 7 | 8 | 10 | |
| S4A Heavy Chain | 63, 64, 65 | 31 | 32 | 9 | 98 |
| S4A Light Chain | 66, 67, 68 | 33 | 34 | 10 | |
| 4F9 Heavy Chain | 69, 70, 71 | 35 | 36 | 61 | 99 |
| 4F9 Light Chain | 72, 73, 74 | 37 | 38 | 62 | |
| 4F10 Heavy Chain | 69, 75, 76 | 39 | 40 | 61 | 100 |
| 4F10 Light Chain | 77, 78, 79 | 41 | 42 | 62 | |
| 5D5 Heavy Chain | 69, 80, 81 | 43 | 44 | 61 | 101 |
| 5D5 Light Chain | 82, 83, 84 | 45 | 46 | 62 | |
| 4G4 Heavy Chain | 13, 85, 86 | 47 | 48 | 61 | 99 |
| 4G4 Light Chain | 87. 88. 74 | 49 | 50 | 62 | |
| 3E11 Heavy Chain | 89, 90, 91 | 51 | 52 | 61 | 99 |
| 3E11 Light Chain | 92, 73, 74 | 53 | 54 | 62 | |
| 4H7 Heavy Chain | 93, 94, 95 | 55 | 56 | 61 | 99 |
| 4H7 Light Chain | 96, 97, 74 | 57 | 58 | 62 | |

Example 2. Non-Alcoholic Steatohepatitis (NASH)

Example 2.1. Materials and Methods

Animals

All procedures of animals were approved and performed by the Institutional Animal Care and Use Committes (IACUC) and ethical guidances at Ewha Womans University.

Six-week-old male diabetic db/db mice (BKS.Cg-Dock$7^{m}$+/+Lepr$^{db}$/J) were purchased from the Jackson Laboratory (Bar Harbor, ME, USA). To investigate the effect of SH3YL1 antibodies (CRB-A4, CRB-E10) 8-week-old mice were divided into four groups: (1) control db/m mice (n=5), (2) control db/db mice treated with vehicle (n=5), (3) db/db mice treated with CRB-A4 (n=5), and (4) db/db mice treated with CRB-E10 (n=5). Antibodies were injected intraperitoneally at a dose of 10 mg/kg per week for 12 weeks.

Body weight, blood glucose level, Urine volume were measured every 4 weeks. Blood glucose level was measured using glucometer (Accucheck; Roche, Basel, Switzerland). Mice were separated in metabolic cages individually for 24 hrs for the urine collection. After 12 weeks, mice were sacrificed and obtained serum by cardiac functure for further analysis, and kidneys were dissected rapidly for paraffin/frozen section or protein/RNA analysis.

High Fat High Fructose Diet (FFD) Model 8-week-old male KO and wild-type mice were fed with FFD (#D12079B, research diet, supplemented with high-fructose corn syrup with a final concentration of 42 g/L in the drinking water) for 20 weeks. All animals were house with a 12-h-light, 12-4-dark cycle in a room under controlled temperature and humidity and allowed by the Animal Subjects Committees of the Ewha Womans University (Seoul, Korea).

All other methods are as described in Example 1 above.

Example 2.2. SH3YL1 is Secreted in Plasma of NASH Patients

Figure 11:
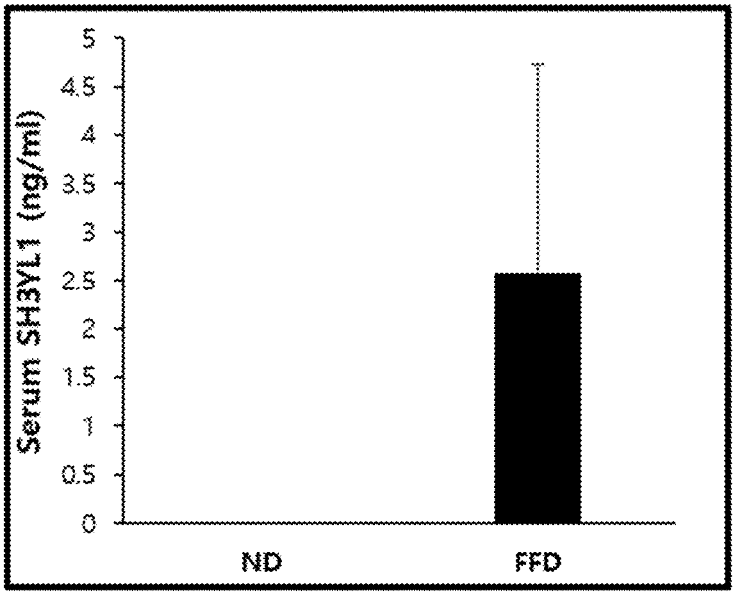
FIG. 11. Secreted SH3YL1 level was induced in serum of FFD NASH model. Serum SH3YL1 was detected in serum of normal diet (ND) and high fat and high fructose diet (FFD) NASH model using human SH3YL1 ELISA kit.
Figure 12:
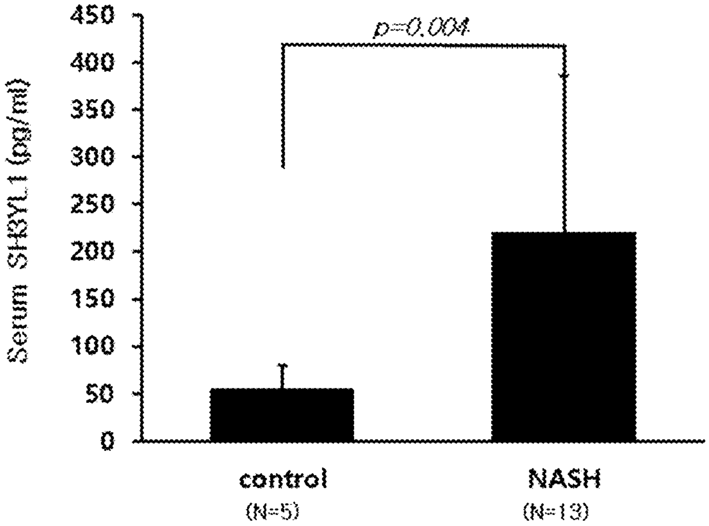
FIG. 12. Secreted SH3YL1 level was induced in serum of NASH patients. Serum SH3YL1 in healthy controls (N=5) and NASH patients (N=13) was detected using human SH3YL1 ELISA kit.

To measure the secretion of SH3YL1 in non-alcoholic steatohepatitis (NASH) animal model, a high-fat high-fructose diet (FFD) model was used. Secreted SH3YL1 protein level of serum in FFD model was higher than that in normal diet (ND) animals (FIG. 11). To evaluate clinical implication of SH3YL1 into NASH, SH3YL1 protein level was measured in serum of NASH patients. SH3YL1 level of NASH patients was higher than that of healthy donor (FIG. 12).

Figure 13:
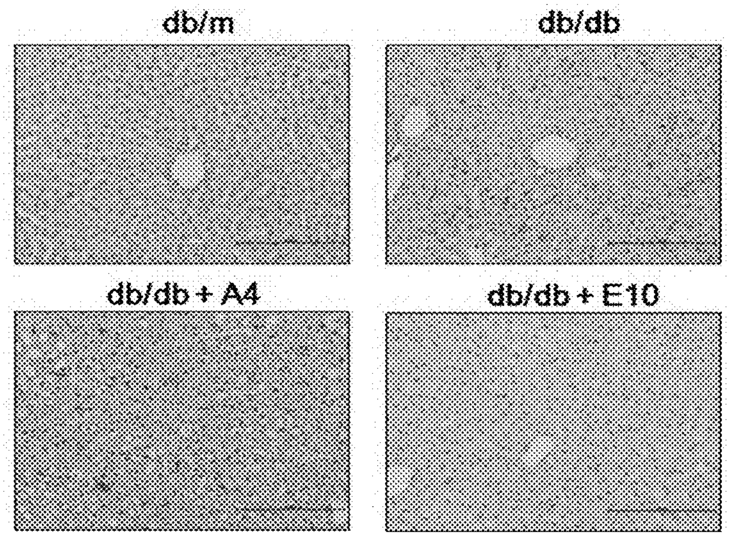
FIG. 13. Treatment with SH3YL1 antibody inhibited macrophage infiltration in db/db mice. Paraffin sections of the liver were stained with F4/80 for macrophage infiltration. Positively stained area turned brown with DAB application.
Figure 14:
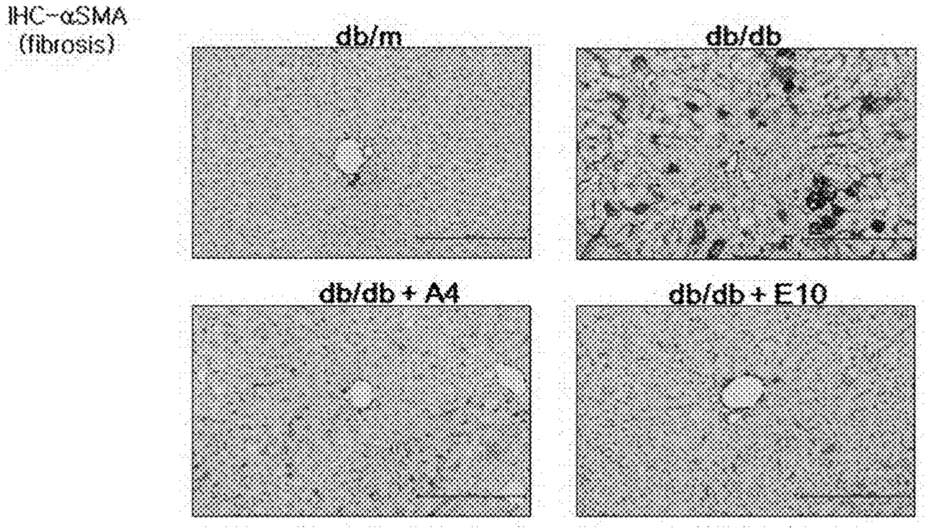
FIG. 14. Treatment with SH3YL1 antibody suppressed liver fibrosis in db/db mice. The liver sections were IHC stained with antibody against α-SMA. Positively stained area of IHC staining turned brown after exposure to 3,3'-diaminobenzidine.

Example 2.3. Evaluation of Therapeutic Antibody Efficacy in db/db Mice as Non-Alcoholic Steatohepatitis (NASH) Animal Model It was investigated whether SH3YL1 antibodies control liver fibrosis and inflammation in db/db mice as a NASH animal model. To test the protective activity of SH3YL1 antibodies in inflammation of db/db mice, F4/80 macrophage infiltration was measured in control PBS-injected and SH3YL1 antibodies-injected db/db mice. F4/80 macrophage infiltration was significantly reduced in SH3YL1 antibodies-injected db/db mice, compared to control PBS-injected db/db mice (FIG. 13). Next, therapeutic efficacy of SH3YL1 antibodies was evaluated in liver fibrosis as measuring of α-SMA expression control PBS-injected and SH3YL1 antibodies-injected db/db mice. Liver tissues of PBS-injected db/db mice showed significantly increased α-SMA expression, compared to db/m mice. However, SH3YL1 antibodies-injected db/db mice failed to detect α-SMA expression (FIG. 14). Taken together, SH3YL1 antibodies injection showed good therapeutic efficacy in NASH model.

Example 2.4. Summary

Intracellular SH3YL1 was secreted by inflammation stimuli including high glucose and LPS. Secreted SH3YL1 served as pro-inflammatory molecule through the interaction with TLR5. These results suggested that inflammatory signal induces the secretion of SH3YL1 and secreted SH3YL1 shows a potent inflammatory activity, leading to further inflammation and triggering a pathogenic stage. SH3YL1 antibodies were developed and applied to db/db mice as a DN and NASH model. SH3YL1 antibodies show good therapeutic efficacy in DN and NASH treatment.

FIG. 66 shows the amino acid sequence of human TLR5 extracellular domain (aa 21-639) of hTLR5-FC (SEQ ID NO:59) and supports that SH3Y11 interacts with TLR5 ectodomain in FIG. 3.

Example 3. Cisplatin-Induced Acute Kidney Injury (AKI)

Example 3.1. Materials and Methods

Cisplatin-Induced Acute Kidney Injury (AKI) Model

To induce acute kidney injury, 8-week-old C57BL/6J mice were intraperitoneally injected with Cisplatin (Sigma, St. Louis, MO) at 10 mg/kg. To investigate the effect of SH3YL1 antibodies (CRB-A4), mice were divided into three groups: (1) control mice (n=9), (2) cisplatin injected mice treated with human control IgG (n=13), (3) cisplatin injected mice treated with CRB-A4 (n=12). Human control IgG and SH3YL1 antibodies (CRB-A4) were injected intravenously at 10 mg/kg prior to cisplatin injection. The animals were sacrificed at 3 days after injection and serum and urine were obtained for further analysis, and kidneys were dissected rapidly for paraffin/frozen section or protein/RNA analysis.

Assessment of Kidney Function and Kidney Injury

Urinary albumin was measured using commercial ELISA (ALPCO, Westlake, OH, USA). Serum and urinary creatinine level were determined with enzymatic colorimetric assay (ARBOR ASSAYS, Ann Arbor, MI, USA). Albumin to creatinine ratio (ACR) was calculated using total albumin with urinary creatinine. Blood urea nitrogen (BUN) was measured with colorimetric assay kit (ARBOR ASSAYS, Ann Arbor, MI, USA). Serum Cystatin C level was determined by ELISA assay kit according to the manufacturer's instruction (R&D systems, Minneapolis, MN, USA). NGAL and KIM-1 were measured by ELISA (R&D systems) in urine and serum following the manufacturer's instructions.

Pro-Inflammatory Cytokine ELISA

To determine in vitro pro-inflammatory cytokine levels, primary mouse mesangial cells (pMMCs) were isolated and cultured in 35 mm plates ($5\times10^5$). The pMMCs were serum starved for 4 hrs and then incubated with SH3YL1 (1 μg/ml) for 24 hrs, and then the medium was collected. TNF-α, IL-1β, MIP2, and KC protein levels were determined by ELISA assay kit according to the manufacturer's instruction (R&D systems). Cisplatin-induced AKI model mouse serum was also used to determine TNF-α and KC levels using an ELISA kit (R&D systems).

Periodic Acid-Schiff (PAS), Hematoxylin and Eosin (H&E), Masson's Trichrome Staining Paraffin embedded mouse kidney sections were cut into 4 μm thickness and periodic acid-Schiff (PAS), hematoxylin and eosin (H&E), and masson's trichrome staining were performed. The PAS staining was performed using periodic acid (Junsei, Chuo-ku, Tokyo, Japan) and Schiff reagent (sigma, St/Louis, MO) with standard protocol. H&E staining was performed using hematoxylin (Vector, Burlingame, CA, USA) and Eosin (sigma) with standard method. For masson's trichrome staining (Polyscience), sections were stained with protocol provided from manufacturer.

Tubular Damage Scoring

To determine the degree of renal tubular injury, H&E staining was performed. All histological examinations were performed by renal pathologist in a blinded fashion. Histological changes due to tubular injury score were quantified by the percent of tubules that displayed cell necrosis, loss of brush border, cast formation, and tubule dilatation as follows: 0, none; 1, 1-25%; 2, 26-50%; 3, >50%.

Immunohistochemistry

Kidneys were fixed with 10% formalin and processed for histology or immunostaining using standard techniques. Four (4) μm histological section of the kidneys were stained with α-SMA (Dako; Agilent, Santa Clara, CA, USA). Sections were rehydrated with series of decreasing alcohol concentrations (100%, 95%, 90%, 80%, 70%). Antigen retrieval step was done by Tris-EDTA, pH 9.0 with heating for 15 min at 95° C.-100° C. To block endogenous hydrogen peroxidase activity of the tissue, 3% $H_2O_2$ was applied for 10 min at room temperature. Then the samples were blocked by 2.5% normal goat serum (α-SMA) at RT for 30 min. The slides were incubated with α-SMA antibody (Dako) for 4° C. overnight. Then slides were washed with PBS and incubated with HRP conjugated secondary antibody for 30 min RT. Then the slides treated with a mixture of DAB+ substrate buffer and DAB (3,3'-diaminobenzidine) (Dako) chromogen for color fixation followed by Mayer's hematoxylin (Vector Lab, Burlingame, CA, USA) counterstaining for nuclei. Complete stained samples were dehydrated and mounted with mounting solution (ThermoFisher Scientific, Waltham, MA, USA). Images of the tissue were analyzed at least 20 to 30 glomeruli of fields for indicated magnifications with ImagePro plus 7.0 software.

TdT-UDP Nick End Labeling (TUNEL) Staining

Paraffin embedded mouse kidney sections cut in 4 μm thickness were used to detect apoptosis. An in situ apoptosis detection kit (Merck) designed to label apoptotic cells by modifying genomic DNA utilizing terminal deoxynucleotidyl transferase (TdT) by specific staining was used according to the manufacturer's instruction. The slides were visualized using a laser scanning confocal microscope (Carl Zeiss vision system; LSM880 airyscan).

Statistical Analysis

All values were expressed as the mean±SEM. Statistical significance between groups was determined using two tailed Student's t-test. P value less than 0.05 was considered statistically significant and all tests were two sided.

Example 3.2. Results

SH3YL1 Antibody Suppresses Cisplatin-Induced Renal Dysfunction

Figure 55A:
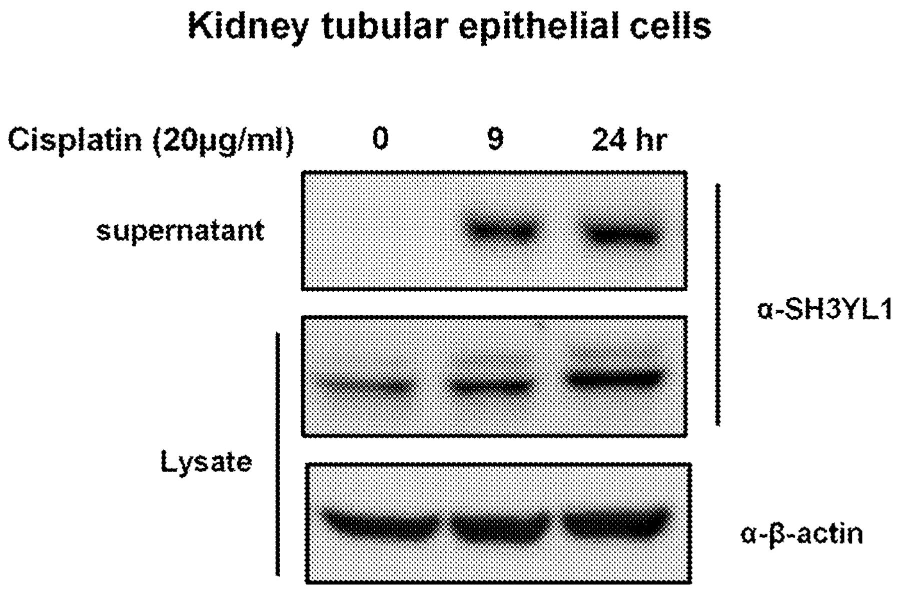
FIGS. 55A-55F. SH3YL1 antibody improves renal function in cisplatin-induced AKI models.
Figure 55B:
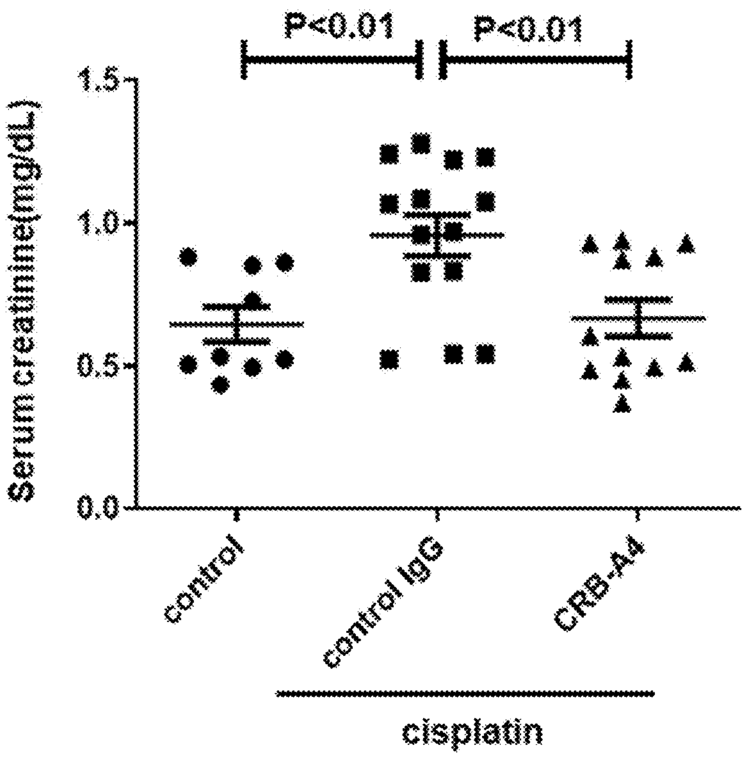
Figure 55C:
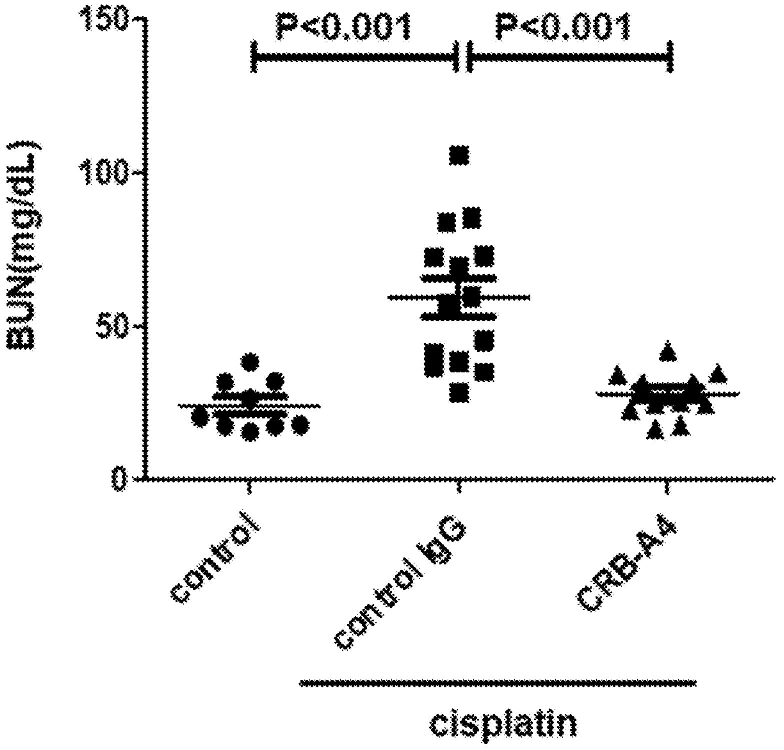
Figure 55D:
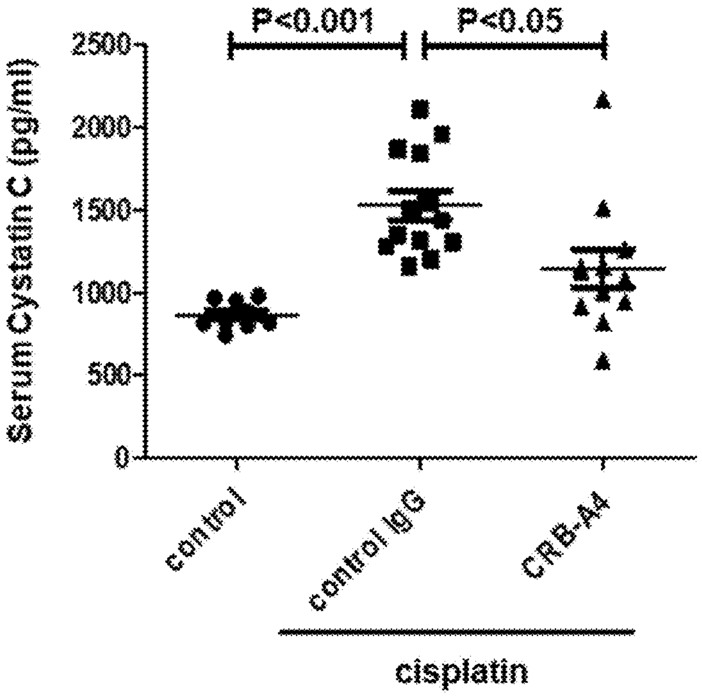
Figure 55E:
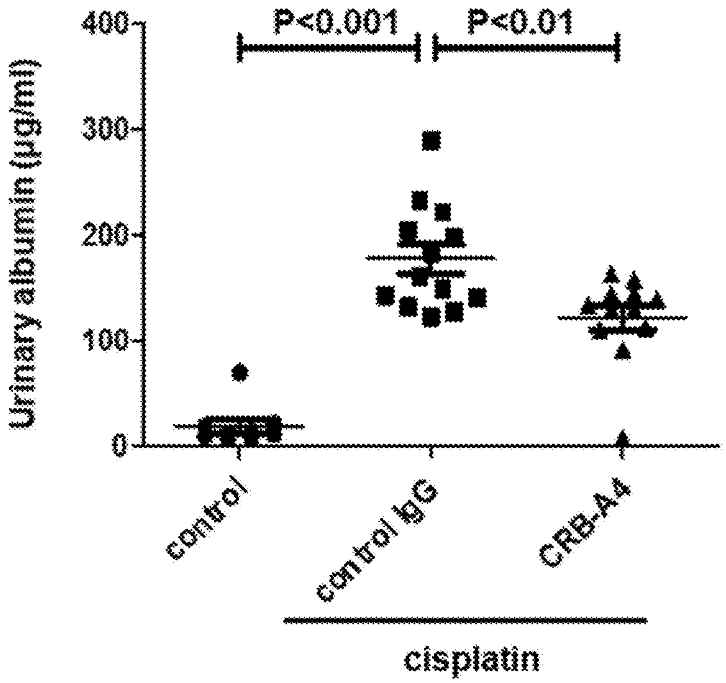
Figure 55F:
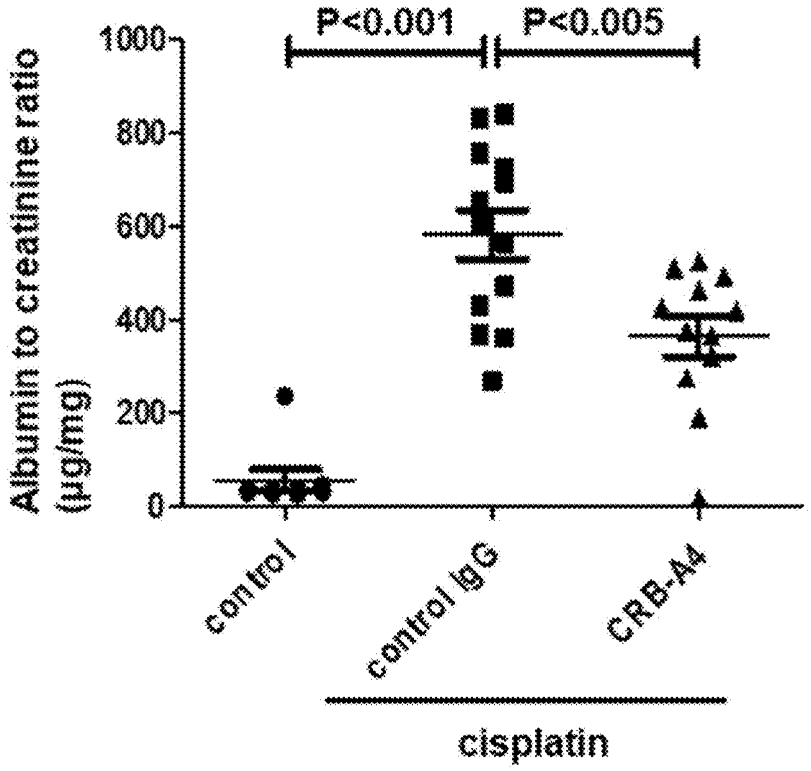
Figure 56A:
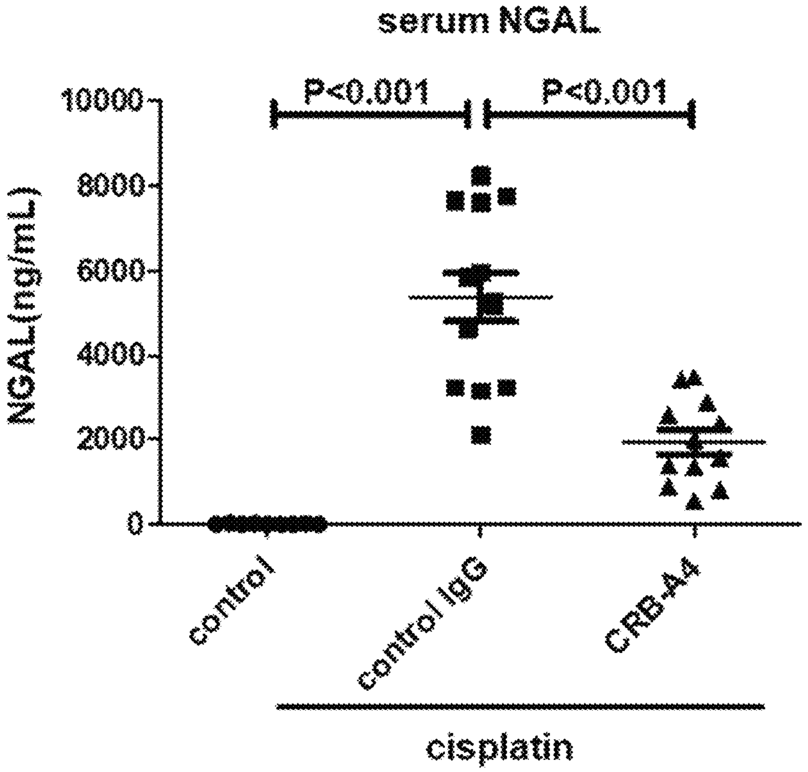
FIGS. 56A-56D. Treatment of SH3YL1 antibody reduces the increase in kidney injury markers. NGAL was measured in serum (FIG. 56A) and urine (FIG. 56B) using the indicated ELISA kit (N>9 per group, data shown as mean±SEM, $P<0.001$, $P<0.005$, as determined by student's t-test). Serum KIM-1 (FIG. 56C) and urinary KIM-1 (FIG. 56D) were measured using an ELISA kit (N>9 per group, data shown as mean±SEM, $P<0.001$, $P<0.005$, N.S. represents not significant, as determined by student's t-test).
Figure 56B:
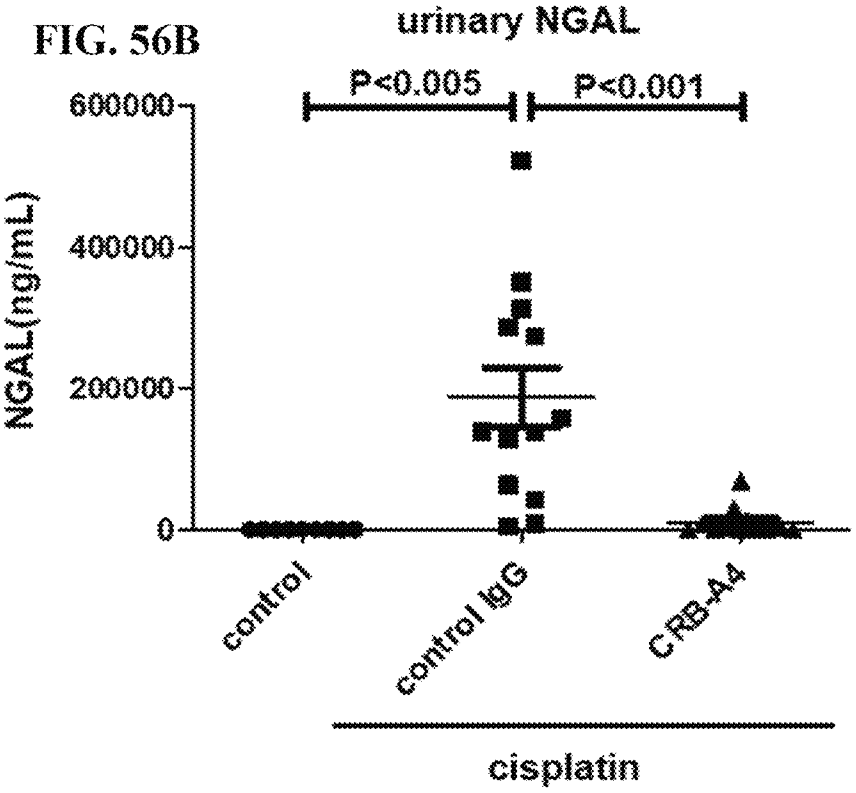
Figure 56C:
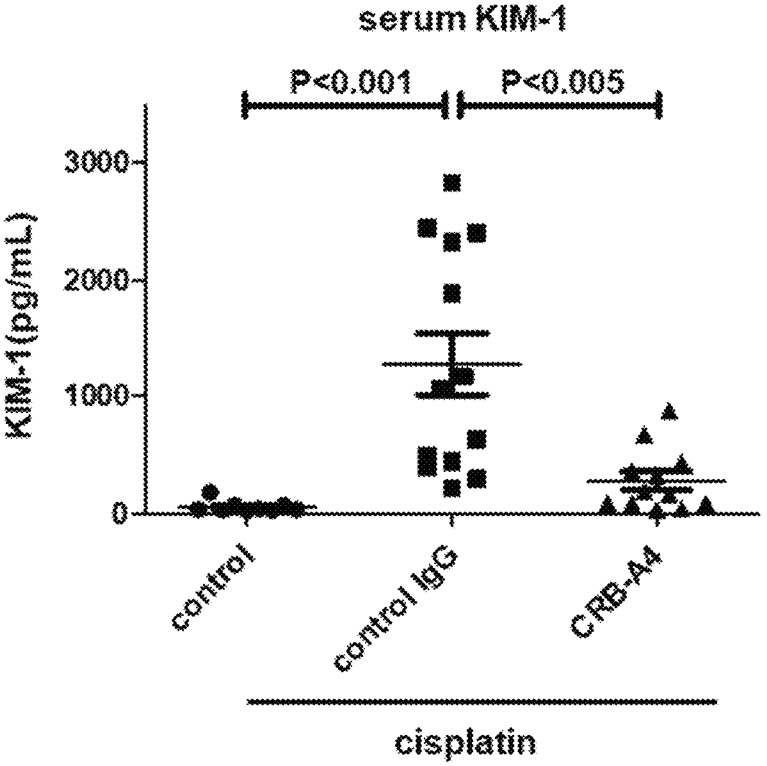
Figure 56D:
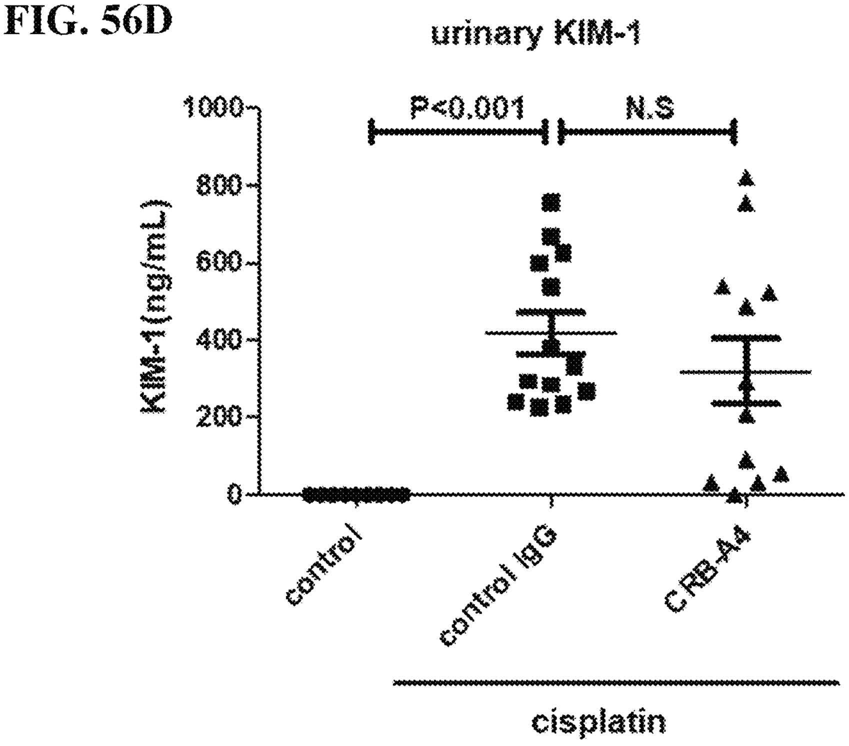
Figure 57A:
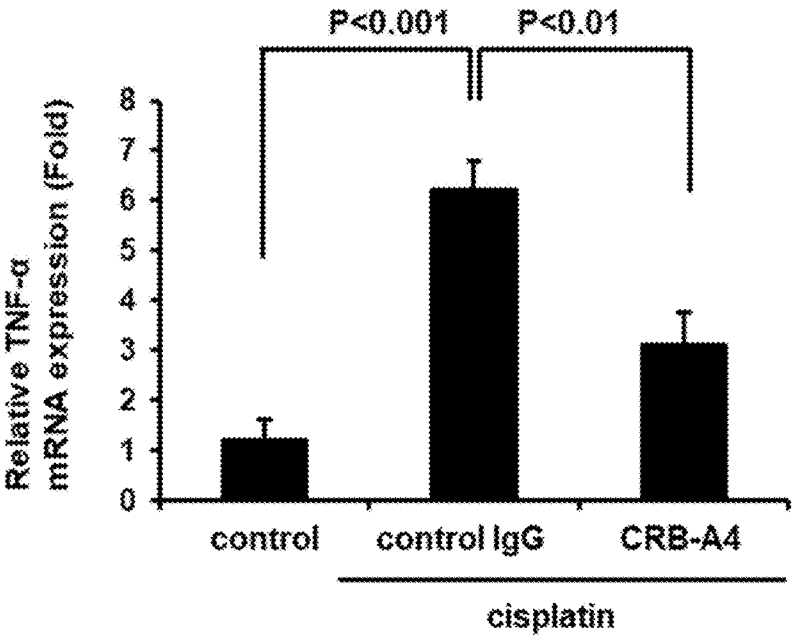
FIGS. 57A-57E. Treatment of SH3YL1 antibody attenuates pro-inflammatory cytokine production in cisplatin induced AKI mice. Quantification of TNF-α (FIG. 57A), IL-6 (FIG. 57B), KC (FIG. 57C), MIP2 (FIG. 57D), MCP-1 (FIG. 57E) mRNA expression. The results were normalized by 18s (N=4 of mice per group, data shown as mean±SEM, P<0.001, P<0.005, N.S. represents not significant, as determined by student's t-test).
Figure 57B:
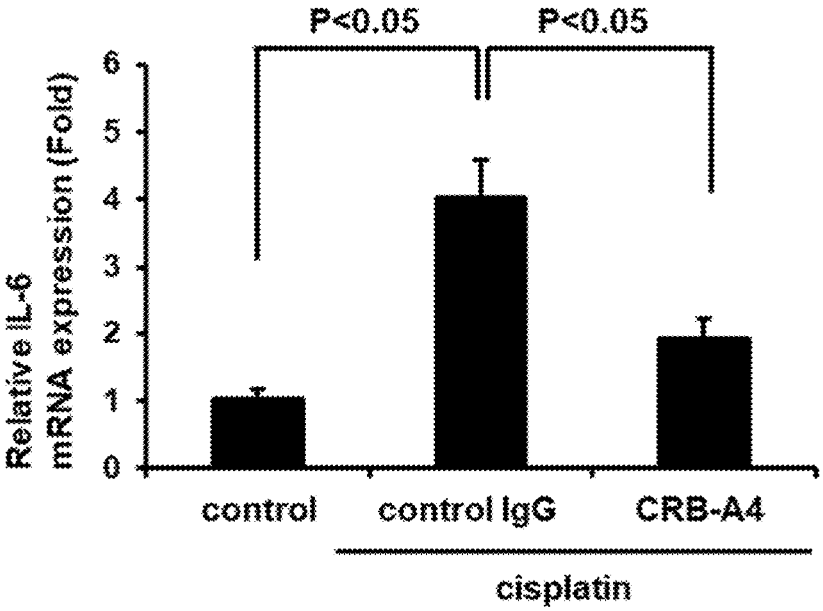
Figure 57C:
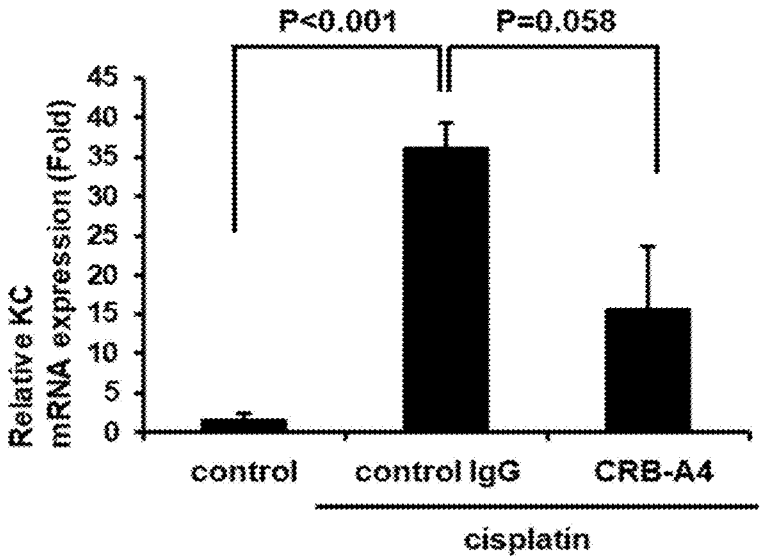
Figure 57D:
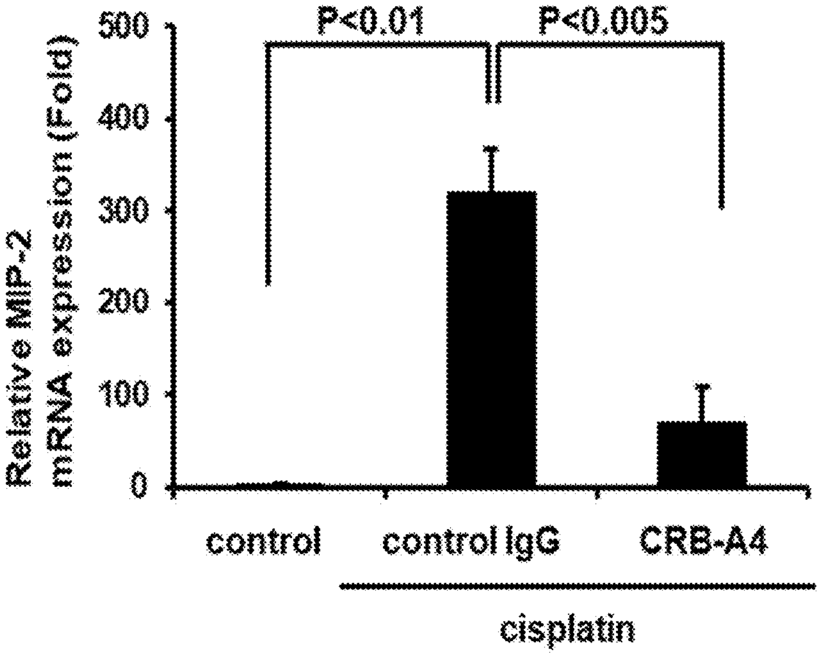
Figure 57E:
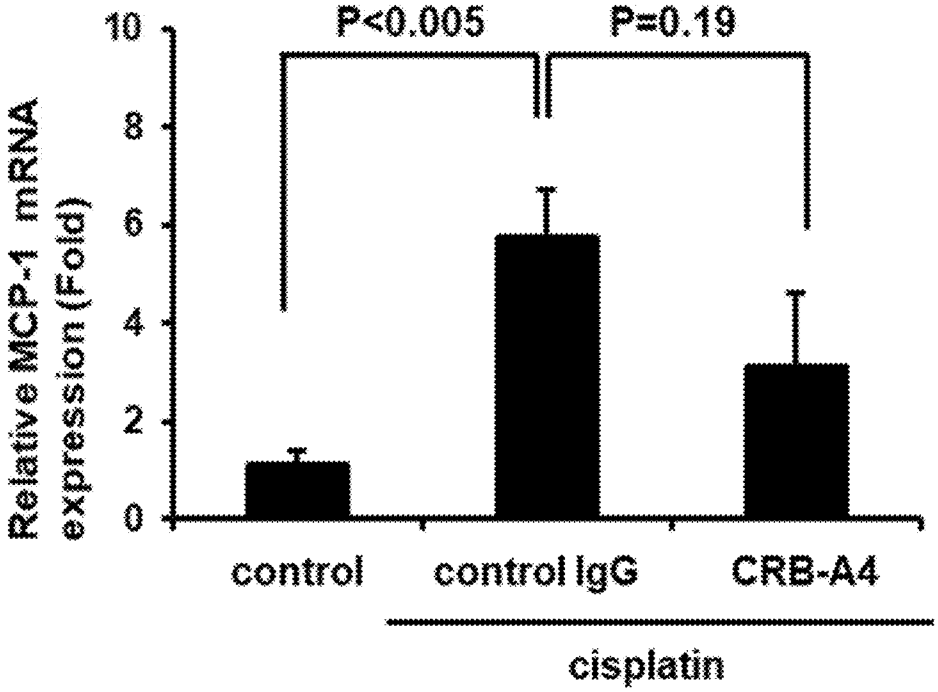

To investigate the therapeutic effect of SH3YL1 antibody on renal function, several markers were measured. First, kidney to body weight ratio associated with kidney hypertrophy was evaluated (10). Treatment of SH3YL1 antibodies attenuated the increase in kidney to body weight ratio upon cisplatin injection (FIG. 55A). Serum creatinine, blood urea nitrogen (BUN), and serum cystatin C are used as biomarkers of renal function, not only in AKI but also in Chronic Kidney Disease (CKD) (11-13). Cisplatin injection enhanced levels of these markers (FIGS. 55B-55D). However, the treatment of SH3YL1 antibody suppressed the levels of these markers (FIGS. 55B-55D). Severe tubular dysfunction was associated with chemotherapy. (14, 15). Therefore, albuminuria and albumin to creatinine ratio (ACR) was determined in the urine sample. Induction of urinary albumin and ACR by cisplatin was suppressed in response to treatment with SH3YL1 antibody (FIGS. 55E and 55F). Many clinical studies have shown that levels of urinary and plasma neutrophil gelatinase-associated lipocalin (NGAL) and kidney injury molecule-1 (KIM-1) are powerful diagnostic markers for AKI (15-19). To analyze kidney damage, NGAL and KIM-1 were measured in serum and urine using ELISA. The levels of urinary and serum NGAL and KIM-1 were elevated in response to cisplatin injection. However, treatment of SH3YL1 suppressed cisplatin-induced urinary and serum NGAL and KIM-1 levels (FIGS. 56A-56D). Taken together, it was shown that the SH3YL1 antibody protects against cisplatin-induced renal dysfunction.

Figure 58A:
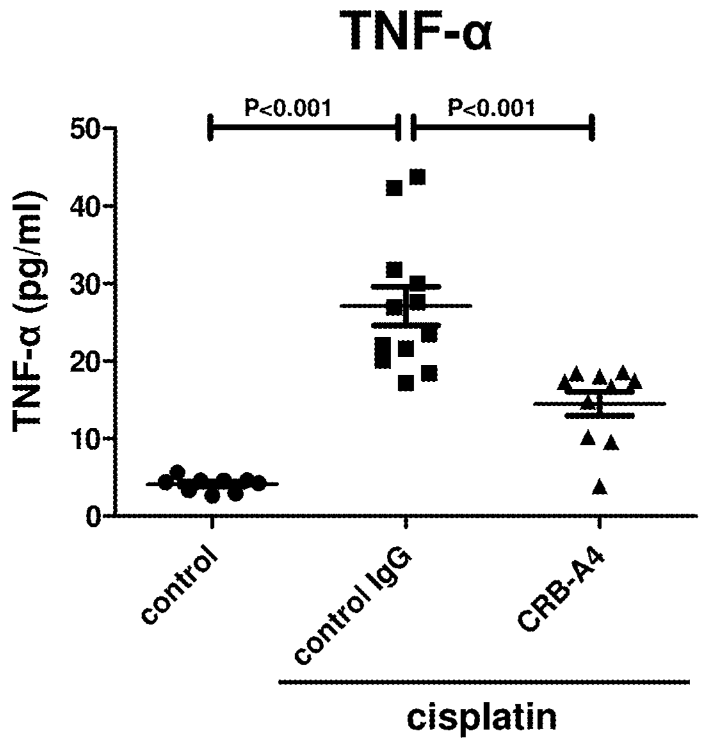
FIGS. 58A-58B. Treatment of SH3YL1 antibody attenuates TNF-α and KC secretion in cisplatin induced AKI mice serum. Serum TNF-α (FIG. 58A), KC (FIG. 58B) were detected using respective ELISA kits (N>9 per group, data shown as mean±SEM, P<0.001, P<0.05 as determined by student's t-test).
Figure 58B:
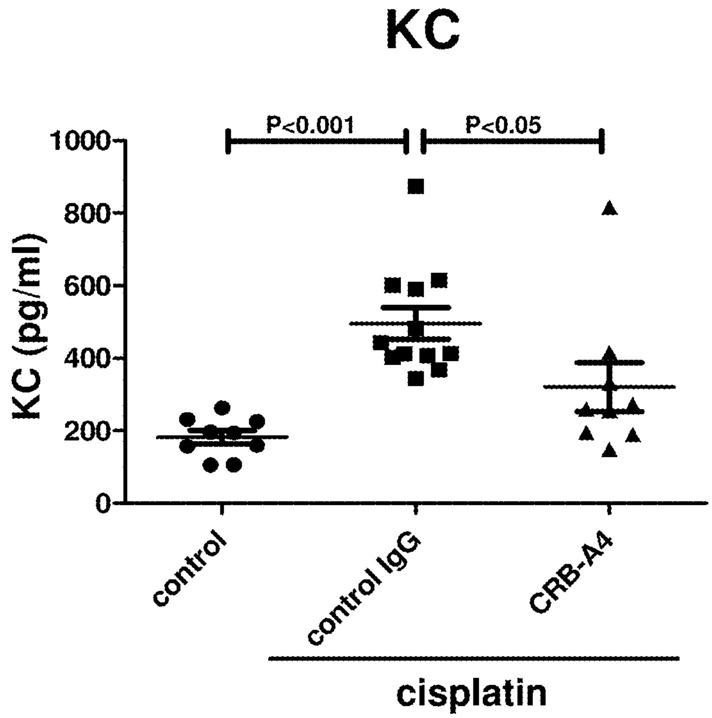

Treatment of SH3YL1 Antibody Attenuates Pro-Inflammatory Cytokine Production and Tubular Cell Damage in Cisplatin-Induced AKI Mice Many studies have shown that an increasing level of pro-inflammatory cytokines including TNF-α, IL-6, KC, MIP-2, MCP-1 is correlated with cisplatin-induced AKI (20-22). The mRNA levels of TNF-α, IL-6, KC, MIP-2, and MCP-1 expressions were increased in kidney tissue from cisplatin-injected mice. SH3YL1 antibody-treated mice reduced the expression level of cytokines (FIGS. 57A-57E). Moreover, the protein levels of TNF-α and KC in serum from SH3YL1 antibody-treated mice were suppressed, compared to control mice (FIGS. 58A-58B).

Figure 59:
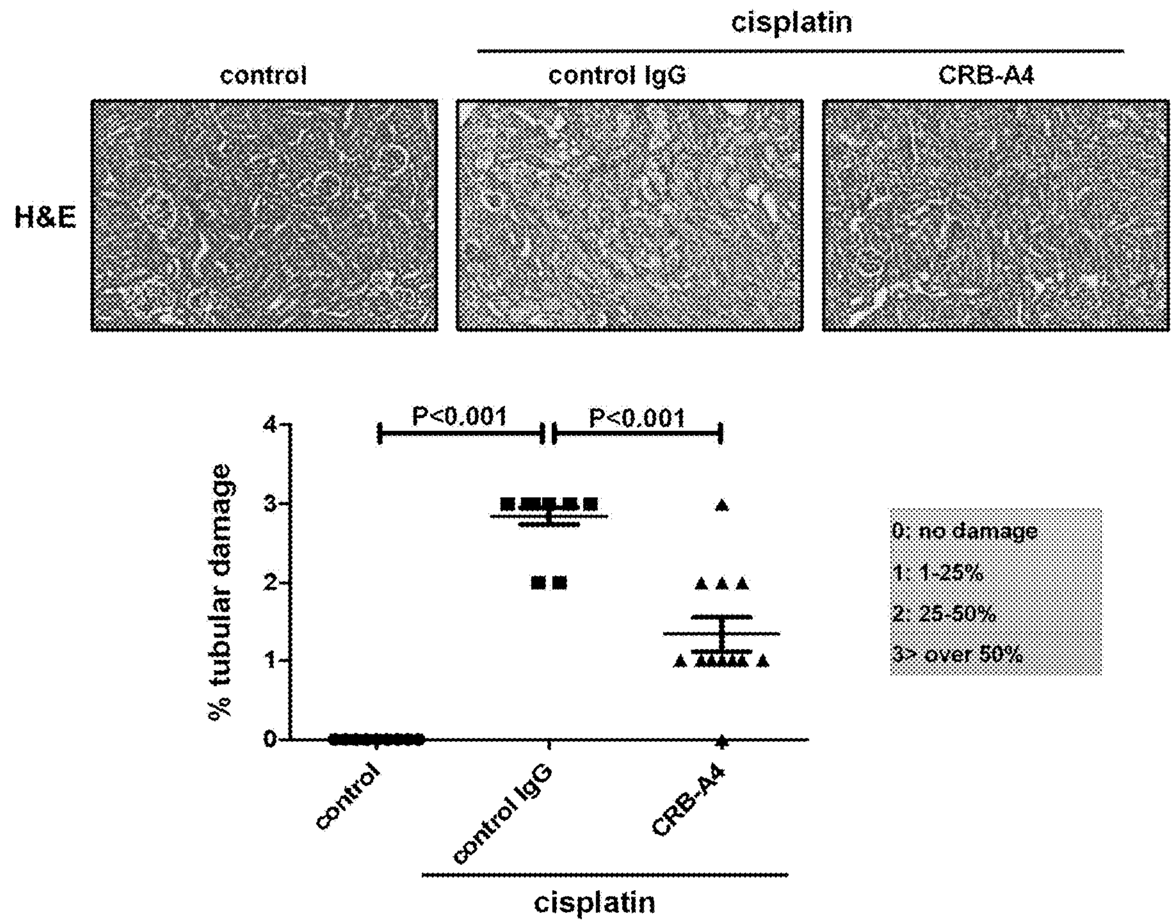
FIG. 59. SH3YL1 antibody protects against cisplatin-induced tubular cell damage.
Figure 60A:
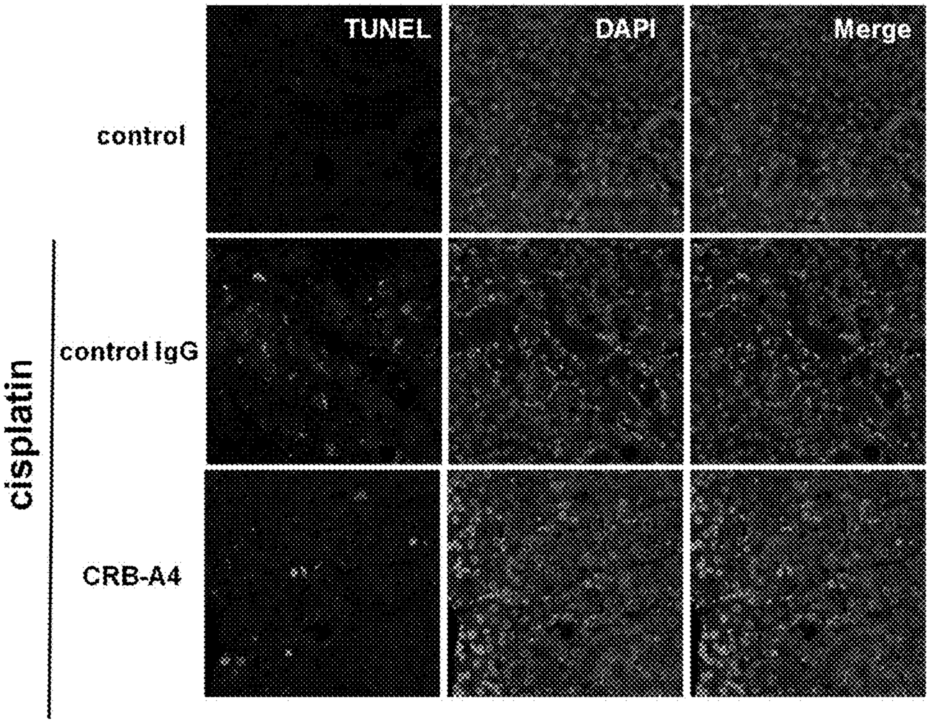
FIG. 60A-60B. SH3YL1 antibody can protect against cisplatin-induced apoptosis.
Figure 60B:
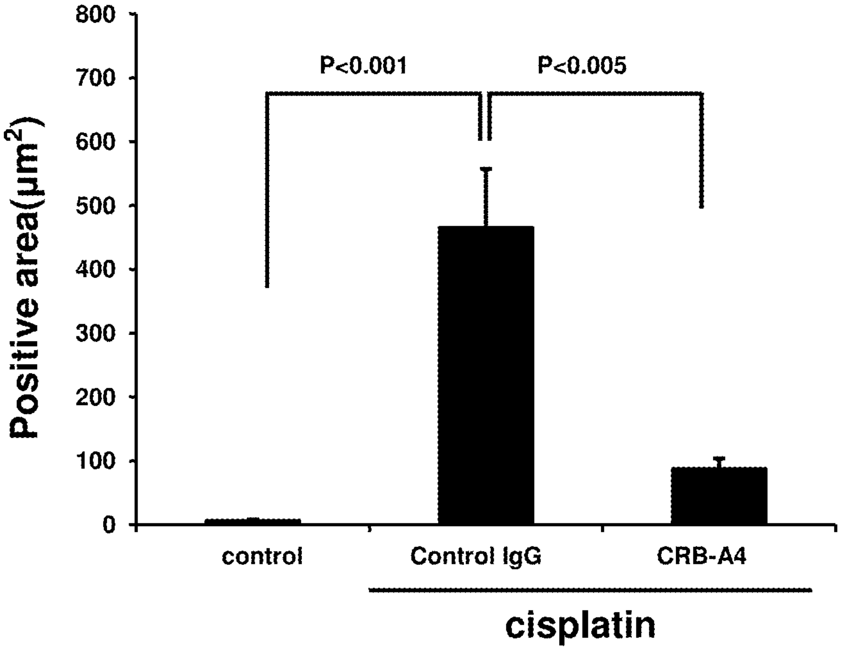

Cisplatin-induced renal damage was characterized by extensive tubular necrosis. Cisplatin-induced renal damage was significantly suppressed in SH3YL1 antibody-injected mice, compared to control mice (FIG. 59). Quantitative histological injury scoring from blinded grading of the severity of tubular injury was performed. The tubular injury score was attenuated in SH3YL1 antibody treated mice (FIG. 59). To evaluate the therapeutic effect of SH3YL1 antibodies in apoptosis of tubular cells, terminal deoxynucleotidyl transferase dUTP nick end labeling (TUNEL) staining was performed in kidney tissue. Treatment of SH3YL1 antibody suppressed cisplatin-induced apoptosis of tubular cells (FIGS. 60A-60B).

Example 3.3. Summary

Cisplatin showed a severe nephrotoxicity through apoptosis of renal tubular cells. Serum SH3YL1 level in cisplatin-induced AKI model was increased. Therefore, the therapeutic effect of SH3YL1 antibody to neutralize secreted SH3YL1 protein in a cisplatin-induced AKI model was explored. Injection of A4 SH3YL1 antibody into cisplatin-induced AKI mice resulted in reduced kidney injury markers (NGAL, KIM-1) and pro-inflammatory cytokine production (TNF-α, KC). SH3YL1 antibody protected against renal damage (serum creatinine, blood urea nitrogen, serum cystatin C, albuminuria) and apoptosis of tubular cell upon cisplatin injection. Thus, the SH3YL1 antibody shows good therapeutic efficacy in cisplatin-induced AKI.

Example 4. Inflammatory Bowel Disease (IBD)

Example 4.1. Materials and Methods

DSS-Induced Colitis in Mice and Treatments

An acute colitis model was induced by feeding C57BL/6 mice for 7 consecutive days with 2.5% dextran sodium sulfate (DSS, molecular weight: 36-50 kDa, MP Biomedicals, Solon, OH, USA) dissolved in drinking water and then changing with fresh water for three days. The mice were randomly divided into four groups (n=7 mice per group), including control, DSS, DSS+IgG1, and DSS+A4 (10 mg/kg). Antibody treatments were intravenously injected.

General Assessment of Colitis and Disease Activity Index (DAI)

The disease activity index (DAI) was comprehensively assessed by weight loss (0 point=none, 1 point=less than 10% weight loss, 2 points=10-20% weight loss, 3 points=more than 20% weight loss). Body weight was measured every other day. The total DAI score ranges from 0 (normal) to 10 (severe IBD).

Hematoxylin and Eosin (H&E)

Paraffin embedded mouse colon were cut in 4 μm thickness. H&E staining was performed using hematoxylin (Vector, Burlingame, CA, USA) and Eosin (sigma) with standard method.

Example 4.2. Results

Level of Serum SH3YL1 was Increased in IBD Model and Patients

Figure 61A:
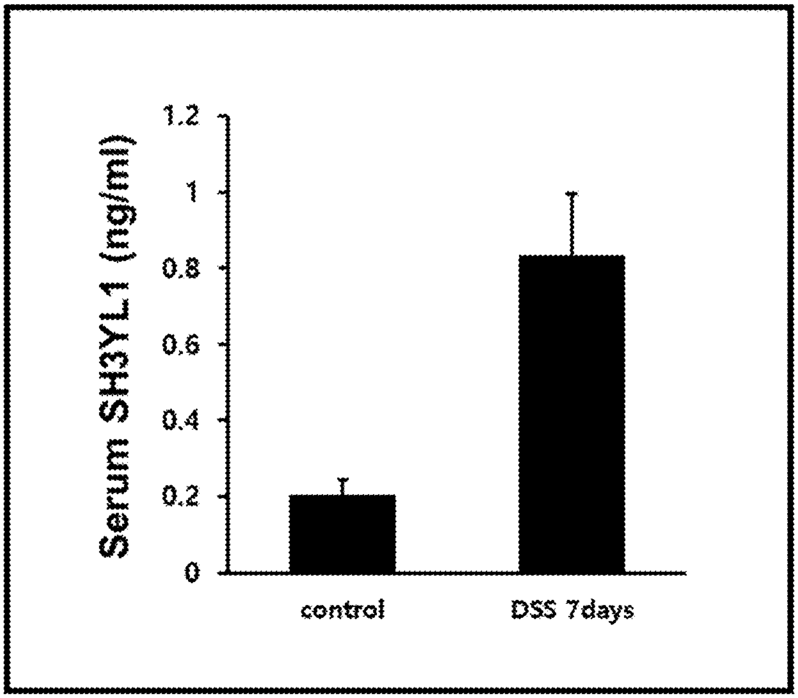
FIGS. 61A-61B. Level of serum SH3YL1 in DSS-induced colitis model and IBD patients.
Figure 61B:
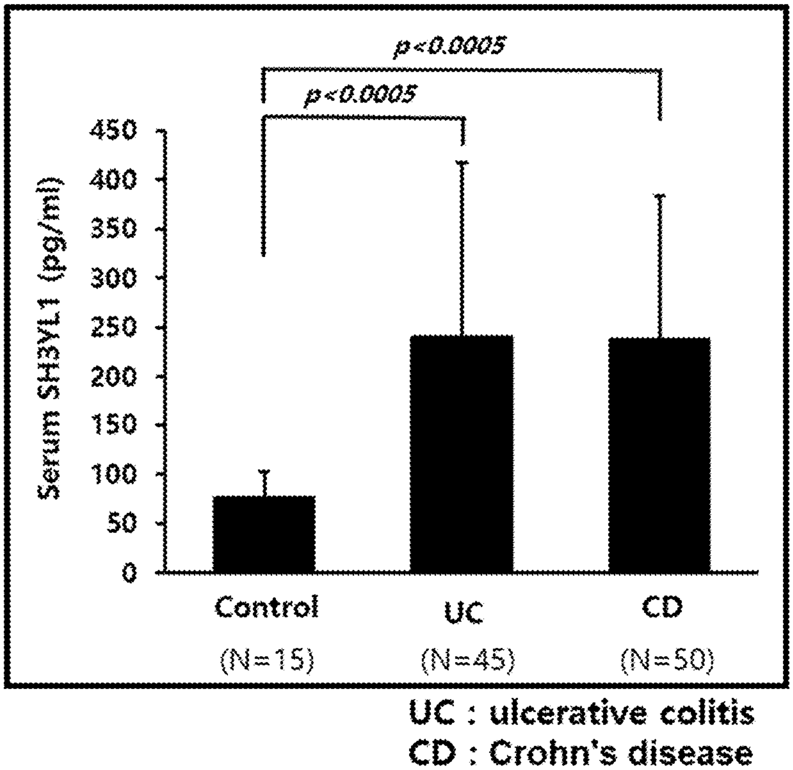

It was investigated whether SH3YL1 secretion is induced in a DSS-mediated IBD model. Stimulation of DSS for 7 days resulted in increased serum SH3YL1 (FIG. 61A). IBD patients are classified into two subtypes: ulcerative colitis (UC) and Crohn's disease (CD) (23-25). Serum SH3YL1 in 45 UC patients and 50 CD patients were evaluated. The level of serum SH3YL1 in UC and CD patients was higher than that in healthy persons (FIG. 61B).

Suppressive Effect of SH3YL1 Antibody on DSS-Induced IBD Model

Figure 62A:
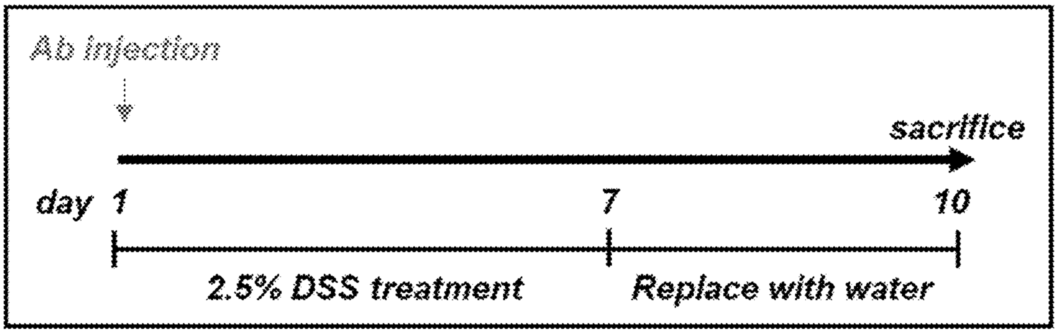
FIGS. 62A-62C. Preventive effect of A4 antibody in DSS-induced colitis model.
Figure 62B:
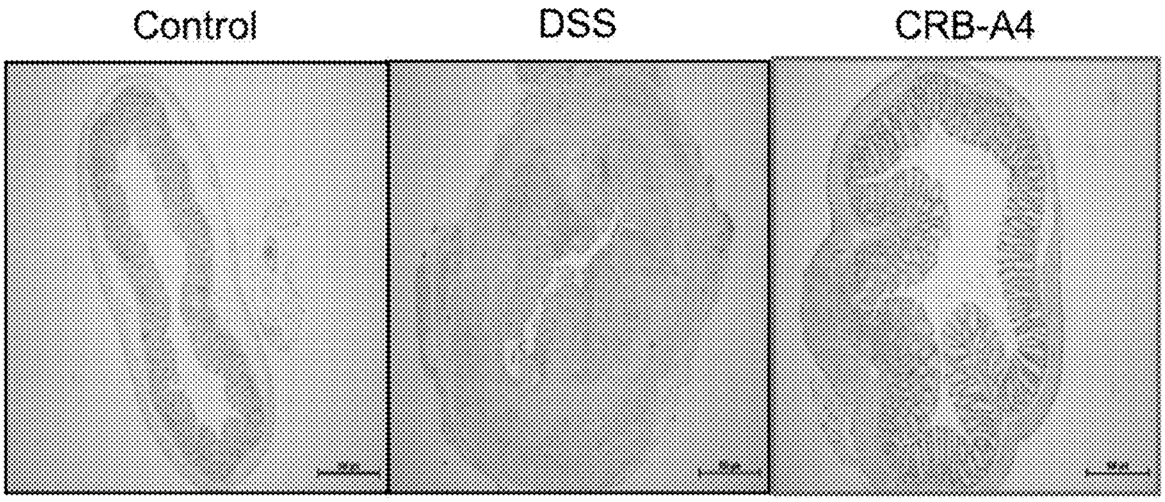
Figure 62C:
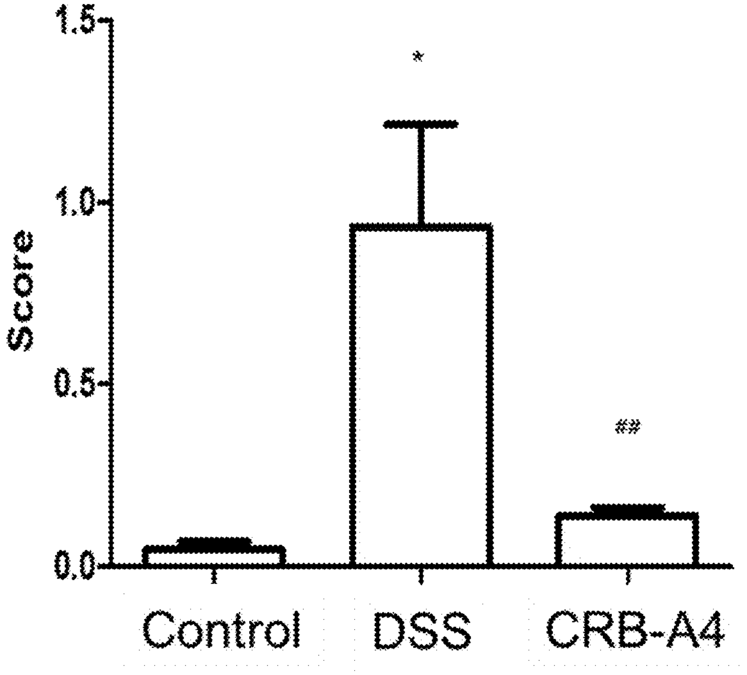
Figure 63A:
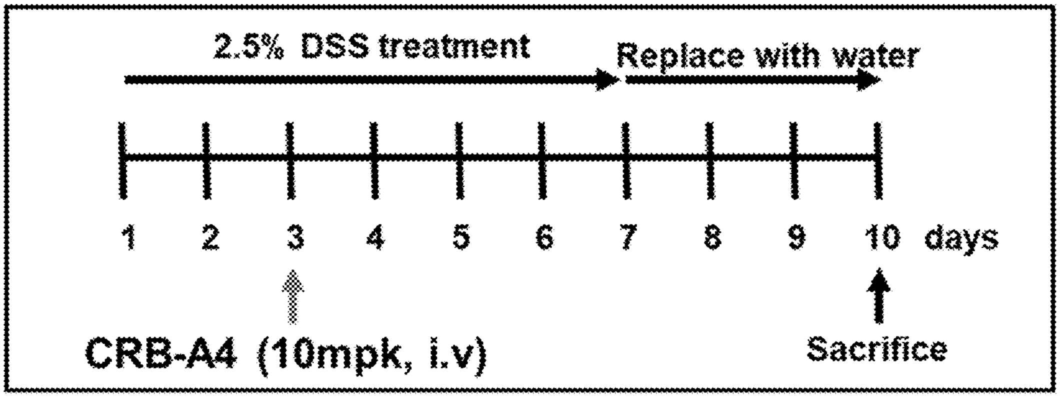
FIGS. 63A-63C. Therapeutic effect of A4 antibody on DSS-induced colitis model.
Figure 63B:
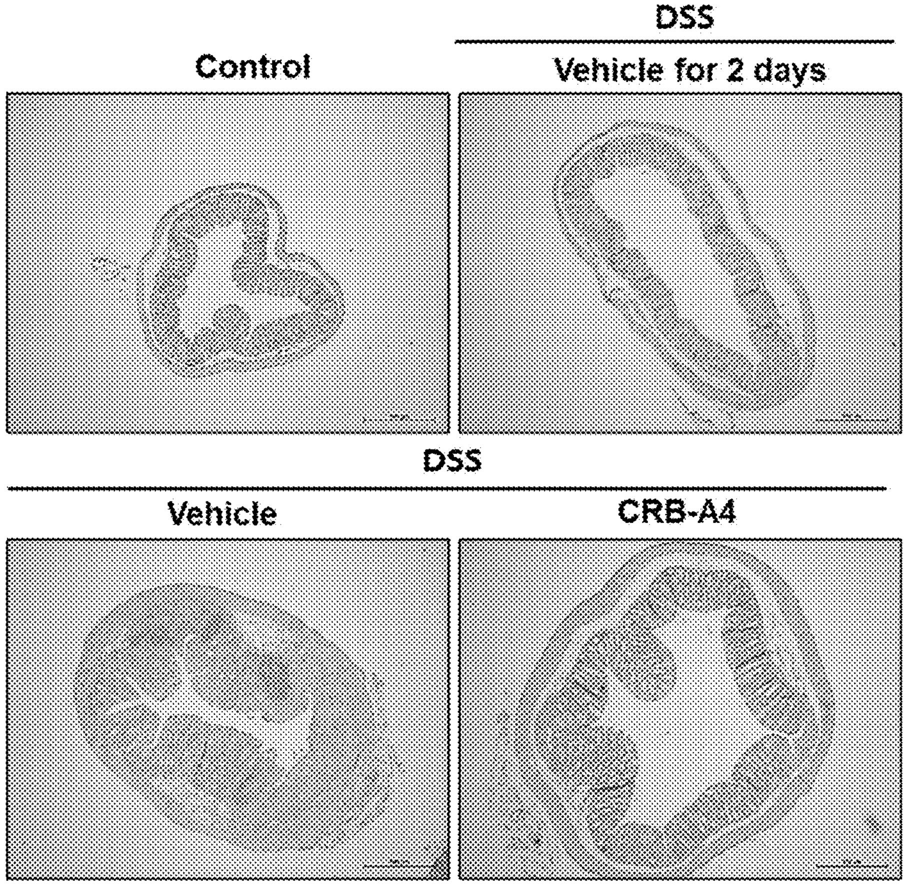
Figure 63C:
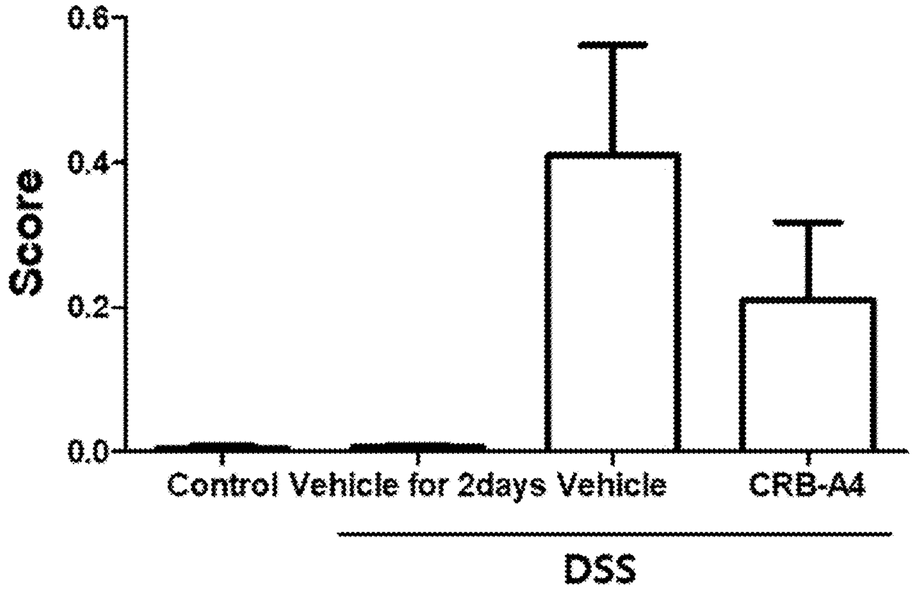

To investigate the preventive effect of SH3YL1 antibody on a DSS-induced IBD model (FIG. 62A), H&E staining of colon tissue was performed in IBD model. Treatment of DSS resulted in disruption of mucosal epithelial layers (FIGS. 62B and 62C). However, co-treatment of SH3YL1 antibody suppressed the loss of mucosal layers (FIGS. 62B and 62C). Next, the therapeutic effect of SH3YL1 antibody was validated. The model analyzes therapeutic effectiveness by injecting antibodies after pre-treatment with DSS for two days (FIG. 63A). Treatment of SH3YL1 antibody significantly inhibited the loss of mucosal layers, indicating that the SH3YL1 antibody has good therapeutic effect (FIGS. 63B and 63C).

Example 4.3. Summary

Based on the results, the level of serum SH3YL1 is induced in DSS-mediated IBD model and patients. SH3YL1 antibody suppressed the loss of mucosal layers in DSS-induced IBD model. Thus, the SH3YL1 antibody has good therapeutic effect for IBD.

REFERENCES

1. Bellomo, R., J. A. Kellum, and C. Ronco, Acute kidney injury. Lancet, 2012. 380 (9843):756-66.
2. Al-Jaghbeer, M., et al., Clinical Decision Support for In-Hospital AKI. J Am Soc Nephrol, 2018. 29(2):654-660.
3. Hoste, E. A., et al., Epidemiology of acute kidney injury in critically ill patients: the multinational AKI-EPI study. Intensive Care Med, 2015. 41(8):1411-23.
4. Ronco, C., R. Bellomo, and J. A. Kellum, Acute kidney injury. Lancet, 2019. 394(10212): 1949-1964.
5. Khwaja, A., KDIGO clinical practice guidelines for acute kidney injury. Nephron Clin Pract, 2012. 120(4):c179-84.
6. Zarogoulidis, K., et al., Treatment of non-small cell lung cancer (NSCLC). J Thorac Dis, 2013. 5 Suppl 4:S389-96.
7. Tanase, D. M., et al., The Predictive Role of the Biomarker Kidney Molecule-1 (KIM-1) in Acute Kidney Injury (AKI) Cisplatin-Induced Nephrotoxicity. Int J Mol Sci, 2019. 20(20).
8. Ismaili, N., M. Amzerin, and A. Flechon, Chemotherapy in advanced bladder cancer: current status and future. J Hematol Oncol, 2011. 4:35.
9. Miller, R. P., et al., Mechanisms of Cisplatin nephrotoxicity. Toxins (Basel), 2010. 2(11):2490-518.
10. Kanwar, Y. S., et al., Diabetic nephropathy: mechanisms of renal disease progression. Exp Biol Med (Maywood), 2008. 233(1):4-11.
11. Gowda, S., et al., Markers of renal function tests. N Am J Med Sci, 2010. 2(4):170-3.
12. Bellomo, R., et al., Acute kidney injury in sepsis. Intensive Care Med, 2017. 43(6):816-828.
13. Oh, S. W., The Cause and Treatment of Acute Kidney Injury. Korean J Med, 2019. 94(4):315-321.
14. Tugay, S., et al., Acute effects of gentamicin on glomerular and tubular functions in preterm neonates. Pediatr Nephrol, 2006. 21(10):1389-92.
15. Charlton, J. R., D. Portilla, and M. D. Okusa, A basic science view of acute kidney injury biomarkers. Nephrol Dial Transplant, 2014. 29(7):1301-11.
16. Mishra, J., et al., Neutrophil gelatinase-associated lipocalin (NGAL) as a biomarker for acute renal injury after cardiac surgery. Lancet, 2005. 365(9466):1231-8.
17. Haase, M., et al., Accuracy of neutrophil gelatinase-associated lipocalin (NGAL) in diagnosis and prognosis in acute kidney injury: a systematic review and meta-analysis. Am J Kidney Dis, 2009. 54(6):1012-24.
18. Sabbisetti, V. S., et al., Blood kidney injury molecule-1 is a biomarker of acute and chronic kidney injury and predicts progression to ESRD in type I diabetes. J Am Soc Nephrol, 2014. 25(10):2177-86.
19. Vaidya, V. S., et al., Kidney injury molecule-1 outperforms traditional biomarkers of kidney injury in preclinical biomarker qualification studies. Nat Biotechnol, 2010. 28(5):478-85.
20. Ozkok, A. and C. L. Edelstein, Pathophysiology of cisplatin-induced acute kidney injury. Biomed Res Int, 2014. 2014:967826.
21. Faubel, S., et al., Cisplatin-induced acute renal failure is associated with an increase in the cytokines interleukin (IL)-1beta, IL-18, IL-6, and neutrophil infiltration in the kidney. J Pharmacol Exp Ther, 2007. 322(1):8-15.
22. Liu, P., et al., Inhibition of CXCL1-CXCR2 axis ameliorates cisplatin-induced acute kidney injury by mediating inflammatory response. Biomed Pharmacother, 2020. 122:109693.
23. Plichta D R, Graham D B, Subramanian S, and Xavier R J, Therapeutic Opportunities in Inflammatory Bowel Disease: Mechanistic Dissection of Host-Microbiome Relationships. Cell 2019 178(5):1041-1056
24. Schirmer M, Garner A, Vlamakis H, and Xavier R J. Microbial genes and pathways in inflammatory bowel disease. Nat Rev Microbiol. 2019 17(8):497-511
25. Graham D B and Xavier R J. Pathway paradigms revealed from the genetics of inflammatory bowel disease. Nature. 2020 578(7796):527-539.

The foregoing description of the specific embodiments will so fully reveal the general nature of the invention that others can, by applying knowledge within the skill of the art, readily modify and/or adapt for various applications, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be herein incorporated by reference.

SEQUENCE LISTING

```
Sequence total quantity: 100
SEQ ID NO: 1            moltype = AA  length = 116
FEATURE                 Location/Qualifiers
REGION                  1..116
                        note = VH of A3 antibody
source                  1..116
                        mol_type = protein
                        organism = synthetic construct
SEQUENCE: 1
EVQLLESGGG LVQPGGSLRL SCAASGFTFS NYAMSWVRQA PGKGLEWVSV ISSDNSSTYY  60
ADSVKGRYTI SRDNSKNTLY LQMNSLRAED TAVYYCARVW RHFDYWGQGT LVTVSS      116

SEQ ID NO: 2            moltype = DNA  length = 349
FEATURE                 Location/Qualifiers
misc_feature            1..349
                        note = VH of A3 antibody
source                  1..349
                        mol_type = other DNA
                        organism = synthetic construct
SEQUENCE: 2
gaggtgcagc tgttggagtc tgggggaggc ttggtacagc ctggggggtc cctgagactc  60
tcctgtgcag cctctggatt cacctttagc aattatgcta tgagctgggt ccgccaggct  120
ccagggaagg ggctggagtg ggtctcagtg atctcttctg ataatagtag tacatattac  180
gctgattctg taaaaggtcg gtacaccatc tccagagaca attccaagaa cacgctgtat  240
ctgcaaatga acagcctgag agccgaggac acggccgtgt attactgtgc gagagtttgg  300
cggcatttcg actactgggg ccagggtaca ctggtcaccg tgagctcag              349

SEQ ID NO: 3            moltype = AA  length = 110
FEATURE                 Location/Qualifiers
REGION                  1..110
                        note = VL of A3 antibody
source                  1..110
                        mol_type = protein
                        organism = synthetic construct
SEQUENCE: 3
QSVLTQPPSA SGTPGQRVTI SCSGSSSNIG SNNVNWYQQL PGTAPKLLIY ADSHRPSGVP  60
DRFSGSKSGT SASLAISGLR SEDEADYYCA SWDSSLSGYV FGGGTKLTVL             110

SEQ ID NO: 4            moltype = DNA  length = 330
FEATURE                 Location/Qualifiers
misc_feature            1..330
                        note = VL of A3 antibody
source                  1..330
                        mol_type = other DNA
                        organism = synthetic construct
SEQUENCE: 4
cagtctgtgc tgactcagcc accctcagcg tctgggaccc ccgggcagag ggtcaccatc  60
tcttgtagtg gctcttcatc taatattggc agtaataatg tcaactggta ccagcagctc  120
ccaggaacgg ctcccaaact cctcatctat gctgatagtc atcggccaag cggggtccct  180
gaccgattct ctggctccaa gtctggcacc tcagcctccc tggccatcag tgggctccgg  240
tccgaggatg aggctgatta ttactgtgct tcttgggatt ctagcctgag tggttatgtc  300
ttcggcggag gcaccaagct gacggtccta                                   330

SEQ ID NO: 5            moltype = AA  length = 116
FEATURE                 Location/Qualifiers
REGION                  1..116
                        note = VH of A4 antibody
source                  1..116
                        mol_type = protein
                        organism = synthetic construct
SEQUENCE: 5
EVQLLESGGG LVQPGGSLRL SCAASGFTFS NYYMSWVRQA PGKGLEWVSA ISHNNSNTYY  60
ADSVKGRFTI SRDNSKNTLY LQMNSLRAED TAVYYCARKF SFFDYWGQGT LVTVSS      116

SEQ ID NO: 6            moltype = DNA  length = 348
FEATURE                 Location/Qualifiers
misc_feature            1..348
                        note = VH of A4 antibody
```

```
source                  1..348
                        mol_type = other DNA
                        organism = synthetic construct
SEQUENCE: 6
gaggtgcagc tgttggagtc cgggggaggc ttggtacagc ctggggggtc cctgagactc  60
tcctgtgcag cctctggatt cacctttagc aattattata tgagctgggt ccgccaggct  120
ccagggaagg ggctggagtg ggtctcagcg atctctcata ataatagtaa tacatattac  180
gctgattctg taaaaggtcg gttcaccatc tccagagaca attccaagaa cacgctgtat  240
ctgcaaatga acagcctgag agccgaggac acggccgtgt attactgtgc gagaaagttt  300
tctttttcg actactgggg ccagggtaca ctggtcaccg tgagctca            348

SEQ ID NO: 7            moltype = AA  length = 110
FEATURE                 Location/Qualifiers
REGION                  1..110
                        note = VL of A4 antibody
source                  1..110
                        mol_type = protein
                        organism = synthetic construct
SEQUENCE: 7
QSVLTQPPSA SGTPGQRVTI SCSGSSSNIG SNYVSWYQQL PGTAPKLLIY ANSHRPSGVP  60
DRFSGSKSGT SASLAISGLR SEDEADYYCG AWDSSLNGYV FGGGTKLTVL             110

SEQ ID NO: 8            moltype = DNA  length = 330
FEATURE                 Location/Qualifiers
misc_feature            1..330
                        note = VL of A4 antibody
source                  1..330
                        mol_type = other DNA
                        organism = synthetic construct
SEQUENCE: 8
cagtctgtgc tgactcagcc accctcagcg tctgggaccc ccgggcagag ggtcaccatc  60
tcttgtagtg gctcttcatc taatattggc agtaattatg tctcctggta ccagcagctc  120
ccaggaacgg cccccaaact cctcatctat gctaatagtc atcggccaag cggggtccct  180
gaccgattct ctggctccaa gtctggcacc tcagcctccc tggccatcag tgggctccgg  240
tccgaggatg aggctgatta ttactgtggt gcttgggatt ctagcctgaa tggttatgtc  300
ttcggcggag gcaccaagct gacggtccta                                   330

SEQ ID NO: 9            moltype = AA  length = 330
FEATURE                 Location/Qualifiers
REGION                  1..330
                        note = CH of A3, A4, and S4A antibodies
source                  1..330
                        mol_type = protein
                        organism = synthetic construct
SEQUENCE: 9
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 10           moltype = AA  length = 106
FEATURE                 Location/Qualifiers
REGION                  1..106
                        note = CL of A3, A4, and S4A antibodies
source                  1..106
                        mol_type = protein
                        organism = synthetic construct
SEQUENCE: 10
GQPKAAPSVT LFPPSSEELQ ANKATLVCLI SDFYPGAVTV AWKADSSPVK AGVETTTPSK  60
QSNNKYAASS YLSLTPEQWK SHKSYSCQVT HEGSTVEKTV APAECS                 106

SEQ ID NO: 11           moltype = AA  length = 342
FEATURE                 Location/Qualifiers
REGION                  1..342
                        note = SH3YL1
source                  1..342
                        mol_type = protein
                        organism = synthetic construct
SEQUENCE: 11
MNNPIPSNLK SEAKKAAKIL REFTEITSRN GPDKIIPAHV IAKAKGLAIL SVIKAGFLVT  60
ARGGSGIVVA RLPDGKWSAP SAIGIAGLGG GFEIGIEVSD LVIILNYDRA VEAFAKGGNL  120
TLGGNLTVAV GPLGRNLEGN VALRSSAAVF TYCKSRGLFA GVSLEGSCLI ERKETNRKFY  180
CQDIRAYDIL FGDTPRPAQA EDLYEILDSF TEKYENEGQR INARKAAREQ RKSSAKELPP  240
KPLSRPQQSS APVQLNSGSQ SNRNEYKLYP GLSSYHERVG NLNQPIEVTA LYSFEGQQPG  300
DLNFQAGDRI TVISKTDSHF DWWEGKLRGQ TGIFPANYVT MN                     342

SEQ ID NO: 12           moltype = DNA  length = 1029
```

```
FEATURE                Location/Qualifiers
misc_feature           1..1029
                       note = SH3YL1
source                 1..1029
                       mol_type = other DNA
                       organism = synthetic construct
SEQUENCE: 12
atgaataacc ctataccttc caatttgaaa tcagaagcaa aaaaggctgc caaaatatta  60
agagaattca cagaaataac ttccagaaat ggacctgata agatcattcc tgctcacgta  120
attgcgaagg ctaaaggcct tgcaattctg tctgtgatca aagccgggtt cctggtgact  180
gccagaggag gcagcgggat tgtagtggcg cgccttccag atggaaaatg gtctgcaccc  240
tcagccattg ggatagctgg ccttggtgga ggatttgaaa taggaattga ggtatcagac  300
ttggtgataa ttctgaatta tgaccgtgct gtagaagctt ttgcaaaagg cggaaatctg  360
accctcggag ggaacttgac tgtggcggtt gggcccttgg gaaggaactt ggaaggaaac  420
gtggccctga gaagctccgc tgccgtcttc acgtactgca agtcaagggg actctttgca  480
ggcgtgtctt tagaagggag ctgtttgatt gaaaggaaag aaactaatag aaaattttat  540
tgtcaagata tccgagctta tgacatttta tttggagata caccgcggcc tgctcaagcc  600
gaagatcttt atgaaattct tgattccttt actgaaaagt atgaaaatga aggacaacga  660
atcaatgcaa gaaaagcagc aagggagcag aggaagtctt ctgctaaaga attacctcca  720
aagccattgt caagaccaca gcagtcatct gcaccagtcc agctgaactc tggctctcaa  780
agtaacagaa atgaatataa gctctatcct ggactttcca gctatcatga gagagttggc  840
aatttgaatc aacccataga agtgacagcg ctgtattcat ttgaaggaca gcagcctggg  900
gatttgaatt ttcaagctgg agacagaatc acagttatat caaaaacaga ttcacatttt  960
gattggtggg aaggaaaact tcgaggtcaa actggcattt ttccagccaa ctacgtaacc  1020
atgaattaa                                                         1029

SEQ ID NO: 13          moltype = AA  length = 5
FEATURE                Location/Qualifiers
REGION                 1..5
                       note = VH CDR1 of A3 and 4G4 antibodies
source                 1..5
                       mol_type = protein
                       organism = synthetic construct
SEQUENCE: 13
NYAMS                                                             5

SEQ ID NO: 14          moltype = AA  length = 17
FEATURE                Location/Qualifiers
REGION                 1..17
                       note = VH CDR2 of A3 antibody
source                 1..17
                       mol_type = protein
                       organism = synthetic construct
SEQUENCE: 14
VISSDNSSTY YADSVKG                                                17

SEQ ID NO: 15          moltype = AA  length = 7
FEATURE                Location/Qualifiers
REGION                 1..7
                       note = VH CDR3 of A3 antibody
source                 1..7
                       mol_type = protein
                       organism = synthetic construct
SEQUENCE: 15
VWRHFDY                                                           7

SEQ ID NO: 16          moltype = AA  length = 13
FEATURE                Location/Qualifiers
REGION                 1..13
                       note = VL CDR1 of A3 antibody
source                 1..13
                       mol_type = protein
                       organism = synthetic construct
SEQUENCE: 16
SGSSSNIGSN NVN                                                    13

SEQ ID NO: 17          moltype = AA  length = 7
FEATURE                Location/Qualifiers
REGION                 1..7
                       note = VL CDR2 of A3 antibody
source                 1..7
                       mol_type = protein
                       organism = synthetic construct
SEQUENCE: 17
ADSHRPS                                                           7

SEQ ID NO: 18          moltype = AA  length = 11
FEATURE                Location/Qualifiers
REGION                 1..11
```

```
                        note = VL CDR3 of A3 antibody
source                  1..11
                        mol_type = protein
                        organism = synthetic construct
SEQUENCE: 18
ASWDSSLSGY V                                                      11

SEQ ID NO: 19           moltype = AA  length = 5
FEATURE                 Location/Qualifiers
REGION                  1..5
                        note = VH CDR1 of A4 antibody
source                  1..5
                        mol_type = protein
                        organism = synthetic construct
SEQUENCE: 19
NYYMS                                                             5

SEQ ID NO: 20           moltype = AA  length = 17
FEATURE                 Location/Qualifiers
REGION                  1..17
                        note = VH CDR1 of A4 antibody
source                  1..17
                        mol_type = protein
                        organism = synthetic construct
SEQUENCE: 20
AISHNNSNTY YADSVKG                                                17

SEQ ID NO: 21           moltype = AA  length = 7
FEATURE                 Location/Qualifiers
REGION                  1..7
                        note = VH CDR3 of A4 antibody
source                  1..7
                        mol_type = protein
                        organism = synthetic construct
SEQUENCE: 21
KFSFFDY                                                           7

SEQ ID NO: 22           moltype = AA  length = 13
FEATURE                 Location/Qualifiers
REGION                  1..13
                        note = VL CDR1 of A4 antibody
source                  1..13
                        mol_type = protein
                        organism = synthetic construct
SEQUENCE: 22
SGSSSNIGSN YVS                                                    13

SEQ ID NO: 23           moltype = AA  length = 7
FEATURE                 Location/Qualifiers
REGION                  1..7
                        note = VL CDR2 of A4 antibody
source                  1..7
                        mol_type = protein
                        organism = synthetic construct
SEQUENCE: 23
ANSHRPS                                                           7

SEQ ID NO: 24           moltype = AA  length = 11
FEATURE                 Location/Qualifiers
REGION                  1..11
                        note = VL CDR3 of A4 antibody
source                  1..11
                        mol_type = protein
                        organism = synthetic construct
SEQUENCE: 24
GAWDSSLNGY V                                                      11

SEQ ID NO: 25           moltype = AA  length = 8
FEATURE                 Location/Qualifiers
REGION                  1..8
                        note = epitope in SH3YL1 for A3 antibody
source                  1..8
                        mol_type = protein
                        organism = synthetic construct
SEQUENCE: 25
DSHFDWWE                                                          8

SEQ ID NO: 26           moltype = AA  length = 8
FEATURE                 Location/Qualifiers
```

```
REGION                  1..8
                        note = epitope in SH3YL1 for A4 antibody
source                  1..8
                        mol_type = protein
                        organism = synthetic construct
SEQUENCE: 26
LYEILDSF                                                            8

SEQ ID NO: 27           moltype = DNA  length = 36
FEATURE                 Location/Qualifiers
misc_feature            1..36
                        note = VH Forward primer
source                  1..36
                        mol_type = other DNA
                        organism = synthetic construct
SEQUENCE: 27
ttctccagcg cttattccga ggtgcagctg ttggag                             36

SEQ ID NO: 28           moltype = DNA  length = 30
FEATURE                 Location/Qualifiers
misc_feature            1..30
                        note = VH Reverse primer
source                  1..30
                        mol_type = other DNA
                        organism = synthetic construct
SEQUENCE: 28
cttggtgcta gctgagctca cggtgaccag                                    30

SEQ ID NO: 29           moltype = DNA  length = 36
FEATURE                 Location/Qualifiers
misc_feature            1..36
                        note = VL forward primer
source                  1..36
                        mol_type = other DNA
                        organism = synthetic construct
SEQUENCE: 29
ttctccagcg cttattccca gtctgtgctg actcag                             36

SEQ ID NO: 30           moltype = DNA  length = 24
FEATURE                 Location/Qualifiers
misc_feature            1..24
                        note = VL reverse primer
source                  1..24
                        mol_type = other DNA
                        organism = synthetic construct
SEQUENCE: 30
gggctgacct aggaccgtca gctt                                          24

SEQ ID NO: 31           moltype = AA  length = 118
FEATURE                 Location/Qualifiers
REGION                  1..118
                        note = VH of S4A antibody
source                  1..118
                        mol_type = protein
                        organism = synthetic construct
SEQUENCE: 31
EVQLLESGGG LVQPGGSLRL SCAASGFTFS SYSMNWVRQA PGKGLEWVSW ISPNSGSTDY  60
AQKFQGRFTI SRDNSKNTLY LQMNSLRAED TAVYYCARTP PGTPFDYWGQ GTLVTVSS    118

SEQ ID NO: 32           moltype = DNA  length = 354
FEATURE                 Location/Qualifiers
misc_feature            1..354
                        note = VH of S4A antibody
source                  1..354
                        mol_type = other DNA
                        organism = synthetic construct
SEQUENCE: 32
gaagtgcagc tgctggaaag tggaggtgga ctggtgcagc ctggcggcag cctgcgcctg  60
agctgtgccg ccagcggatt caccttcagc agctatagca tgaactgggt tcgccaagca  120
cctggcaaag gcctggaatg ggtgagctgg atcagcccta acagcggcag caccgattat  180
gcccagaaat ttcagggccg ctttaccatc agccgcgata acagcaaaaa caccctgtat  240
ctgcagatga acagcctgcg cgccgaggac accgcagtct actactgtgc ccgcacccct  300
cctggcaccc cttttgatta ttggggacaa ggtactctgg tgaccgtgag cagt        354

SEQ ID NO: 33           moltype = AA  length = 107
FEATURE                 Location/Qualifiers
REGION                  1..107
                        note = VL of S4A antibody
source                  1..107
```

```
                         mol_type = protein
                         organism = synthetic construct
SEQUENCE: 33
QSVLTQPPSA SGTPGQRVTI SCSGNNIGSK SVHWYQQLPG TAPRLLIYST SNKHSGVPDR  60
FSGSKSGTSA SLAISGLHSE DEADYYCSSY TSSGTRVFGG GTKLTVL               107

SEQ ID NO: 34            moltype = DNA  length = 321
FEATURE                  Location/Qualifiers
misc_feature             1..321
                         note = VL of S4A
source                   1..321
                         mol_type = other DNA
                         organism = synthetic construct
SEQUENCE: 34
cagagcgtgc tgacccagcc tcctagcgcc tccggtacac caggacagcg cgtgactatt  60
agctgtagcg gcaacaacat cggcagcaaa agcgtgcatt ggtaccagca actgcctgga  120
actgcaccta ggctgctgat ctatagcacc agcaacaaac atagcggcgt tcctgatcgc  180
tttagcggta gcaaatcagg caccagcgcc agcctggcca tcagcggcct tcactccgaa  240
gatgaagccg attattattg tagcagctat accagcagcg gcacccgcgt gtttggtggc  300
ggtaccaagc tgaccgtcct a                                            321

SEQ ID NO: 35            moltype = AA  length = 119
FEATURE                  Location/Qualifiers
REGION                   1..119
                         note = VH of 4F9 antibody
source                   1..119
                         mol_type = protein
                         organism = synthetic construct
SEQUENCE: 35
EVQLVESGGG LVQPGGSLRL SCAASGFTFS DYAMSWVRQA PGKGLEWVSA IKSSGSSTYY  60
ADSVKGRFTI SRDNSKNTLY LQMNSLRAED TAVYYCAKAE YEYLAFDIWG QGTLVTVSS   119

SEQ ID NO: 36            moltype = DNA  length = 357
FEATURE                  Location/Qualifiers
misc_feature             1..357
                         note = VH of 4F9 antibody
source                   1..357
                         mol_type = other DNA
                         organism = synthetic construct
SEQUENCE: 36
gaagtacagt tggtcgaaag tggcggtggc ctcgtgcaac cgggtggttc actgcgtctg  60
agctgcgccg cctcgggttt tactttctct gattatgcaa tgtcttgggt tcgtcaggcg  120
ccgggcaagg gtctcgaatg ggtttcagca atcaaatctt ctggttcttc tacttactat  180
gccgattcag tgaagggtcg ctttaccatt tcccgtgaca actctaagaa tactctgtat  240
ctgcagatga actcgctgcg tgccgaagac acggccgtct attattgcgc caaagcagaa  300
tacgaatacc tggcattcga tatctggggt cagggcactt tagtgaccgt ctcatcg     357

SEQ ID NO: 37            moltype = AA  length = 107
FEATURE                  Location/Qualifiers
REGION                   1..107
                         note = VL of 4F9 antibody
source                   1..107
                         mol_type = protein
                         organism = synthetic construct
SEQUENCE: 37
DIQMTQSPSS LSASVGDRVT ITCRASQDIS SWLNWYQQKP GKAPKLLIYA TSTLQSGVPS  60
RFSGSGSGTD FTLTISSLQP EDFATYYCQQ SYSSPWTFGQ GTKVEIK               107

SEQ ID NO: 38            moltype = DNA  length = 321
FEATURE                  Location/Qualifiers
misc_feature             1..321
                         note = VL of 4F9
source                   1..321
                         mol_type = other DNA
                         organism = synthetic construct
SEQUENCE: 38
gacattcaaa tgacgcagag tccctcctca ctgagtgcta gcgtgggcga tcgtgtgaca  60
attacttgtc gcgctagcca ggatatctct tcttggctga actggtatca gcagaaaccg  120
ggcaaggcgc caaaattgct gatttacgca acttccactc tgcagtctgg tgtaccgtcc  180
cgtttctctg gcagcggttc tggtacggat tttaccctga ccatctcaag cctccagcct  240
gaagattttg ccacctatta ttgtcagcaa tcttactctt ctccgtggac gttcgggcag  300
ggaactaaag tggaaattaa a                                            321

SEQ ID NO: 39            moltype = AA  length = 117
FEATURE                  Location/Qualifiers
REGION                   1..117
                         note = VH of 4F10 antibody
source                   1..117
                         mol_type = protein
```

```
                         organism = synthetic construct
SEQUENCE: 39
EVQLVESGGG LVQPGGSLRL SCAASGFTFS DYAMSWVRQA PGKGLEWVSA IYSTGSSTYY  60
ADSVKGRFTI SRDNSKNTLY LQMNSLRAED TAVYYCAKVG WYLFDYWGQG TLVTVSS     117

SEQ ID NO: 40            moltype = DNA  length = 351
FEATURE                  Location/Qualifiers
misc_feature             1..351
                         note = VH of 4F10 antibody
source                   1..351
                         mol_type = other DNA
                         organism = synthetic construct
SEQUENCE: 40
gaagtacagt tggtcgaaag tggcggtggc ctcgtgcaac cgggtggttc actgcgtctg  60
agctgcgccg cctcgggttt tactttctct gattatgcaa tgtcttgggt tcgtcaggcg  120
ccgggcaagg gtctcgaatg ggtttcagca atctactcta ctggttcttc tacttactat  180
gccgattcag tgaagggtcg ctttaccatt tcccgtgaca actctaagaa tactctgtat  240
ctgcagatga actcgctgcg tgccgaagac acggccgtct attattgcgc caaagttggt  300
tggtacctgt ttgattactg gggtcagggt actctggtga ccgtctcatc g           351

SEQ ID NO: 41            moltype = AA  length = 107
FEATURE                  Location/Qualifiers
REGION                   1..107
                         note = VL of 4F10 antibody
source                   1..107
                         mol_type = protein
                         organism = synthetic construct
SEQUENCE: 41
DIQMTQSPSS LSASVGDRVT ITCRASQSIS RYLNWYQQKP GKAPKLLIYA TSRLQSGVPS  60
RFSGSGSGTD FTLTISSLQP EDFATYYCQQ SYSSPWTFGQ GTKVEIK                107

SEQ ID NO: 42            moltype = DNA  length = 321
FEATURE                  Location/Qualifiers
misc_feature             1..321
                         note = VL of 4F10 antibody
source                   1..321
                         mol_type = other DNA
                         organism = synthetic construct
SEQUENCE: 42
gacattcaaa tgacgcagag tccctcctca ctgagtgcta gcgtgggcga tcgtgtgaca  60
attacttgtc gcgctagcca gtctatctct cgttacctga actggtatca gcagaaaccg  120
ggcaaggcgc caaaattgct gatttacgca acttcccgtc tgcagtctgg tgtaccgtcc  180
cgtttctctg gcagcggttc tggtacggat tttaccctga ccatctcaag cctccagcct  240
gaagattttg ccacctatta ttgtcagcaa tcttactctt ctccgtggac gttcgggcag  300
ggaactaaag tggaaattaa a                                            321

SEQ ID NO: 43            moltype = AA  length = 119
FEATURE                  Location/Qualifiers
REGION                   1..119
                         note = VH of 5D5 antibody
source                   1..119
                         mol_type = protein
                         organism = synthetic construct
SEQUENCE: 43
EVQLVESGGG LVQPGGSLRL SCAASGFTFS DYAMSWVRQA PGKGLEWVSS ISSTGSSTYY  60
ADSVKGRFTI SRDNSKNTLY LQMNSLRAED TAVYYCAKVL YEYLYFDYWG QGTLVTVSS   119

SEQ ID NO: 44            moltype = DNA  length = 357
FEATURE                  Location/Qualifiers
misc_feature             1..357
                         note = VH of 5D5 antibody
source                   1..357
                         mol_type = other DNA
                         organism = synthetic construct
SEQUENCE: 44
gaagtacagt tggtcgaaag tggcggtggc ctcgtgcaac cgggtggttc actgcgtctg  60
agctgcgccg cctcgggttt tactttctct gattatgcaa tgtcttgggt tcgtcaggcg  120
ccgggcaagg gtctcgaatg ggtttcatct atctcttcta ctggttctac tacttactat  180
gccgattcag tgaagggtcg ctttaccatt tcccgtgaca actctaagaa tactctgtat  240
ctgcagatga actcgctgcg tgccgaagac acggccgtct attattgcgc caaagttctg  300
tacgaatacc tgtacttcga ttactggggt cagggcactt tagtgaccgt ctcatcg     357

SEQ ID NO: 45            moltype = AA  length = 107
FEATURE                  Location/Qualifiers
REGION                   1..107
                         note = VL of 5D5 antibody
source                   1..107
                         mol_type = protein
                         organism = synthetic construct
```

```
SEQUENCE: 45
DIQMTQSPSS LSASVGDRVT ITCRASQDIR NWLNWYQQKP GKAPKLLIYA ASSLQSGVPS  60
RFSGSGSGTD FTLTISSLQP EDFATYYCQQ SYSSPWTFGQ GTKVEIK               107

SEQ ID NO: 46          moltype = DNA  length = 321
FEATURE                Location/Qualifiers
misc_feature           1..321
                       note = VL of 5D5 antibody
source                 1..321
                       mol_type = other DNA
                       organism = synthetic construct
SEQUENCE: 46
gacattcaaa tgacgcagag tccctcctca ctgagtgcta gcgtgggcga tcgtgtgaca  60
attacttgtc gcgctagcca ggatatccgt aattggctga actggtatca gcagaaaccg  120
ggcaaggcgc caaaattgct gatttacgca gcatcctctc tgcagtctgg tgtaccgtcc  180
cgtttctctg gcagcggttc tggtacggat tttaccctga ccatctcaag cctccagcct  240
gaagattttg ccacctatta ttgtcagcaa tcttactctt ctccgtggac gttcgggcag  300
ggaactaaag tggaaattaa a                                            321

SEQ ID NO: 47          moltype = AA  length = 119
FEATURE                Location/Qualifiers
REGION                 1..119
                       note = VH of 4G4 antibody
source                 1..119
                       mol_type = protein
                       organism = synthetic construct
SEQUENCE: 47
EVQLVESGGG LVQPGGSLRL SCAASGFTFS NYAMSWVRQA PGKGLEWVSA ISGSGSSTYY  60
ADSVKGRFTI SRDNSKNTLY LQMNSLRAED TAVYYCAKAE YSYLYFDIWG QGTLVTVSS   119

SEQ ID NO: 48          moltype = DNA  length = 357
FEATURE                Location/Qualifiers
misc_feature           1..357
                       note = VH of 4G4 antibody
source                 1..357
                       mol_type = other DNA
                       organism = synthetic construct
SEQUENCE: 48
gaagtacagt tggtcgaaag tggcggtggc ctcgtgcaac cgggtggttc actgcgtctg  60
agctgcgccg cctcgggttt tactttctct aattatgcaa tgtcttgggt tcgtcaggcg  120
ccgggcaagg gtctcgaatg ggtttcagca atctctggtt ctggttcttc tacttactat  180
gccgattcag tgaagggtcg ctttaccatt tcccgtgaca actctaagaa tactctgtat  240
ctgcagatga actcgctgcg tgccgaagac acggccgtct attattgcgc caaagcagaa  300
tactcttacc tgtacttcga tatctggggt cagggcactt tagtgaccgt ctcatcg     357

SEQ ID NO: 49          moltype = AA  length = 107
FEATURE                Location/Qualifiers
REGION                 1..107
                       note = VL of 4G4 antibody
source                 1..107
                       mol_type = protein
                       organism = synthetic construct
SEQUENCE: 49
DIQMTQSPSS LSASVGDRVT ITCRASQSIS NWLNWYQQKP GKAPKLLIYA ASRLQSGVPS  60
RFSGSGSGTD FTLTISSLQP EDFATYYCQQ SYSSPWTFGQ GTKVEIK               107

SEQ ID NO: 50          moltype = DNA  length = 321
FEATURE                Location/Qualifiers
misc_feature           1..321
                       note = VL of 4G4 antibody
source                 1..321
                       mol_type = other DNA
                       organism = synthetic construct
SEQUENCE: 50
gacattcaaa tgacgcagag tccctcctca ctgagtgcta gcgtgggcga tcgtgtgaca  60
attacttgtc gcgctagcca gtctatctct aattggctga actggtatca gcagaaaccg  120
ggcaaggcgc caaaattgct gatttacgca gcatcccgtc tgcagtctgg tgtaccgtcc  180
cgtttctctg gcagcggttc tggtacggat tttaccctga ccatctcaag cctccagcct  240
gaagattttg ccacctatta ttgtcagcaa tcttactctt ctccgtggac gttcgggcag  300
ggaactaaag tggaaattaa a                                            321

SEQ ID NO: 51          moltype = AA  length = 121
FEATURE                Location/Qualifiers
REGION                 1..121
                       note = VH of 3E11 antibody
source                 1..121
                       mol_type = protein
                       organism = synthetic construct
SEQUENCE: 51
```

```
EVQLVESGGG LVQPGGSLRL SCAASGFTFS SYAMSWVRQA PGKGLEWVSA IYSSGGSTYY  60
ADSVKGRFTI SRDNSKNTLY LQMNSLRAED TAVYYCAKVG SAGYLYDFDY WGQGTLVTVS  120
S                                                                  121

SEQ ID NO: 52           moltype = DNA  length = 363
FEATURE                 Location/Qualifiers
misc_feature            1..363
                        note = VH of 3E11 antibody
source                  1..363
                        mol_type = other DNA
                        organism = synthetic construct
SEQUENCE: 52
gaagtacagt tggtcgaaag tggcggtggc ctcgtgcaac cgggtggttc actgcgtctg  60
agctgcgccg cctcgggttt tactttctct tcttatgcaa tgtcttgggt tcgtcaggcg  120
ccgggcaagg gtctcgaatg ggtttcagca atctactctt ctggtggttc tacttactat  180
gccgattcag tgaagggtcg ctttaccatt tcccgtgaca actctaagaa tactctgtat  240
ctgcagatga actcgctgcg tgccgaagac acggccgtct attattgcgc caaagttggt  300
tctgcaggtt acctgtacga tttcgattac tggggtcagg gcactttagt gaccgtctca  360
tcg                                                                363

SEQ ID NO: 53           moltype = AA  length = 107
FEATURE                 Location/Qualifiers
REGION                  1..107
                        note = VL of 3E11 antibody
source                  1..107
                        mol_type = protein
                        organism = synthetic construct
SEQUENCE: 53
DIQMTQSPSS LSASVGDRVT ITCRASQDIA NYLNWYQQKP GKAPKLLIYA TSTLQSGVPS  60
RFSGSGSGTD FTLTISSLQP EDFATYYCQQ SYSSPWTFGQ GTKVEIK                107

SEQ ID NO: 54           moltype = DNA  length = 321
FEATURE                 Location/Qualifiers
misc_feature            1..321
                        note = VL of 3E11 antibody
source                  1..321
                        mol_type = other DNA
                        organism = synthetic construct
SEQUENCE: 54
gacattcaaa tgacgcagag tccctcctca ctgagtgcta gcgtgggcga tcgtgtgaca  60
attacttgtc gcgctagcca ggatatcgca aattacctga actggtatca gcagaaaccg  120
ggcaaggcgc caaaattgct gatttacgca acttccactc tgcagtctgg tgtaccgtcc  180
cgtttctctg gcagcggttc tggtacggat tttaccctga ccatctcaag cctccagcct  240
gaagattttg ccacctatta ttgtcagcaa tcttactctt ctccgtggac gttcgggcag  300
ggaactaaag tggaaattaa a                                            321

SEQ ID NO: 55           moltype = AA  length = 119
FEATURE                 Location/Qualifiers
REGION                  1..119
                        note = VH of 4H7 antibody
source                  1..119
                        mol_type = protein
                        organism = synthetic construct
SEQUENCE: 55
EVQLVESGGG LVQPGGSLRL SCAASGFTFS TYGMSWVRQA PGKGLEWVSA ISSSGGSIYY  60
ADSVKGRFTI SRDNSKNTLY LQMNSLRAED TAVYYCAKVS YPGLAFDIWG QGTLVTVSS   119

SEQ ID NO: 56           moltype = DNA  length = 357
FEATURE                 Location/Qualifiers
misc_feature            1..357
                        note = VH of 4H7 antibody
source                  1..357
                        mol_type = other DNA
                        organism = synthetic construct
SEQUENCE: 56
gaagtacagt tggtcgaaag tggcggtggc ctcgtgcaac cgggtggttc actgcgtctg  60
agctgcgccg cctcgggttt tactttctct acttatggta tgtcttgggt tcgtcaggcg  120
ccgggcaagg gtctcgaatg ggtttcagca atctcttctt ctggtggttc tatctactat  180
gccgattcag tgaagggtcg ctttaccatt tcccgtgaca actctaagaa tactctgtat  240
ctgcagatga actcgctgcg tgccgaagac acggccgtct attattgcgc caaagtttct  300
tacccgggtc tggcattcga tatctggggt cagggcactt tagtgaccgt ctcatcg     357

SEQ ID NO: 57           moltype = AA  length = 107
FEATURE                 Location/Qualifiers
REGION                  1..107
                        note = VL of 4H7 antibody
source                  1..107
                        mol_type = protein
                        organism = synthetic construct
```

```
SEQUENCE: 57
DIQMTQSPSS LSASVGDRVT ITCRASQTIS NYLNWYQQKP GKAPKLLIYA TSSLQSGVPS  60
RFSGSGSGTD FTLTISSLQP EDFATYYCQQ SYSSPWTFGQ GTKVEIK                107

SEQ ID NO: 58          moltype = DNA  length = 321
FEATURE                Location/Qualifiers
misc_feature           1..321
                       note = VL of 4H7 antibody
source                 1..321
                       mol_type = other DNA
                       organism = synthetic construct
SEQUENCE: 58
gacattcaaa tgacgcagag tccctcctca ctgagtgcta gcgtgggcga tcgtgtgaca  60
attacttgtc gcgctagcca gactatctct aattacctga actggtatca gcagaaaccg  120
ggcaaggcgc caaaattgct gatttacgca acttcctctc tgcagtctgg tgtaccgtcc  180
cgtttctctg gcagcggttc tggtacggat tttaccctga ccatctcaag cctccagcct  240
gaagattttg ccacctatta ttgtcagcaa tcttactctt ctccgtggac gttcgggcag  300
ggaactaaag tggaaattaa a                                            321

SEQ ID NO: 59          moltype = AA  length = 619
FEATURE                Location/Qualifiers
REGION                 1..619
                       note = Human TLR5 extracellular domain of hTLR5-FC
source                 1..619
                       mol_type = protein
                       organism = synthetic construct
SEQUENCE: 59
IPSCSFDGRI AFYRFCNLTQ VPQVLNTTER LLLSFNYIRT VTASSFPFLE QLQLLELGSQ  60
YTPLTIDKEA FRNLPNLRIL DLGSSKIYFL HPDAFQGLFH LFELRLYFCG LSDAVLKDGY  120
FRNLKALTRL DLSKNQIRSL YLHPSFGKLN SLKSIDFSSN QIFLVCEHEL EPLQGKTLSF  180
FSLAANSLYS RVSVDWGKCM NPFRNMVLEI LDVSGNGWTV DITGNFSNAI SKSQAFSLIL  240
AHHIMGAGFG FHNIKDPDQN TFAGLARSSV RHLDLSHGFV FSLNSRVFET LKDLKVLNLA  300
YNKINKIADE AFYGLDNLQV LNLSYNLLGE LYSSNFYGLP KVAYIDLQKN HIAIIQDQTF  360
KFLEKLQTLD LRDNALTTIH FIPSIPDIFL SGNKLVTLPK INLTANLIHL SENRLENLDI  420
LYFLLRVPHL QILILNQNRF SSCSGDQTPS ENPSLEQLFL GENMLQLAWE TELCWDVFEG  480
LSHLQVLYLN HNYLNSLPPG VFSHLTALRG LSLNSNRLTV LSHNDLPANL EILDISRNQL  540
LAPNPDVFVS LSVLDITHNK FICECELSTF INWLNHTNVT IAGPPADIYC VYPDSFSGVS  600
LFSLSTEGCD EEEVLKSLK                                               619

SEQ ID NO: 60          moltype = AA  length = 7
FEATURE                Location/Qualifiers
REGION                 1..7
                       note = epitope in SH3YL1 for 5D5 antibody
source                 1..7
                       mol_type = protein
                       organism = synthetic construct
SEQUENCE: 60
WWEGKLR                                                            7

SEQ ID NO: 61          moltype = AA  length = 331
FEATURE                Location/Qualifiers
REGION                 1..331
                       note = CH of 4F9, 4F10, 5D5, 4G4, 3E11, and 4H7 antibodies
source                 1..331
                       mol_type = protein
                       organism = synthetic construct
SEQUENCE: 61
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP PKSCDKTHTC PPCPAPELLG  120
GPSVFLFPPK PKDTLMISRT PEVTCVVVDV SHEDPEVKFN WYVDGVEVHN AKTKPREEQY  180
NSTYRVVSVL TVLHQDWLNG KEYKCKVSNK ALPAPIEKTI SKAKGQPREP QVYTLPPSRD  240
ELTKNQVSLT CLVKGFYPSD IAVEWESNGQ PENNYKTTPP VLDSDGSFFL YSKLTVDKSR  300
WQQGNVFSCS VMHEALHNHY TQKSLSLSPG K                                 331

SEQ ID NO: 62          moltype = AA  length = 107
FEATURE                Location/Qualifiers
REGION                 1..107
                       note = CL of 4F9, 4F10, 5D5, 4G4, 3E11, and 4H7 antibodies
source                 1..107
                       mol_type = protein
                       organism = synthetic construct
SEQUENCE: 62
RSVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 63          moltype = AA  length = 5
FEATURE                Location/Qualifiers
REGION                 1..5
                       note = VH CDR1 of S4A antibody
```

```
source                  1..5
                        mol_type = protein
                        organism = synthetic construct
SEQUENCE: 63
SYSMN                                                                      5

SEQ ID NO: 64           moltype = AA  length = 17
FEATURE                 Location/Qualifiers
REGION                  1..17
                        note = VH CDR2 of S4A antibody
source                  1..17
                        mol_type = protein
                        organism = synthetic construct
SEQUENCE: 64
WISPNSGSTD YAQKFQG                                                         17

SEQ ID NO: 65           moltype = AA  length = 9
FEATURE                 Location/Qualifiers
REGION                  1..9
                        note = VH CDR3 of S4A antibody
source                  1..9
                        mol_type = protein
                        organism = synthetic construct
SEQUENCE: 65
TPPGTPFDY                                                                  9

SEQ ID NO: 66           moltype = AA  length = 11
FEATURE                 Location/Qualifiers
REGION                  1..11
                        note = VL CDR1 of S4A antibody
source                  1..11
                        mol_type = protein
                        organism = synthetic construct
SEQUENCE: 66
SGNNIGSKSV H                                                               11

SEQ ID NO: 67           moltype = AA  length = 7
FEATURE                 Location/Qualifiers
REGION                  1..7
                        note = VL CDR2 of S4A antibody
source                  1..7
                        mol_type = protein
                        organism = synthetic construct
SEQUENCE: 67
STSNKHS                                                                    7

SEQ ID NO: 68           moltype = AA  length = 10
FEATURE                 Location/Qualifiers
REGION                  1..10
                        note = VL CDR3 of S4A antibody
source                  1..10
                        mol_type = protein
                        organism = synthetic construct
SEQUENCE: 68
SSYTSSGTRV                                                                 10

SEQ ID NO: 69           moltype = AA  length = 5
FEATURE                 Location/Qualifiers
REGION                  1..5
                        note = VH CDR1 of 4F9, 4F10, and 5D5 antibodies
source                  1..5
                        mol_type = protein
                        organism = synthetic construct
SEQUENCE: 69
DYAMS                                                                      5

SEQ ID NO: 70           moltype = AA  length = 17
FEATURE                 Location/Qualifiers
REGION                  1..17
                        note = VH CDR2 of 4F9 antibody
source                  1..17
                        mol_type = protein
                        organism = synthetic construct
SEQUENCE: 70
AIKSSGSSTY YADSVKG                                                         17

SEQ ID NO: 71           moltype = AA  length = 10
FEATURE                 Location/Qualifiers
REGION                  1..10
```

```
                        note = VH CDR3 of 4F9 antibody
source                  1..10
                        mol_type = protein
                        organism = synthetic construct
SEQUENCE: 71
AEYEYLAFDI                                                 10

SEQ ID NO: 72           moltype = AA  length = 11
FEATURE                 Location/Qualifiers
REGION                  1..11
                        note = VL CDR1 of 4F9 antibody
source                  1..11
                        mol_type = protein
                        organism = synthetic construct
SEQUENCE: 72
RASQDISSWL N                                               11

SEQ ID NO: 73           moltype = AA  length = 7
FEATURE                 Location/Qualifiers
REGION                  1..7
                        note = VL CDR2 of 4F9 and 3E11 antibodies
source                  1..7
                        mol_type = protein
                        organism = synthetic construct
SEQUENCE: 73
ATSTLQS                                                    7

SEQ ID NO: 74           moltype = AA  length = 9
FEATURE                 Location/Qualifiers
REGION                  1..9
                        note = VL CDR3 of 4F9, 4G4, 3E11, and 4H7 antibodies
source                  1..9
                        mol_type = protein
                        organism = synthetic construct
SEQUENCE: 74
QQSYSSPWT                                                  9

SEQ ID NO: 75           moltype = AA  length = 17
FEATURE                 Location/Qualifiers
REGION                  1..17
                        note = VH CDR2 of 4F10 antibody
source                  1..17
                        mol_type = protein
                        organism = synthetic construct
SEQUENCE: 75
AIYSTGSSTY YADSVKG                                         17

SEQ ID NO: 76           moltype = AA  length = 8
FEATURE                 Location/Qualifiers
REGION                  1..8
                        note = VH CDR3 of 4F10 antibody
source                  1..8
                        mol_type = protein
                        organism = synthetic construct
SEQUENCE: 76
VGWYLFDY                                                   8

SEQ ID NO: 77           moltype = AA  length = 11
FEATURE                 Location/Qualifiers
REGION                  1..11
                        note = VL CDR1 of 4F10 antibody
source                  1..11
                        mol_type = protein
                        organism = synthetic construct
SEQUENCE: 77
RASQSISRYL N                                               11

SEQ ID NO: 78           moltype = AA  length = 7
FEATURE                 Location/Qualifiers
REGION                  1..7
                        note = VL CDR2 of 4F10 antibody
source                  1..7
                        mol_type = protein
                        organism = synthetic construct
SEQUENCE: 78
ATSRLQS                                                    7

SEQ ID NO: 79           moltype = AA  length = 9
FEATURE                 Location/Qualifiers
```

```
REGION                 1..9
                       note = VL CDR3 of 4F10 antibody
source                 1..9
                       mol_type = protein
                       organism = synthetic construct
SEQUENCE: 79
QQSYSSPWT                                                        9

SEQ ID NO: 80          moltype = AA  length = 17
FEATURE                Location/Qualifiers
REGION                 1..17
                       note = VH CDR2 of 5D5 antibody
source                 1..17
                       mol_type = protein
                       organism = synthetic construct
SEQUENCE: 80
SISSTGSTTY YADSVKG                                               17

SEQ ID NO: 81          moltype = AA  length = 10
FEATURE                Location/Qualifiers
REGION                 1..10
                       note = VH CDR3 of 5D5 antibody
source                 1..10
                       mol_type = protein
                       organism = synthetic construct
SEQUENCE: 81
VLYEYLYFDY                                                       10

SEQ ID NO: 82          moltype = AA  length = 11
FEATURE                Location/Qualifiers
REGION                 1..11
                       note = VL CDR1 of 5D5 antibody
source                 1..11
                       mol_type = protein
                       organism = synthetic construct
SEQUENCE: 82
RASQDIRNWL N                                                     11

SEQ ID NO: 83          moltype = AA  length = 7
FEATURE                Location/Qualifiers
REGION                 1..7
                       note = VL CDR2 of 5D5 antibody
source                 1..7
                       mol_type = protein
                       organism = synthetic construct
SEQUENCE: 83
AASSLQS                                                          7

SEQ ID NO: 84          moltype = AA  length = 9
FEATURE                Location/Qualifiers
REGION                 1..9
                       note = VL CDR3 of 5D5 antibody
source                 1..9
                       mol_type = protein
                       organism = synthetic construct
SEQUENCE: 84
QQSYSSPWT                                                        9

SEQ ID NO: 85          moltype = AA  length = 17
FEATURE                Location/Qualifiers
REGION                 1..17
                       note = VH CDR2 of 4G4 antibody
source                 1..17
                       mol_type = protein
                       organism = synthetic construct
SEQUENCE: 85
AISGSGSSTY YADSVKG                                               17

SEQ ID NO: 86          moltype = AA  length = 10
FEATURE                Location/Qualifiers
REGION                 1..10
                       note = VH CDR3 of 4G4 antibody
source                 1..10
                       mol_type = protein
                       organism = synthetic construct
SEQUENCE: 86
AEYSYLYFDI                                                       10

SEQ ID NO: 87          moltype = AA  length = 11
```

```
FEATURE                 Location/Qualifiers
REGION                  1..11
                        note = VL CDR1 of 4G4 antibody
source                  1..11
                        mol_type = protein
                        organism = synthetic construct
SEQUENCE: 87
RASQSISNWL N                                                   11

SEQ ID NO: 88           moltype = AA  length = 7
FEATURE                 Location/Qualifiers
REGION                  1..7
                        note = VL CDR2 of 4G4 antibody
source                  1..7
                        mol_type = protein
                        organism = synthetic construct
SEQUENCE: 88
AASRLQS                                                        7

SEQ ID NO: 89           moltype = AA  length = 5
FEATURE                 Location/Qualifiers
REGION                  1..5
                        note = VH CDR1 of 3E11 antibody
source                  1..5
                        mol_type = protein
                        organism = synthetic construct
SEQUENCE: 89
SYAMS                                                          5

SEQ ID NO: 90           moltype = AA  length = 17
FEATURE                 Location/Qualifiers
REGION                  1..17
                        note = VH CDR2 of 3E11 antibody
source                  1..17
                        mol_type = protein
                        organism = synthetic construct
SEQUENCE: 90
AIYSSGGSTY YADSVKG                                             17

SEQ ID NO: 91           moltype = AA  length = 12
FEATURE                 Location/Qualifiers
REGION                  1..12
                        note = VH CDR3 of 3E11 antibody
source                  1..12
                        mol_type = protein
                        organism = synthetic construct
SEQUENCE: 91
VGSAGYLYDF DY                                                  12

SEQ ID NO: 92           moltype = AA  length = 11
FEATURE                 Location/Qualifiers
REGION                  1..11
                        note = VL CDR1 of 3E11 antibody
source                  1..11
                        mol_type = protein
                        organism = synthetic construct
SEQUENCE: 92
RASQDIANYL N                                                   11

SEQ ID NO: 93           moltype = AA  length = 5
FEATURE                 Location/Qualifiers
REGION                  1..5
                        note = VH CDR1 of 4H7 antibody
source                  1..5
                        mol_type = protein
                        organism = synthetic construct
SEQUENCE: 93
TYGMS                                                          5

SEQ ID NO: 94           moltype = AA  length = 17
FEATURE                 Location/Qualifiers
REGION                  1..17
                        note = VH CDR2 of 4H7 antibody
source                  1..17
                        mol_type = protein
                        organism = synthetic construct
SEQUENCE: 94
AISSSGGSIY YADSVKG                                             17
```

-continued

```
SEQ ID NO: 95           moltype = AA  length = 10
FEATURE                 Location/Qualifiers
REGION                  1..10
                        note = VH CDR3 of 4H7 antibody
source                  1..10
                        mol_type = protein
                        organism = synthetic construct
SEQUENCE: 95
VSYPGLAFDI                                                   10

SEQ ID NO: 96           moltype = AA  length = 11
FEATURE                 Location/Qualifiers
REGION                  1..11
                        note = VL CDR1 of 4H7 antibody
source                  1..11
                        mol_type = protein
                        organism = synthetic construct
SEQUENCE: 96
RASQTISNYL N                                                 11

SEQ ID NO: 97           moltype = AA  length = 7
FEATURE                 Location/Qualifiers
REGION                  1..7
                        note = VL CDR2 of 4H7 antibody
source                  1..7
                        mol_type = protein
                        organism = synthetic construct
SEQUENCE: 97
ATSSLQS                                                      7

SEQ ID NO: 98           moltype = AA  length = 7
FEATURE                 Location/Qualifiers
REGION                  1..7
                        note = epitope in SH3YL1 for S4A antibody
source                  1..7
                        mol_type = protein
                        organism = synthetic construct
SEQUENCE: 98
SHFDWWE                                                      7

SEQ ID NO: 99           moltype = AA  length = 7
FEATURE                 Location/Qualifiers
REGION                  1..7
                        note = epitope in SH3YL1 for 4F9, 4G4, 3E11, and 4H7
                         antibodies
source                  1..7
                        mol_type = protein
                        organism = synthetic construct
SEQUENCE: 99
DWWEGKL                                                      7

SEQ ID NO: 100          moltype = AA  length = 7
FEATURE                 Location/Qualifiers
REGION                  1..7
                        note = epitope in SH3YL1 for 4F10 antibody
source                  1..7
                        mol_type = protein
                        organism = synthetic construct
SEQUENCE: 100
FDWWEGK                                                      7
```

What is claimed is:

1. A method of treating diabetic nephropathy and/or non-alcoholic steatosis hepatitis in a subject, the method comprising administering to the subject an effective amount of an antibody that binds to SH3domain-containing YSC84-like 1 (SH3YL1), comprising:

(a) a heavy chain variable region comprising
- a heavy chain complementarity determining region 1 (CDR1) comprising the amino acid sequence NYAMS (SEQ ID NO:13),
- a heavy chain CDR2 comprising the amino acid sequence VISSDNSSTYYADSVKG (SEQ ID NO:14), and
- a heavy chain CDR3 comprising the amino acid sequence VWRHFDY (SEQ ID NO: 15), and a light chain variable region comprising
- a light chain CDR1 comprising the amino acid sequence SGSSSNIGSNNVN (SEQ ID NO: 16),
- a light chain CDR2 comprising the amino acid sequence ADSHRPS (SEQ ID NO: 17), and
- a light chain CDR3 comprising the amino acid sequence ASWDSSLSGYV (SEQ ID NO: 18); or (b) a heavy chain variable region comprising
- a heavy chain CDR1 comprising the amino acid sequence NYYMS (SEQ ID NO: 19),
- a heavy chain CDR2 comprising the amino acid sequence AISHNNSNTYYADSVKG (SEQ ID NO:20), and
- a heavy chain CDR3 comprising the amino acid sequence KFSFFDY (SEQ ID NO: 21), and a light chain variable region comprising
a light chain CDR1 comprising the amino acid sequence SGSSSNIGSNYVS (SEQ ID NO: 22),
a light chain CDR2 comprising the amino acid sequence ANSHRPS (SEQ ID NO: 23), and a light chain CDR3 comprising the amino acid sequence GAWDSSLNGYV (SEQ ID NO:24).

2. The method of claim 1, wherein the heavy chain variable region comprises the amino acid sequence of SEQ ID NO:1 or 5.

3. The method of claim 1, wherein the light chain variable region comprises the amino acid sequence of SEQ ID NO:3 or 7.

4. The method of claim 1, wherein the heavy chain constant region comprises an amino acid sequence of SEQ ID NO:9 and/or the light chain constant region comprises an amino acid sequence of SEQ ID NO: 10.

5. A method of treating acute kidney injury and/or inflammatory bowel disease in a subject, the method comprising administering to the subject an effective amount of an antibody that binds to SH3domain-containing YSC84-like 1 (SH3YL1), comprising:
(a) a heavy chain variable region comprising
a heavy chain complementarity determining region 1 (CDR1) comprising the amino acid sequence NYAMS (SEQ ID NO:13),
a heavy chain CDR2 comprising the amino acid sequence VISSDNSSTYYADSVKG (SEQ ID NO:14), and
a heavy chain CDR3 comprising the amino acid sequence VWRHFDY (SEQ ID NO: 15), and
a light chain variable region comprising
a light chain CDR1 comprising the amino acid sequence SGSSSNIGSNNVN (SEQ ID NO: 16),
a light chain CDR2 comprising the amino acid sequence ADSHRPS (SEQ ID NO: 17), and
a light chain CDR3 comprising the amino acid sequence ASWDSSLSGYV (SEQ ID NO: 18); or
(b) a heavy chain variable region comprising
a heavy chain CDR1 comprising the amino acid sequence NYYMS (SEQ ID NO: 19),
a heavy chain CDR2 comprising the amino acid sequence AISHNNSNTYYADSVKG (SEQ ID NO:20), and
a heavy chain CDR3 comprising the amino acid sequence KFSFFDY (SEQ ID NO: 21), and
a light chain variable region comprising
a light chain CDR1 comprising the amino acid sequence SGSSSNIGSNYVS (SEQ ID NO: 22),
a light chain CDR2 comprising the amino acid sequence ANSHRPS (SEQ ID NO: 23), and a light chain CDR3 comprising the amino acid sequence GAWDSSLNGYV (SEQ ID NO:24).

6. The method of claim 5, wherein the heavy chain variable region comprises the amino acid sequence of SEQ ID NO: 1 or 5.

7. The method of claim 5, wherein the light chain variable region comprises the amino acid sequence of SEQ ID NO:3 or 7.

8. The method of claim 5, wherein the heavy chain constant region comprises an amino acid sequence of SEQ ID NO:9 and/or the light chain constant region comprises an amino acid sequence of SEQ ID NO:10.

9. A method of modulating an immune response in a subject, the method comprising administering to the subject an effective amount of an antibody that binds to SH3domain-containing YSC84-like 1 (SH3YL1), comprising:
(a) a heavy chain variable region comprising
a heavy chain complementarity determining region 1 (CDR1) comprising the amino acid sequence NYAMS (SEQ ID NO:13),
a heavy chain CDR2 comprising the amino acid sequence VISSDNSSTYYADSVKG (SEQ ID NO:14), and
a heavy chain CDR3 comprising the amino acid sequence VWRHFDY (SEQ ID NO: 15), and
a light chain variable region comprising
a light chain CDR1 comprising the amino acid sequence SGSSSNIGSNNVN (SEQ ID NO: 16),
a light chain CDR2 comprising the amino acid sequence ADSHRPS (SEQ ID NO: 17), and
a light chain CDR3 comprising the amino acid sequence ASWDSSLSGYV (SEQ ID NO: 18); or
(b) a heavy chain variable region comprising
a heavy chain CDR1 comprising the amino acid sequence NYYMS (SEQ ID NO: 19),
a heavy chain CDR2 comprising the amino acid sequence AISHNNSNTYYADSVKG (SEQ ID NO:20), and
a heavy chain CDR3 comprising the amino acid sequence KFSFFDY (SEQ ID NO: 21), and
a light chain variable region comprising
a light chain CDR1 comprising the amino acid sequence SGSSSNIGSNYVS (SEQ ID NO: 22),
a light chain CDR2 comprising the amino acid sequence ANSHRPS (SEQ ID NO: 23), and a light chain CDR3 comprising the amino acid sequence GAWDSSLNGYV (SEQ ID NO:24).

10. The method of claim 9, which is a method for enhancing or inducing the immune response of the subject.

11. A method of treating diabetic nephropathy and/or non-alcoholic steatosis hepatitis in a subject, the method comprising administering to the subject an effective amount of an antibody that binds to SH3domain-containing YSC84-like 1 (SH3YL1), comprising:
(a) a heavy chain variable region comprising
a heavy chain complementarity determining region 1 (CDR1) comprising the amino acid sequence of SEQ ID NO:63,
a heavy chain CDR2 comprising the amino acid sequence of SEQ ID NO:64, and
a heavy chain CDR3 comprising the amino acid sequence of SEQ ID NO:65; and
a light chain variable region comprising
a light chain CDR1 comprising the amino acid sequence of SEQ ID NO:66,
a light chain CDR2 comprising the amino acid sequence of SEQ ID NO:67, and
a light chain CDR3 comprising the amino acid sequence of SEQ ID NO:68;
(b) a heavy chain variable region comprising
a heavy chain CDR1 comprising the amino acid sequence of SEQ ID NO:69,
a heavy chain CDR2 comprising the amino acid sequence of SEQ ID NO:70, and
a heavy chain CDR3 comprising the amino acid sequence of SEQ ID NO:71; and
a light chain variable region comprising
a light chain CDR1 comprising the amino acid sequence of SEQ ID NO:72,
a light chain CDR2 comprising the amino acid sequence of SEQ ID NO:73, and
a light chain CDR3 comprising the amino acid sequence of SEQ ID NO:74;

(c) a heavy chain variable region comprising
a heavy chain CDR1 comprising the amino acid sequence of SEQ ID NO:69,
a heavy chain CDR2 comprising the amino acid sequence of SEQ ID NO:75, and
a heavy chain CDR3 comprising the amino acid sequence of SEQ ID NO:76; and
a light chain variable region comprising
a light chain CDR1 comprising the amino acid sequence of SEQ ID NO:77,
a light chain CDR2 comprising the amino acid sequence of SEQ ID NO:78, and
a light chain CDR3 comprising the amino acid sequence of SEQ ID NO:79;
(d) a heavy chain variable region comprising
a heavy chain CDR1 comprising the amino acid sequence of SEQ ID NO:69,
a heavy chain CDR2 comprising the amino acid sequence of SEQ ID NO:80, and
a heavy chain CDR3 comprising the amino acid sequence of SEQ ID NO:81; and
a light chain variable region comprising
a light chain CDR1 comprising the amino acid sequence of SEQ ID NO:82,
a light chain CDR2 comprising the amino acid sequence of SEQ ID NO:83, and
a light chain CDR3 comprising the amino acid sequence of SEQ ID NO:84;
(e) a heavy chain variable region comprising
a heavy chain CDR1 comprising the amino acid sequence of SEQ ID NO:13,
a heavy chain CDR2 comprising the amino acid sequence of SEQ ID NO:85, and
a heavy chain CDR3 comprising the amino acid sequence of SEQ ID NO:86; and
a light chain variable region comprising
a light chain CDR1 comprising the amino acid sequence of SEQ ID NO:87,
a light chain CDR2 comprising the amino acid sequence of SEQ ID NO:88, and
a light chain CDR3 comprising the amino acid sequence of SEQ ID NO:74;
(f) a heavy chain variable region comprising
a heavy chain CDR1 comprising the amino acid sequence of SEQ ID NO:89,
a heavy chain CDR2 comprising the amino acid sequence of SEQ ID NO:90, and
a heavy chain CDR3 comprising the amino acid sequence of SEQ ID NO:91; and
a light chain variable region comprising
a light chain CDR1 comprising the amino acid sequence of SEQ ID NO:92,
a light chain CDR2 comprising the amino acid sequence of SEQ ID NO:73, and
a light chain CDR3 comprising the amino acid sequence of SEQ ID NO:74; or
(g) a heavy chain variable region comprising
a heavy chain CDR1 comprising the amino acid sequence of SEQ ID NO:93,
a heavy chain CDR2 comprising the amino acid sequence of SEQ ID NO:94, and
a heavy chain CDR3 comprising the amino acid sequence of SEQ ID NO:95; and
a light chain variable region comprising
a light chain CDR1 comprising the amino acid sequence of SEQ ID NO:96,
a light chain CDR2 comprising the amino acid sequence of SEQ ID NO:97, and
a light chain CDR3 comprising the amino acid sequence of SEQ ID NO:74.

12. The method of claim 11, wherein the heavy chain variable region comprises the amino acid sequence of SEQ ID NO:31, 35, 39, 43, 47, 51, or 55.

13. The method of claim 11, wherein the light chain variable region comprises the amino acid sequence of SEQ ID NO:33, 37, 41, 45, 49, 53, or 57.

14. The method of claim 11, wherein the heavy chain constant region comprises an amino acid sequence of SEQ ID NO:61 and/or the light chain constant region comprises an amino acid sequence of SEQ ID NO:62.

15. A method of treating acute kidney injury and/or inflammatory bowel disease in a subject, the method comprising administering to the subject an effective amount of an antibody that binds to SH3domain-containing YSC84-like 1 (SH3YL1), comprising:
(a) a heavy chain variable region comprising
a heavy chain complementarity determining region 1 (CDR1) comprising the amino acid sequence of SEQ ID NO:63,
a heavy chain CDR2 comprising the amino acid sequence of SEQ ID NO:64, and
a heavy chain CDR3 comprising the amino acid sequence of SEQ ID NO:65; and
a light chain variable region comprising
a light chain CDR1 comprising the amino acid sequence of SEQ ID NO:66,
a light chain CDR2 comprising the amino acid sequence of SEQ ID NO:67, and
a light chain CDR3 comprising the amino acid sequence of SEQ ID NO:68;
(b) a heavy chain variable region comprising
a heavy chain CDR1 comprising the amino acid sequence of SEQ ID NO:69,
a heavy chain CDR2 comprising the amino acid sequence of SEQ ID NO:70, and
a heavy chain CDR3 comprising the amino acid sequence of SEQ ID NO:71; and
a light chain variable region comprising
a light chain CDR1 comprising the amino acid sequence of SEQ ID NO:72,
a light chain CDR2 comprising the amino acid sequence of SEQ ID NO:73, and
a light chain CDR3 comprising the amino acid sequence of SEQ ID NO:74;
(c) a heavy chain variable region comprising
a heavy chain CDR1 comprising the amino acid sequence of SEQ ID NO:69,
a heavy chain CDR2 comprising the amino acid sequence of SEQ ID NO:75, and
a heavy chain CDR3 comprising the amino acid sequence of SEQ ID NO:76; and
a light chain variable region comprising
a light chain CDR1 comprising the amino acid sequence of SEQ ID NO:77,
a light chain CDR2 comprising the amino acid sequence of SEQ ID NO:78, and
a light chain CDR3 comprising the amino acid sequence of SEQ ID NO:79;
(d) a heavy chain variable region comprising
a heavy chain CDR1 comprising the amino acid sequence of SEQ ID NO:69,
a heavy chain CDR2 comprising the amino acid sequence of SEQ ID NO:80, and a heavy chain CDR3 comprising the amino acid sequence of SEQ ID NO:81; and a light chain variable region comprising a light chain CDR1 comprising the amino acid sequence of SEQ ID NO:82, a light chain CDR2 comprising the amino acid sequence of SEQ ID NO:83, and a light chain CDR3 comprising the amino acid sequence of SEQ ID NO:84;

(e) a heavy chain variable region comprising a heavy chain CDR1 comprising the amino acid sequence of SEQ ID NO:13, a heavy chain CDR2 comprising the amino acid sequence of SEQ ID NO:85, and a heavy chain CDR3 comprising the amino acid sequence of SEQ ID NO:86; and a light chain variable region comprising a light chain CDR1 comprising the amino acid sequence of SEQ ID NO:87, a light chain CDR2 comprising the amino acid sequence of SEQ ID NO:88, and a light chain CDR3 comprising the amino acid sequence of SEQ ID NO:74;

(f) a heavy chain variable region comprising a heavy chain CDR1 comprising the amino acid sequence of SEQ ID NO:89, a heavy chain CDR2 comprising the amino acid sequence of SEQ ID NO:90, and a heavy chain CDR3 comprising the amino acid sequence of SEQ ID NO:91; and a light chain variable region comprising a light chain CDR1 comprising the amino acid sequence of SEQ ID NO:92, a light chain CDR2 comprising the amino acid sequence of SEQ ID NO:73, and a light chain CDR3 comprising the amino acid sequence of SEQ ID NO:74; or (g) a heavy chain variable region comprising a heavy chain CDR1 comprising the amino acid sequence of SEQ ID NO:93, a heavy chain CDR2 comprising the amino acid sequence of SEQ ID NO:94, and a heavy chain CDR3 comprising the amino acid sequence of SEQ ID NO:95; and a light chain variable region comprising a light chain CDR1 comprising the amino acid sequence of SEQ ID NO:96, a light chain CDR2 comprising the amino acid sequence of SEQ ID NO:97, and a light chain CDR3 comprising the amino acid sequence of SEQ ID NO:74.

16. The method of claim 15, wherein the heavy chain variable region comprises the amino acid sequence of SEQ ID NO:31, 35, 39, 43, 47, 51, or 55.

17. The method of claim 15, wherein the light chain variable region comprises the amino acid sequence of SEQ ID NO:33, 37, 41, 45, 49, 53, or 57.

18. The method of claim 15, wherein the heavy chain constant region comprises an amino acid sequence of SEQ ID NO:61 and/or the light chain constant region comprises an amino acid sequence of SEQ ID NO:62.

19. A method of modulating an immune response in a subject, the method comprising administering to the subject an effective amount of an antibody that binds to SH3domain-containing YSC84-like 1 (SH3YL1), comprising:

(a) a heavy chain variable region comprising a heavy chain complementarity determining region 1 (CDR1) comprising the amino acid sequence of SEQ ID NO:63, a heavy chain CDR2 comprising the amino acid sequence of SEQ ID NO:64, and a heavy chain CDR3 comprising the amino acid sequence of SEQ ID NO:65; and a light chain variable region comprising a light chain CDR1 comprising the amino acid sequence of SEQ ID NO:66, a light chain CDR2 comprising the amino acid sequence of SEQ ID NO:67, and a light chain CDR3 comprising the amino acid sequence of SEQ ID NO:68;

(b) a heavy chain variable region comprising a heavy chain CDR1 comprising the amino acid sequence of SEQ ID NO:69, a heavy chain CDR2 comprising the amino acid sequence of SEQ ID NO:70, and a heavy chain CDR3 comprising the amino acid sequence of SEQ ID NO:71; and a light chain variable region comprising a light chain CDR1 comprising the amino acid sequence of SEQ ID NO:72, a light chain CDR2 comprising the amino acid sequence of SEQ ID NO:73, and a light chain CDR3 comprising the amino acid sequence of SEQ ID NO:74;

(c) a heavy chain variable region comprising a heavy chain CDR1 comprising the amino acid sequence of SEQ ID NO:69, a heavy chain CDR2 comprising the amino acid sequence of SEQ ID NO:75, and a heavy chain CDR3 comprising the amino acid sequence of SEQ ID NO:76; and a light chain variable region comprising a light chain CDR1 comprising the amino acid sequence of SEQ ID NO:77, a light chain CDR2 comprising the amino acid sequence of SEQ ID NO:78, and a light chain CDR3 comprising the amino acid sequence of SEQ ID NO:79;

(d) a heavy chain variable region comprising a heavy chain CDR1 comprising the amino acid sequence of SEQ ID NO:69, a heavy chain CDR2 comprising the amino acid sequence of SEQ ID NO:80, and a heavy chain CDR3 comprising the amino acid sequence of SEQ ID NO:81; and a light chain variable region comprising a light chain CDR1 comprising the amino acid sequence of SEQ ID NO:82, a light chain CDR2 comprising the amino acid sequence of SEQ ID NO:83, and a light chain CDR3 comprising the amino acid sequence of SEQ ID NO:84;

(e) a heavy chain variable region comprising a heavy chain CDR1 comprising the amino acid sequence of SEQ ID NO: 13, a heavy chain CDR2 comprising the amino acid sequence of SEQ ID NO:85, and a heavy chain CDR3 comprising the amino acid sequence of SEQ ID NO:86; and a light chain variable region comprising a light chain CDR1 comprising the amino acid sequence of SEQ ID NO:87, a light chain CDR2 comprising the amino acid sequence of SEQ ID NO:88, and a light chain CDR3 comprising the amino acid sequence of SEQ ID NO:74;

(f) a heavy chain variable region comprising a heavy chain CDR1 comprising the amino acid sequence of SEQ ID NO:89, a heavy chain CDR2 comprising the amino acid sequence of SEQ ID NO:90, and a heavy chain CDR3 comprising the amino acid sequence of SEQ ID NO:91; and a light chain variable region comprising a light chain CDR1 comprising the amino acid sequence of SEQ ID NO:92, a light chain CDR2 comprising the amino acid sequence of SEQ ID NO:73, and a light chain CDR3 comprising the amino acid sequence of SEQ ID NO:74; or (g) a heavy chain variable region comprising a heavy chain CDR1 comprising the amino acid sequence of SEQ ID NO:93, a heavy chain CDR2 comprising the amino acid sequence of SEQ ID NO:94, and a heavy chain CDR3 comprising the amino acid sequence of SEQ ID NO:95; and a light chain variable region comprising a light chain CDR1 comprising the amino acid sequence of SEQ ID NO:96, a light chain CDR2 comprising the amino acid sequence of SEQ ID NO:97, and a light chain CDR3 comprising the amino acid sequence of SEQ ID NO:74.

20. The method of claim 19, which is a method for enhancing or inducing the immune response of the subject.

* * * * *